United States Patent
Amit et al.

(10) Patent No.: US 12,415,985 B2
(45) Date of Patent: Sep. 16, 2025

(54) CULTURE MEDIA, CELL CULTURES AND METHODS OF CULTURING PLURIPOTENT STEM CELLS IN AN UNDIFFERENTIATED STATE

(71) Applicant: Technion Research & Development Foundation Limited, Haifa (IL)

(72) Inventors: Michal Amit, Yuvalim (IL); Joseph Itskovitz-Eldor, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 1015 days.

(21) Appl. No.: 17/097,023

(22) Filed: Nov. 13, 2020

(65) Prior Publication Data

US 2021/0079342 A1 Mar. 18, 2021

Related U.S. Application Data

(60) Division of application No. 14/696,520, filed on Apr. 27, 2015, now Pat. No. 10,876,094, which is a continuation of application No. 13/508,991, filed as application No. PCT/IL2010/000937 on Nov. 11, 2010, now Pat. No. 9,018,010.

(60) Provisional application No. 61/272,860, filed on Nov. 12, 2009.

(51) Int. Cl.
C12N 5/071 (2010.01)
C12N 5/0735 (2010.01)
C12N 5/074 (2010.01)

(52) U.S. Cl.
CPC ......... *C12N 5/0602* (2013.01); *C12N 5/0606* (2013.01); *C12N 5/0696* (2013.01); *C12N 2500/36* (2013.01); *C12N 2500/90* (2013.01); *C12N 2500/92* (2013.01); *C12N 2500/98* (2013.01); *C12N 2500/99* (2013.01); *C12N 2501/115* (2013.01); *C12N 2501/15* (2013.01); *C12N 2501/23* (2013.01); *C12N 2506/45* (2013.01)

(58) Field of Classification Search
None
See application file for complete search history.

(56) References Cited

U.S. PATENT DOCUMENTS

| | | | |
|---|---|---|---|
| 6,245,566 B1 | 6/2001 | Gearhart et al. | |
| 6,576,464 B2 | 6/2003 | Gold et al. | |
| 6,671,159 B2 | 12/2003 | Nakamura et al. | |
| 7,250,294 B2 | 7/2007 | Carpenter et al. | |
| 7,413,902 B2 | 8/2008 | Bodnar et al. | |
| 7,413,904 B2 | 8/2008 | Gold et al. | |
| 7,432,104 B2 | 10/2008 | Mitalipova et al. | |
| 7,452,718 B2 | 11/2008 | Gold et al. | |
| 7,455,983 B2 | 11/2008 | Xu et al. | |
| 7,473,555 B2 | 1/2009 | Mandalam et al. | |
| 7,504,257 B2 | 3/2009 | Reubinoff et al. | |
| 7,560,281 B2 | 7/2009 | Carpenter et al. | |
| 7,638,328 B2 | 12/2009 | Eriksson et al. | |
| 7,641,897 B2 | 1/2010 | Weissman et al. | |
| 7,851,167 B2 | 12/2010 | Xu | |
| 7,892,835 B2 | 2/2011 | Akaike et al. | |
| 7,897,389 B2 | 3/2011 | Gold et al. | |
| 7,951,591 B2 | 5/2011 | Robl et al. | |
| 8,067,233 B2 | 11/2011 | Totey et al. | |
| 8,252,585 B2 | 8/2012 | Carpenter et al. | |
| 8,252,586 B2 | 8/2012 | Carpenter | |
| 8,318,486 B2 | 11/2012 | Amit et al. | |
| 8,372,642 B2 | 2/2013 | Rajesh et al. | |
| 8,415,155 B2 | 4/2013 | Stankewicz et al. | |
| 8,445,273 B2 | 5/2013 | Green et al. | |
| 8,470,600 B2 | 6/2013 | Duch et al. | |
| 8,535,944 B2 | 9/2013 | Bamdad | |
| 8,563,311 B2 | 10/2013 | Amit et al. | |
| 8,597,947 B2 | 12/2013 | Reubinoff | |

(Continued)

FOREIGN PATENT DOCUMENTS

| | | |
|---|---|---|
| AU | 2000072431 | 5/2001 |
| AU | 2001011128 | 7/2001 |

(Continued)

OTHER PUBLICATIONS

Shafa et al., Journal of Tissue Engineering and Regenerative Medicine 2012; 6: 462-472, published online Jul. 14, 2011 (Year: 2011).*
Amit et al., Biology of Reproduction, vol. 70, Issue 3, Mar. 1, 2004, pp. 837-845 (Year: 2004).*
Fischer et al., Nature Biotechnology, vol. 15, Feb. 1997, pp. 142-145 (Year: 1997).*
Viswanathan et al., Stem Cells 2002;20:119-138 (Year: 2002).*
R&D Systems, Recombinant Human IL-6/IL-6R Complex Chimera Nov. 6, 2020, 1 page, retrieved from the internet: https://www.rndsystems.com/products/recombinant-human-il-6-il-6r-alpha-protein-chimera_8954-sr (Year: 2020).*
Totonchi et al., Int. J. Dev. Biol. 54: 877-886 (2010), (Year: 2009).*
AMIT SEQ ID No. 31 WO 2008/015682 (Year: 2008).*

(Continued)

Primary Examiner — Evelyn Y Pyla

(57) ABSTRACT

Provided are novel serum-free culture media which comprise basic fibroblast growth factor (bFGF), transforming growth factor beta-3 and ascorbic acid at a concentration of at least about 50 microgram/ml; ascorbic acid at a concentration range of about 400-600 microgram/ml, bFGF at a concentration range of about 50-200 ng/ml, xeno-free serum replacement and a lipid mixture; the IL6RIL6 chimera at a concentration range of about 50-200 picogram per milliliter (pg/ml); or leukemia inhibitory factor (LIF) at a concentration of at least 2000 units/ml; cell cultures comprising same with pluripotent stem cells such as human embryonic stem cells and induced pluripotent stem (iPS) cells, and methods of using same for expanding pluripotent stem cells in an undifferentiated state using two-dimensional or three-dimensional culture systems; and methods of expanding iPS cells in a suspension culture devoid of substrate adherence and cell encapsulation.

Figure 1A:
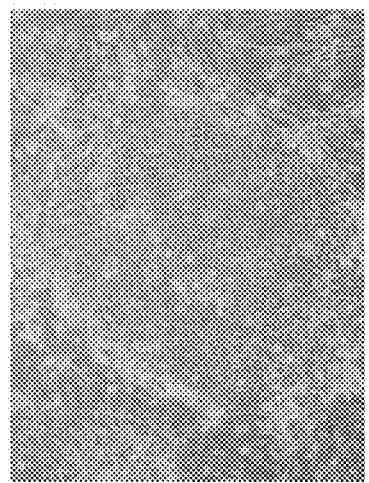

21 Claims, 6 Drawing Sheets
(6 of 6 Drawing Sheet(s) Filed in Color)
Specification includes a Sequence Listing.

(56) References Cited

U.S. PATENT DOCUMENTS

| | | |
|---|---|---|
| 8,623,650 B2 | 1/2014 | Robins et al. |
| 8,628,963 B2 | 1/2014 | Cho et al. |
| 8,633,025 B2 | 1/2014 | Vanderhaeghen et al. |
| 8,637,311 B2 | 1/2014 | Mandalam et al. |
| 8,697,444 B2 | 4/2014 | Schoonjans |
| 8,703,488 B2 | 4/2014 | Impola et al. |
| 8,722,405 B2 | 5/2014 | Tryggvason et al. |
| 9,040,297 B2 | 5/2015 | Amit et al. |
| 9,404,079 B2 | 8/2016 | Amit et al. |
| 9,834,749 B2 | 12/2017 | Amit et al. |
| 10,214,722 B2 | 2/2019 | Amit |
| 10,385,312 B2 | 8/2019 | Amit |
| 10,968,427 B2 | 4/2021 | Amit et al. |
| 11,959,098 B2 | 4/2024 | Amit et al. |
| 12,060,575 B2 | 8/2024 | Amit et al. |
| 2002/0127715 A1 | 9/2002 | Benvenisty et al. |
| 2002/0168763 A1 | 11/2002 | Yan et al. |
| 2003/0064503 A1 | 4/2003 | Abuljadayel |
| 2003/0153082 A1 | 8/2003 | Bhatia |
| 2003/0166272 A1 | 9/2003 | Abujadayel |
| 2003/0211603 A1 | 11/2003 | Earp et al. |
| 2003/0224411 A1 | 12/2003 | Stanton et al. |
| 2004/0009593 A1 | 1/2004 | Keirstead et al. |
| 2004/0014211 A1 | 1/2004 | Ogle et al. |
| 2004/0110286 A1 | 6/2004 | Bhatia |
| 2004/0180347 A1 | 9/2004 | Stanton et al. |
| 2004/0191901 A1 | 9/2004 | Assady et al. |
| 2004/0229350 A1 | 11/2004 | Strelchenko et al. |
| 2005/0032207 A1 | 2/2005 | Wobus et al. |
| 2005/0054093 A1 | 3/2005 | Haas |
| 2005/0095703 A1 | 5/2005 | Semb et al. |
| 2005/0095708 A1 | 5/2005 | Pera et al. |
| 2005/0101014 A1 | 5/2005 | Keirstead et al. |
| 2005/0118713 A1 | 6/2005 | Strelchenko et al. |
| 2005/0153444 A1 | 7/2005 | Mandelam et al. |
| 2005/0153445 A1 | 7/2005 | Mandalam et al. |
| 2005/0164383 A1 | 7/2005 | Reubinoff et al. |
| 2005/0210537 A1 | 9/2005 | Dominko et al. |
| 2005/0214938 A1 | 9/2005 | Gold et al. |
| 2005/0227352 A1 | 10/2005 | Xie |
| 2005/0227353 A1 | 10/2005 | Mummery |
| 2005/0233446 A1 | 10/2005 | Parsons et al. |
| 2005/0260591 A1 | 11/2005 | Ward et al. |
| 2006/0030040 A1 | 2/2006 | Yang et al. |
| 2006/0057720 A1 | 3/2006 | Xu et al. |
| 2006/0063253 A1 | 3/2006 | Maciag et al. |
| 2006/0134636 A1 | 6/2006 | Stanton et al. |
| 2006/0182724 A1 | 8/2006 | Riordan |
| 2006/0223179 A1 | 10/2006 | Thomson et al. |
| 2006/0252150 A1 | 11/2006 | Cheng |
| 2006/0286544 A1 | 12/2006 | Mandal et al. |
| 2007/0053890 A1 | 3/2007 | Rosic-Kablar et al. |
| 2007/0111306 A1 | 5/2007 | Salli et al. |
| 2007/0155013 A1 | 7/2007 | Akaike et al. |
| 2007/0231898 A1 | 10/2007 | Keirstead et al. |
| 2007/0249044 A1 | 10/2007 | Desai et al. |
| 2007/0264713 A1 | 11/2007 | Terstegge et al. |
| 2007/0280989 A1 | 12/2007 | Shahar et al. |
| 2007/0298453 A1 | 12/2007 | Murdoch et al. |
| 2008/0070303 A1 | 3/2008 | West et al. |
| 2008/0076176 A1 | 3/2008 | Dominko et al. |
| 2008/0171385 A1 | 7/2008 | Bergendahl et al. |
| 2008/0182328 A1 | 7/2008 | Snyder et al. |
| 2008/0193421 A1 | 8/2008 | Kruse et al. |
| 2008/0241919 A1 | 10/2008 | Parsons et al. |
| 2008/0274125 A1 | 11/2008 | Guehenneux |
| 2008/0311607 A1 | 12/2008 | Geng et al. |
| 2009/0029461 A1 | 1/2009 | Choo et al. |
| 2009/0029462 A1 | 1/2009 | Beardsley et al. |
| 2009/0104695 A1 | 4/2009 | Shushan et al. |
| 2009/0136559 A1 | 5/2009 | Athanasiou et al. |
| 2009/0148876 A1 | 6/2009 | Dodge |
| 2009/0155218 A1 | 6/2009 | Hayek et al. |
| 2009/0191159 A1 | 7/2009 | Sakurada et al. |
| 2009/0291496 A1 | 11/2009 | Racey et al. |
| 2010/0035327 A1 | 2/2010 | Steele et al. |
| 2010/0047906 A1 | 2/2010 | Totey et al. |
| 2010/0068806 A1 | 3/2010 | Laine et al. |
| 2010/0069251 A1 | 3/2010 | Kim et al. |
| 2010/0093091 A1 | 4/2010 | Reubinoff et al. |
| 2010/0120145 A1 | 5/2010 | Brunner et al. |
| 2010/0197013 A1 | 8/2010 | Kamp et al. |
| 2010/0248366 A1 | 9/2010 | Fadeev et al. |
| 2010/0330063 A1 | 12/2010 | Weinstein |
| 2011/0039332 A1 | 2/2011 | Sakurada et al. |
| 2011/0039333 A1 | 2/2011 | Kahn et al. |
| 2011/0045996 A1 | 2/2011 | Yeo et al. |
| 2011/0065103 A1 | 3/2011 | Sahin et al. |
| 2011/0171183 A1 | 7/2011 | Choo et al. |
| 2011/0300114 A1 | 12/2011 | Priller et al. |
| 2011/0311977 A1 | 12/2011 | Mandal et al. |
| 2011/0312090 A1 | 12/2011 | Meyer et al. |
| 2012/0021513 A1 | 1/2012 | Schulz et al. |
| 2012/0100110 A1 | 4/2012 | Turovets et al. |
| 2012/0122209 A1 | 5/2012 | Reubinoff et al. |
| 2012/0141432 A1 | 6/2012 | Piganelli et al. |
| 2012/0142103 A1 | 6/2012 | Nishida et al. |
| 2012/0148537 A1 | 6/2012 | Chan et al. |
| 2012/0148632 A1 | 6/2012 | Chan et al. |
| 2012/0225480 A1 | 9/2012 | Amit et al. |
| 2012/0282691 A1 | 11/2012 | Qian et al. |
| 2012/0322146 A1 | 12/2012 | Carpenter et al. |
| 2013/0059377 A1 | 3/2013 | Muotri et al. |
| 2013/0084563 A1 | 4/2013 | Amit et al. |
| 2013/0102023 A1 | 4/2013 | Smith et al. |
| 2013/0115695 A1 | 5/2013 | Schulz |
| 2013/0130375 A1 | 5/2013 | Rudy-Reil |
| 2013/0149284 A1 | 6/2013 | Malcuit et al. |
| 2013/0189230 A1 | 7/2013 | Schoichet et al. |
| 2013/0236436 A1 | 9/2013 | Zhang et al. |
| 2013/0236961 A1 | 9/2013 | Amit et al. |
| 2013/0252329 A1 | 9/2013 | Amit et al. |
| 2013/0316445 A1 | 11/2013 | Beardsley et al. |
| 2014/0030236 A1 | 1/2014 | Wanjare et al. |
| 2015/0240202 A1 | 8/2015 | Amit et al. |
| 2021/0189331 A1 | 6/2021 | Amit et al. |
| 2022/0333066 A1 | 10/2022 | Amit et al. |
| 2023/0060616 A1 | 3/2023 | Amit et al. |

FOREIGN PATENT DOCUMENTS

| | | |
|---|---|---|
| AU | 2002237681 | 6/2002 |
| AU | 2002313670 | 1/2003 |
| AU | 2009213101 | 10/2009 |
| AU | 2014201623 | 5/2014 |
| CA | 2248555 | 9/1997 |
| CA | 2409698 | 11/2001 |
| CA | 2434760 | 5/2002 |
| CA | 2447015 | 11/2002 |
| CA | 2451486 | 1/2003 |
| CA | 2453068 | 1/2003 |
| CA | 2453438 | 1/2003 |
| CA | 2468335 | 6/2003 |
| CA | 2469483 | 6/2003 |
| CA | 2470539 | 6/2003 |
| CA | 2508880 | 7/2004 |
| CA | 2524611 | 11/2004 |
| CA | 2559854 | 9/2005 |
| CA | 2573437 | 2/2006 |
| CA | 2713754 | 8/2009 |
| CA | 2806127 | 1/2012 |
| CA | 2640644 | 11/2013 |
| EP | 1809739 | 7/2007 |
| EP | 1881062 | 1/2008 |
| EP | 2267116 | 12/2010 |
| GB | 2379447 | 3/2003 |
| GB | 2392674 | 3/2004 |
| GB | 2393733 | 4/2004 |
| GB | 2393734 | 4/2004 |
| GB | 2394723 | 5/2004 |
| GB | 2427873 | 1/2007 |
| GB | 2431165 | 4/2007 |
| HK | 1075673 | 2/2009 |
| HK | 1103106 | 7/2009 |

(56) References Cited

FOREIGN PATENT DOCUMENTS

| | | |
|---|---|---|
| HK | 1055765 | 9/2010 |
| IL | 141742 | 3/2002 |
| IL | 152741 | 6/2003 |
| IL | 159324 | 6/2004 |
| IL | 159578 | 6/2004 |
| IL | 159580 | 6/2004 |
| IL | 160403 | 7/2004 |
| IL | 177324 | 12/2006 |
| IL | 178006 | 12/2006 |
| IL | 180447 | 6/2007 |
| JP | 08-308561 | 11/1996 |
| JP | 2003-530880 | 10/2003 |
| JP | 2003-533184 | 11/2003 |
| JP | 2006-129734 | 5/2006 |
| JP | 2007-029009 | 2/2007 |
| JP | 2007-228815 | 9/2007 |
| JP | 2008-518585 | 6/2008 |
| JP | 2008-546410 | 12/2008 |
| JP | 2009-528034 | 8/2009 |
| JP | 04-666567 | 1/2011 |
| JP | 2013-510567 | 3/2013 |
| WO | WO 97/33995 | 9/1997 |
| WO | WO 99/01763 | 1/1999 |
| WO | WO 99/20741 | 4/1999 |
| WO | WO 01/75135 | 10/2001 |
| WO | WO 01/81551 | 11/2001 |
| WO | WO 02/31123 | 4/2002 |
| WO | WO 03/000868 | 1/2003 |
| WO | WO 03/004605 | 1/2003 |
| WO | WO 03/006950 | 1/2003 |
| WO | WO 03/020920 | 3/2003 |
| WO | WO 03/050249 | 6/2003 |
| WO | WO 2005/053601 | 6/2005 |
| WO | WO 2005/065354 | 7/2005 |
| WO | WO 2006/020889 | 2/2006 |
| WO | WO 2006/029198 | 3/2006 |
| WO | WO 2007/002086 | 1/2007 |
| WO | WO 2007/002210 | 1/2007 |
| WO | WO 2007/012009 | 1/2007 |
| WO | WO 2007/026353 | 3/2007 |
| WO | WO 2007/069666 | 6/2007 |
| WO | WO 2007/101130 | 9/2007 |
| WO | WO 2007/122233 | 11/2007 |
| WO | WO 2008/007082 | 1/2008 |
| WO | WO 2008/015682 | 2/2008 |
| WO | WO 2008/054819 | 5/2008 |
| WO | WO 2008/148105 | 12/2008 |
| WO | WO 2008/148938 | 12/2008 |
| WO | WO 2009/097411 | 8/2009 |
| WO | WO 2010/144059 | 12/2010 |
| WO | WO 2011/058558 | 5/2011 |
| WO | WO 2011/075686 | 6/2011 |
| WO | WO 2011/110886 | 9/2011 |
| WO | WO 2011/114237 | 9/2011 |

OTHER PUBLICATIONS

Supplementary European Search Report and the European Search Opinion Dated Mar. 8, 2023 From the European Patent Office Re. Application No. 22185625.5. (9 Pages).
Notice of Reason for Rejection Dated Sep. 3, 2021 From the Japan Patent Office Re. Application No. 2019-188087 and Its Translation Into English. (8 Pages).
Notice of Reason(s) for Rejection Dated Mar. 24, 2023 From the Japan Patent Office Re. Application No. 2022-59325 and Its Translation Into English. (9 pages).
Eiselleova et al. "A Complex Role for FGF-2 in Self-Renewal, Survival, and Adhesion of Human Embryonic Stem Cells", Stem Cells, 27: 1847-1857, May 14, 2009.
Requisition by the Examiner Dated May 16, 2023 From the Innovation, Science and Economic Development Canada, Canadian Intellectual Property Office Re. Application No. 3,080,762. (3 pages).
Advisory Action Before the Filing of An Appeal Brief Dated Mar. 24, 2017 From the US Patent and Trademark Office Re. U.S. Appl. No. 14/696,520. (4 pages).
Communication Pursuant to Article 94(3) EPC Dated Aug. 9, 2018 From the European Patent Office Re. Application No. 10829622.9. (5 Pages).
Communication Pursuant to Article 94(3) EPC Dated Apr. 10, 2014 From the European Patent Office Re. Application No. 10829622.9.
Communication Pursuant to Article 94(3) EPC Dated Feb. 11, 2015 From the European Patent Office Re. Application No. 10829622.9.
Communication Pursuant to Article 94(3) EPC Dated Jun. 13, 2016 From the European Patent Office Re. Application No. 10829622.9.
Communication Pursuant to Article 94(3) EPC Dated Sep. 19, 2014 From the European Patent Office Re. Application No. 10829622.9.
Communication Pursuant to Article 94(3) EPC Dated Sep. 25, 2015 From the European Patent Office Re. Application No. 10829622.9.
Communication Pursuant to Article 94(3) EPC Dated May 26, 2017 From the European Patent Office Re. Application No. 10829622.9. (5 Pages).
Communication Pursuant to Article 94(3) EPC Dated Nov. 27, 2013 From the European Patent Office Re. Application No. 10829622.9.
Communication Pursuant to Article 94(3) EPC Dated Oct. 30, 2020 From the European Patent Office Re. Application No. 19210132.7. (7 Pages).
European Search Report and the European Search Opinion Dated Jan. 21, 2020 From the European Patent Office Re. Application No. 19210132.7. (9 Pages).
International Preliminary Report on Patentability Dated May 24, 2012 From the International Bureau of WIPO Re. Application No. PCT/IL2010/00937.
International Search Report and the Written Opinion Dated Jul. 27, 2011 From the International Searching Authority Re. Application No. PCT/IL2010/00937.
Invitation to Pay Additional Fees Dated May 2, 2011 From the International Searching Authority Re. Application No. PCT/IL2010/00937.
Notice of Allowance Dated Sep. 2, 2020 from the US Patent and Trademark Office Re. U.S. Appl. No. 14/696,520. (13 pages).
Notice of Reason for Rejection Dated Jun. 7, 2019 From the Japan Patent Office Re. Application No. 2017-152419 and Its Translation Into English. (4 Pages).
Notice of Reason for Rejection Dated Sep. 15, 2017 From the Japan Patent Office Re. Application No. 2012-538468 and Its Translation Into English. (10 Pages).
Notice of Reason for Rejection Dated Aug. 16, 2016 From the Japan Patent Office Re. Application No. 2015-207773 and Its Translation Into English.
Notice of Reason for Rejection Dated Feb. 17, 2017 From the Japanese Patent Office Re. Application No. 2012-538468. (16 Pages).
Notice of Reason for Rejection Dated Oct. 19, 2018 From the Japan Patent Office Re. Application No. 2017-152419 and Its Translation Into English. (7 Pages).
Notice of Reason for Rejection Dated Jan. 30, 2015 From the Japanese Patent Office Re. Application No. 2012-538468 and Its Translation Into English.
Office Action Dated Nov. 13, 2017 From the Israel Patent Office Re. Application No. 252607 and Its Translation Into English. (9 Pages).
Office Action Dated Jan. 15, 2015 From the Israel Patent Office Re. Application No. 219736.
Official Action Dated Jul. 1, 2016 From the US Patent and Trademark Office Re. U.S. Appl. No. 14/696,520.
Official Action Dated Jun. 5, 2018 From the US Patent and Trademark Office Re. U.S. Appl. No. 14/696,520. (19 pages).
Official Action Dated Oct. 15, 2018 From the US Patent and Trademark Office Re. U.S. Appl. No. 14/696,520. (27 pages).
Official Action Dated Jan. 24, 2014 From the US Patent and Trademark Office Re. U.S. Appl. No. 13/508,991.
Official Action Dated May 24, 2019 From the US Patent and Trademark Office Re. U.S. Appl. No. 14/696,520. (34 pages).
Official Action Dated Nov. 27, 2017 From the US Patent and Trademark Office Re. U.S. Appl. No. 14/696,520. (18 pages).

(56) References Cited

OTHER PUBLICATIONS

Official Action Dated Dec. 29, 2016 From the US Patent and Trademark Office Re. U.S. Appl. No. 14/696,520. (17 pages).
Decision of Rejection Dated Jun. 23, 2015 From the Japanese Patent Office Re. Application No. 2012-538468 and Its Translation Into English.
Decision of Rejection Dated Apr. 28, 2017 From the Japan Patent Office Re. Application No. 2015-207773 and Its Translation Into English. (12 Pages).
Requisition by the Examiner Dated Nov. 2, 2016 From the Canadian Intellectual Property Office Re. Application No. 2,783,437. (18 Pages).
Requisition by the Examiner Dated Nov. 20, 2017 From the Canadian Intellectual Property Office Re. Application No. 2,783,437. (11 Pages).
Restriction Official Action Dated Aug. 6, 2013 From the US Patent and Trademark Office Re. U.S. Appl. No. 13/508,991.
Second International Search Report and the Written Opinion Dated Aug. 18, 2011 From the International Searching Authority Re. Application No. PCT/IL2010/00937.
Supplementary European Search Report Dated Apr. 19, 2013 From the European Patent Office Re. Application No. 10829622.9.
Translation Dated Feb. 1, 2015 of Office Action Dated Jan. 15, 2015 From the Israel Patent Office Re. Application No. 219736.
Translation of Notice of Reason for Rejection Dated Feb. 17, 2017 From the Japanese Patent Office Re. Application No. 2012-538468. (18 Pages).
Amit et al. "Suspension Culture of Undifferentiated Human Embryonic and Induced Pluripotent Stem Cells", Stem Cell Reviews and Reports, XP055015267, 6(2): 248-259, Apr. 30, 2010.
Cell Signal "Common Pluripotency Markers, Cell Signaling Technology", retrieved from cellsignal.corn, 3 Pages, May 16, 2019.
Hishikawa Xeno-Free ES Cell Culture System, Regenerative Medicine, 5(1): 65-71, 2006. English Abstract.
Ludwig et al. "Derivation of A Human Embryonic Stem Cells in Defined Conditions", Nature Biotechnology, Advance Online Publication, p. 1-3, 2006.
Ludwig et al. "Table S1. Complete Formulation for TeSR1 Medium", Nature Biotechnology, Supplemental, 1 P., 2006.
Meissner et al. "Direct Reprogramming of Genetically Unmodified Fibroblasts into Pluripotent Stem Cells", Nature Biotechnology, 25: 1177-1181, 2007.
Okita et al. "Generation of Germline-Competent Induced Pluripotent Stem Cells", Nature 448: 313-318, 2007.
Takahashi et al. "Induction of Pluripotent Stem Cells From Adult Human Fibroblasts by Defined Factors", Cell, 131(5): 861-872, Nov. 30, 2007.
Takahashi et al. "Induction of Pluripotent Stem Cells From Mouse Embryonic and Adult Fibroblast Cultures by Defined Factors", Cell, 126: 663-676, 2006.
Thomson et al. "Embryonic Stem Cell Lines Derived From Human Blastocysts", Science, 282(5391): 1145-1147, Nov. 6, 1998.
Yu et al. "Induced Pluripotent Stem Cell Lines Derived from Human Somatic Cells", Science, 318: 1917-1920, 2007. and supporting online material.
Requisition by the Examiner Dated Nov. 17, 2023 From the Innovation, Science and Economic Development Canada, Canadian Intellectual Property Office Re. Application No. 3,174,901. (3 Pages).
Official Action Dated Apr. 23, 2024 from the US Patent and Trademark Office Re. U.S. Appl. No. 17/841,700. (111 pages).
Communication Pursuant to Article 94(3) EPC Dated Mar. 26, 2024 From the European Patent Office Re. Application No. 22185625.5 (8 Pages).
Official Action Dated Nov. 5, 2024 from the US Patent and Trademark Office Re. U.S. Appl. No. 17/841,700. (36 pages).
Levenstein et al. "Basic Fibroblast Growth Factor Support of Human Embryonic Stem Cell Self-Renewal", Stem Cells, 24(3): 568-574, Mar. 2006.
Totonchi et al. "Feeder- and Serum-free Establishment and Expansion of Human Induced Pluripotent Stem Cells", The International Journal of Developmental Biology, 54: 877-886 (2010), Oct. 2, 2009.
Official Action Dated May 8, 2025 from the US Patent and Trademark Office Re. U.S. Appl. No. 17/841,700. (37 Pages).
Requisition by the Examiner Dated May 22, 2025 From the Innovation, Science and Economic Development Canada, Canadian Intellectual Property Office Re. Application No. 3,174,901. (3 Pages).

\* cited by examiner

CULTURE MEDIA, CELL CULTURES AND METHODS OF CULTURING PLURIPOTENT STEM CELLS IN AN UNDIFFERENTIATED STATE

RELATED APPLICATIONS

This application is a division of U.S. patent application Ser. No. 14/696,520 filed on Apr. 27, 2015, which is a continuation of U.S. patent application Ser. No. 13/508,991 filed on May 10, 2012, now U.S. Pat. No. 9,018,010, which is a National Phase of PCT Patent Application No. PCT/IL2010/000937 having International Filing Date of Nov. 11, 2010, which claims the benefit of priority of U.S. Provisional Patent Application No. 61/272,860 filed on Nov. 12, 2009. The contents of the above applications are all incorporated by reference as if fully set forth herein in their entirety.

SEQUENCE LISTING STATEMENT

The ASCII file, entitled 84991SequenceListing.txt, created on Nov. 11, 2020, comprising 35,204 bytes, submitted concurrently with the filing of this application is incorporated herein by reference.

FIELD AND BACKGROUND OF THE INVENTION

The present invention, in some embodiments thereof, relates to xeno-free culture media which can be used to maintain stem cells in a pluripotent and undifferentiated state, and in some embodiments to defined culture media, cell cultures comprising same and methods using same for culturing pluripotent stem cells in a suspension culture.

The exceptional differentiation potential of human embryonic stem cells (hESCs) underlines them as one of the best models to study early human development, lineage commitment, differentiation processes and to be used for industrial purposes and cell-based therapy.

Induced pluripotent (iPS) cells are somatic cells which are re-programmed to ESC-like cells capable of differentiation into representative tissues of the three embryonic germ layers both in vitro and in vivo. Mouse or human iPS cells were generated by over expression of four transcription factors, c-Myc, Oct4, Klf4 and Sox2 in somatic cells. The iPS cells were shown to form the same colony morphology as ESCs and to express some typical ESCs markers such as Myb, Kit, Gdf3 and Zic3, but less prominently markers such as Dnmt3a, Dnmt3b, Utf1, Tcl1 and the LIF receptor gene, confirming that iPS cells are similar but not identical to ES cells [Takahashi and Yamanaka, 2006; Takahashi et al, 2007; Meissner et al, 2007; Okita et al, 2007]. Yu Junying et al. (Science 318:1917-1920, 2007) found a common gene expression pattern to fibroblasts-derived iPS cells and hESCs.

Further studies revealed that iPS cells could be obtained by transforming somatic cells with Oct4, Sox2, Nanog and Lin28 while omitting the use of the oncogene C-Myc [Yu et al, 2007; Nakagawa et al, 2008]. Improvements of iPS cells derivation methods include the use of plasmids instead of viral vectors or derivation without any integration to the genome, which might simplify the future use of iPS cells for clinical applications [Yu J, et al., Science. 2009, 324: 797-801].

The currently available iPS cells are those derived from embryonic fibroblasts [Takahashi and Yamanaka, 2006; Meissner et al, 2007], fibroblasts formed from hESCs [Park et al, 2008], Fetal fibroblasts [Yu et al, 2007; Park et al, 2008], foreskin fibroblast [Yu et al, 2007; Park et al, 2008], adult dermal and skin tissues [Hanna et al, 2007; Lowry et al, 2008], b-lymphocytes [Hanna et al 2007] and adult liver and stomach cells [Aoi et al, 2008].

Similarly to hESCs, iPS cells are traditionally cultured with a supportive layer in 2D culture, which allows their continuous growth in the undifferentiated state. For example, iPS cells were cultured on feeder-layers consisting of inactivated mouse embryonic fibroblasts (MEF) or foreskin fibroblasts [Takahashi and Yamanaka 2006, Meisnner at al 2007] in the presence of a medium supplemented with fetal bovine serum (FBS). Further improvements of the culturing methods include culturing iPS cells on MEF feeder layers in the presence of a more defined culture medium containing serum replacement and 10 ng/ml of basic fibroblasts growth factor (bFGF) (Park et al., 2008). However, for clinical applications (e.g., cell-based therapy) or industrial purposes, the iPS cells should be cultured in a defined, xeno-free (e.g., animal-free) and a scalable culture system with controlled processes.

PCT Publication No. WO2007/026353 discloses a well-defined, xeno-free culture media which comprise a TGF-beta isoform or the chimera formed between IL6 and the soluble IL6 receptor (IL6RIL6) for maintaining human embryonic stem cells, in an undifferentiated state in a two-dimensional culture system.

U.S. Patent Application No. 20050233446 discloses a defined medium which comprises bFGF, insulin and ascorbic acid for maintaining hESCs when cultured on Matrigel™ in an undifferentiated state.

Ludwig T E., et al., 2006 (Nature Biotechnology, 24: 185-7) discloses the TeSR1 defined medium for culturing hESCs on a matrix composed of Collagen IV, fibronectin, laminin and virtonectin.

U.S. Patent Application No. 20090029462 discloses methods of expanding pluripotent stem cells in suspension using microcarriers or cell encapsulation.

PCT Publication No. WO/2008/015682 discloses a method of expanding and maintaining human embryonic stem cells in a suspension culture under culturing conditions devoid of substrate adherence.

U.S. Patent Application No. 20070155013 discloses a method of growing pluripotent stem cells in suspension using a carrier which adheres to the pluripotent stem cells.

U.S. Patent Application No. 20080241919 (Parsons et al.) discloses a method of culturing pluripotent stem cells in a suspension culture in a medium which comprises bFGF, insulin and ascorbic acid in a cell culture vessel that includes a cell-free matrix.

U.S. Patent Application No. 20080159994 (Mantalaris et al.) discloses a method of culturing pluripotent ES cells encapsulated within alginate beads in a three-dimensional culture in a medium which comprises serum replacement and bFGF.

U.S. Patent Application No. 20070264713 discloses a method of culturing undifferentiated stem cells in suspension on microcarriers in vessels using a conditioned medium.

SUMMARY OF THE INVENTION

According to an aspect of some embodiments of the present invention there is provided a culture medium being serum-free and xeno-free comprising basic fibroblast growth factor (bFGF), transforming growth factor beta-3 (TGFβ3)

and ascorbic acid, wherein a concentration of the ascorbic acid in the culture medium is at least about 50 μg/ml and wherein the culture medium is capable of maintaining pluripotent stem cells in an undifferentiated state in the absence of feeder cell support.

According to an aspect of some embodiments of the present invention there is provided a culture medium being serum-free and xeno-free comprising ascorbic acid at a concentration range of about 400-600 μg/ml, basic fibroblast growth factor (bFGF) at a concentration range of about 50-200 ng/ml, xeno-free serum replacement and a lipid mixture, wherein the culture medium is capable of maintaining pluripotent stem cells in an undifferentiated state in the absence of feeder cell support.

According to an aspect of some embodiments of the present invention there is provided a culture medium being serum-free comprising an IL6RIL6 chimera at a concentration range of about 50-200 picogram per milliliter (pg/ml), wherein the culture medium is capable of maintaining pluripotent stem cells in an undifferentiated state in the absence of feeder cell support.

According to an aspect of some embodiments of the present invention there is provided a culture medium being serum-free comprising a leukemia inhibitory factor (LIF) at a concentration of at least 2000 units/ml, wherein the culture medium is capable of maintaining pluripotent stem cells in an undifferentiated state in the absence of feeder cell support.

According to an aspect of some embodiments of the present invention there is provided a culture medium comprising basic fibroblast growth factor (bFGF) at a concentration range of about 50-200 ng/ml and serum replacement, wherein the culture medium is capable of maintaining pluripotent stem cells in an undifferentiated state in a suspension culture.

According to an aspect of some embodiments of the present invention there is provided a culture medium consisting of a basic medium, ascorbic acid at a concentration range of about 50 μg/ml to about 500 μg/ml, bFGF at a concentration range between about 2 ng/ml to about 20 ng/ml, L-glutamine, and serum replacement.

According to an aspect of some embodiments of the present invention there is provided a culture medium consisting of a basic medium, ascorbic acid at a concentration range of about 50 μg/ml to about 500 μg/ml, bFGF at a concentration range between about 2 ng/ml to about 20 ng/ml, L-glutamine, serum replacement and a lipid mixture.

According to an aspect of some embodiments of the present invention there is provided a cell culture comprising a pluripotent stem cell and the culture medium of the invention.

According to an aspect of some embodiments of the present invention there is provided a method of deriving an embryonic stem cell line, comprising: (a) obtaining an embryonic stem cell from a pre-implantation stage blastocyst, post-implantation stage blastocyst and/or a genital tissue of a fetus; and (b) culturing the embryonic stem cell in the culture medium of the invention; thereby deriving the embryonic stem cell line.

According to an aspect of some embodiments of the present invention there is provided a method of deriving an induced pluripotent stem cell line, comprising: (a) inducing a somatic cell to a pluripotent stem cell; and (b) culturing the pluripotent stem cell in the culture medium of the invention; thereby deriving the induced pluripotent stem cell line.

According to an aspect of some embodiments of the present invention there is provided a method of expanding and maintaining pluripotent stem cells in an undifferentiated state, the method comprising culturing the pluripotent stem cells in the culture medium of the invention, thereby expanding and maintaining the pluripotent stem cells in the undifferentiated state.

According to an aspect of some embodiments of the present invention there is provided a method of expanding and maintaining pluripotent stem cells in an undifferentiated state, the method comprising culturing the pluripotent stem cells in a culture medium being serum-free, feeder-free, matrix-free and protein carrier-free and comprising basic fibroblast growth factor (bFGF) at a concentration range of about 50-200 ng/ml, wherein the culture medium is capable of maintaining pluripotent stem cells in an undifferentiated state.

According to an aspect of some embodiments of the present invention there is provided a method of expanding pluripotent stem cells and maintaining the pluripotent stem cells in an undifferentiated state, the method comprising culturing the pluripotent stem cells on a feeder cell layer in a serum-free and xeno-free culture medium, the culture medium comprises basic fibroblast growth factor (bFGF) transforming growth factor beta-3 (TGFβ3) and ascorbic acid, wherein a concentration of the ascorbic acid in the culture medium is at least 50 μg/ml and wherein the culture medium is capable of maintaining pluripotent stem cells in an undifferentiated state, thereby expanding and maintaining the stem cells in the undifferentiated state.

According to an aspect of some embodiments of the present invention there is provided a method of expanding pluripotent stem cells and maintaining the pluripotent stem cells in an undifferentiated state, the method comprising culturing the pluripotent stem cells on a feeder cell layer in a serum-free and xeno-free culture medium, the culture medium comprises ascorbic acid at a concentration range of about 400-600 μg/ml, basic fibroblast growth factor (bFGF) at a concentration range of about 50-200 ng/ml, xeno-free serum replacement and a lipid mixture, wherein the culture medium is capable of maintaining pluripotent stem cells in an undifferentiated state, thereby expanding and maintaining the stem cells in the undifferentiated state.

According to an aspect of some embodiments of the present invention there is provided a method of expanding induced pluripotent stem (iPS) cells and maintaining the iPS cells in an undifferentiated state, the method comprising culturing the iPS cells in a suspension culture under culturing conditions devoid of substrate adherence and devoid of cell encapsulation and which allow expansion of the iPS cells in the undifferentiated state, thereby expanding and maintaining the iPS cells in the undifferentiated state.

According to an aspect of some embodiments of the present invention there is provided a method of generating lineage-specific cells from pluripotent stem cells, the method comprising: (a) culturing the pluripotent stem cells according to the method of the invention, to thereby obtain expanded, undifferentiated stem cells; (b) subjecting the expanded, undifferentiated stem cells to culturing conditions suitable for differentiating and/or expanding lineage specific cells; thereby generating the lineage-specific cells from the pluripotent stem cells.

According to an aspect of some embodiments of the present invention there is provided a method of generating embryoid bodies from pluripotent stem cells, the method comprising: (a) culturing the pluripotent stem cells according to the method of the invention, to thereby obtain expanded, undifferentiated pluripotent stem cells; and (b) subjecting the expanded, undifferentiated pluripotent stem cells to culturing conditions suitable for differentiating the stem cells to embryoid bodies; thereby generating the embryoid bodies from the pluripotent stem cells.

According to an aspect of some embodiments of the present invention there is provided a method of generating lineage-specific cells from pluripotent stem cells, the method comprising: (a) culturing the pluripotent stem cells according to the method of the invention, to thereby obtain expanded, undifferentiated pluripotent stem cells; (b) subjecting the expanded, undifferentiated pluripotent stem cells to culturing conditions suitable for differentiating the expanded, undifferentiated stem cells to embryoid bodies; and (c) subjecting cells of the embryoid bodies to culturing conditions suitable for differentiating and/or expanding lineage specific cells; thereby generating the lineage-specific cells from the pluripotent stem cells.

According to some embodiments of the invention, the cell culture is feeder cells free.

According to some embodiments of the invention, the culture medium is capable of expanding the pluripotent stem cells in an undifferentiated state when cultured in a suspension culture.

According to some embodiments of the invention, the stem cells are embryonic stem cells.

According to some embodiments of the invention, the stem cells are induced pluripotent stem (iPS) cells.

According to some embodiments of the invention, the embryonic stem cells are human embryonic stem cells.

According to some embodiments of the invention, the induced pluripotent stem cells are human induced pluripotent stem cells.

According to some embodiments of the invention, the culture medium is capable of expanding the pluripotent stem cells in an undifferentiated state.

According to some embodiments of the invention, the culture medium further comprises basic fibroblast growth factor (bFGF).

According to some embodiments of the invention, the culture medium further comprises serum replacement.

According to some embodiments of the invention, a concentration of the TGFβ3 in the culture medium is at least about 0.5 ng/ml.

According to some embodiments of the invention, a concentration of the TGFβ3 in the culture medium is about 2 ng/ml.

According to some embodiments of the invention, a concentration of the bFGF in the culture medium is at least about 5 ng/ml.

According to some embodiments of the invention, a concentration of the bFGF in the culture medium is in the range of about 5 ng/ml to about 200 ng/ml.

According to some embodiments of the invention, a concentration of the ascorbic acid in the culture medium is in the range of about 400 microgram/milliliter (μg/ml) to about 600 μg/ml.

According to some embodiments of the invention, a concentration of the ascorbic acid in the culture medium is about 500 μg/m (microgram/milliliter).

According to some embodiments of the invention, the culturing is effected on a matrix.

According to some embodiments of the invention, the matrix comprises an extracellular matrix.

According to some embodiments of the invention, the extracellular matrix is selected from the group consisting of a fibronectin matrix, a laminin matrix, and a foreskin fibroblast matrix.

According to some embodiments of the invention, the matrix is xeno-free.

According to some embodiments of the invention, the feeder cell layer is xeno-free.

According to some embodiments of the invention, the feeder cell layer comprises foreskin fibroblast cells.

According to some embodiments of the invention, the bFGF is at a concentration range of about 0.1 ng/ml to about 500 ng/ml, the TGFβ3 is at a concentration range of about 0.1 ng/ml to about 20 ng/ml, the ascorbic acid is at a concentration range of about 50 μg/ml to about 5000 μg/ml.

According to some embodiments of the invention, the bFGF is at a concentration range of about 5 ng/ml to about 150 ng/ml, the TGFβ3 is at a concentration range of about 0.5 ng/ml to about 5 ng/ml, the ascorbic acid is at a concentration range of about 400 μg/ml to about 600 μg/ml.

According to some embodiments of the invention, the culture medium further comprising serum replacement.

According to some embodiments of the invention, the serum replacement is xeno free.

According to some embodiments of the invention, the culture medium further comprising a lipid mixture.

According to some embodiments of the invention, the culture medium further comprising sodium bicarbonate at a concentration of about 5% to about 10%.

According to some embodiments of the invention, the lipid mixture is at a concentration of about 1%.

According to some embodiments of the invention, the concentration of the IL6RIL6 chimera is about 100 pg/ml.

According to some embodiments of the invention, the concentration of the LIF is in a range of about 2000-4000 units/ml.

According to some embodiments of the invention, the culturing is effected in a suspension culture.

According to some embodiments of the invention, the culture medium is devoid of TGFβ3.

According to some embodiments of the invention, the culture medium comprises no more than 0.1 ng/ml of TGFβ3.

According to some embodiments of the invention, a culture medium of the suspension culture is serum-free and feeder cell-free.

According to some embodiments of the invention, the culture medium being serum-free and devoid of animal contaminants.

According to some embodiments of the invention, the concentration of said bFGF is about 100 ng/ml.

According to some embodiments of the invention, the culture medium comprises an IL6RIL6 chimera at a concentration range of about 50-200 picograms per milliliter (pg/ml), wherein the culture medium is capable of maintaining the iPS cells in an undifferentiated state in the absence of feeder cell support.

According to some embodiments of the invention, the culture medium comprises leukemia inhibitory factor (LIF) at a concentration of at least 2000 units/ml, wherein the culture medium is capable of maintaining the iPS cells in an undifferentiated state in the absence of feeder cell support.

According to some embodiments of the invention, the culture medium comprises basic fibroblast growth factor (bFGF) at a concentration range of about 50-200 ng/ml.

According to some embodiments of the invention, the culture medium comprises an IL6RIL6 chimera at a concentration range of about 50-200 nanogram per milliliter (ng/ml).

According to some embodiments of the invention, the culture medium further comprises basic fibroblast growth factor (bFGF).

According to some embodiments of the invention, the culture medium is protein carrier-free.

According to some embodiments of the invention, expanding comprises obtaining at least about $8 \times 10^6$ cells from a single pluripotent stem cell following about 1 month.

According to some embodiments of the invention, the pluripotent stem cells cultured in the culture medium exhibits a normal chromosomal karyotype following at least 2 passages.

According to some embodiments of the invention, the pluripotent stem cells exhibits a doubling time of at least 20 hours.

According to some embodiments of the invention, maintaining is for at least 5 passages.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 1B:
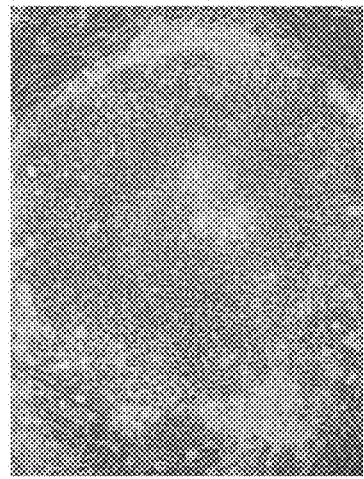
Figure 1C:
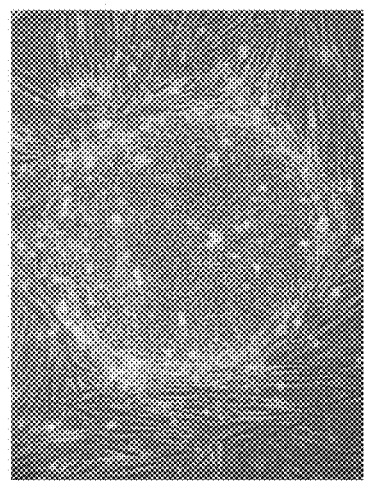

In the drawings:

FIGS. 1A-1C are photographs depicting colony morphology of iPS cells cultured on a xeno-free two-dimensional culture system in the presence of the novel xeno-free (e.g., animal-free, devoid of animal contamination) culture media according to some embodiments of the invention. J1.2-3 were cultured with human foreskin fibroblast (HFF) supportive layers while using the following animal-serum free culture medium: FIG. 1A—medium HA70 for 6 passages; FIG. 1B—medium HA40/4 for 6 passages; and FIG. 1C—medium D2 for 16 passages.

Figure 2A:
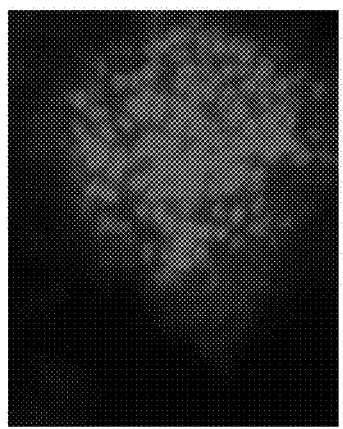
Figure 2B:
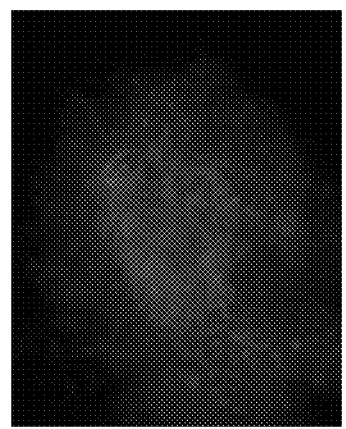
Figure 2C:
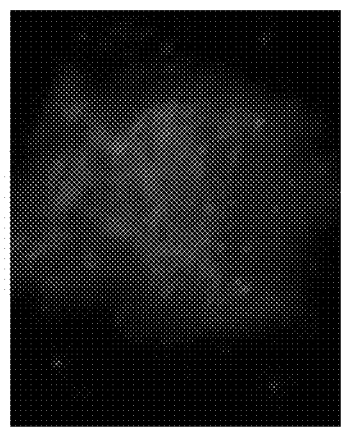

FIGS. 2A-2C are photographs depicting immuno-fluorescence staining of iPS cells with markers of pluripotency. J1.2-3 and iF4 iPS cells were cultured on a xeno-free two-dimensional culture system (HFF) in the presence of the animal-serum free culture medium HA77 for at least 10 passages and were then stained with the following markers of undifferentiated markers: FIG. 2A—J1.2-3 iPS cells stained with Oct4; FIG. 2B—iF4 iPS cells stained with SSEA4; and FIG. 2C—iF4 iPS cells stained with TRA-1-81.

Figure 3C:
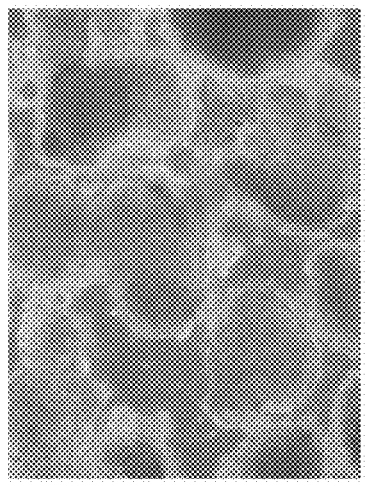
Figure 3B:
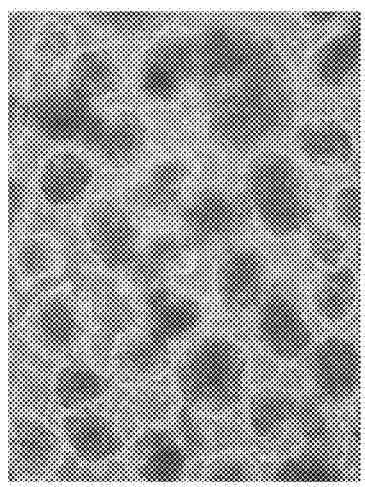
Figure 3A:
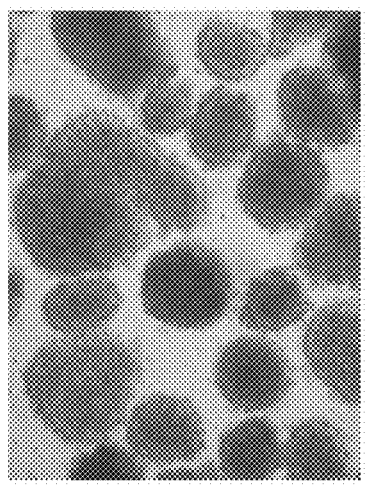

FIGS. 3A-3C are photographs depicting the morphology of the J1.2-3 iPS cell line from HFF when cultured in suspension in the following xeno-free culture media for the indicated passages. FIG. 3A—J1.2-3 iPS cells cultured in the yFL3 medium for 16 passages; FIG. 3B—J1.2-3 iPS cells cultured in the CM100F medium for 13 passages; FIG. 3C—J1.2-3 iPS cells cultured in the yF100 medium for 8 passages. Note that while cultured in suspension the iPS cells create sphere like structure containing undifferentiated cells.

Figure 4:
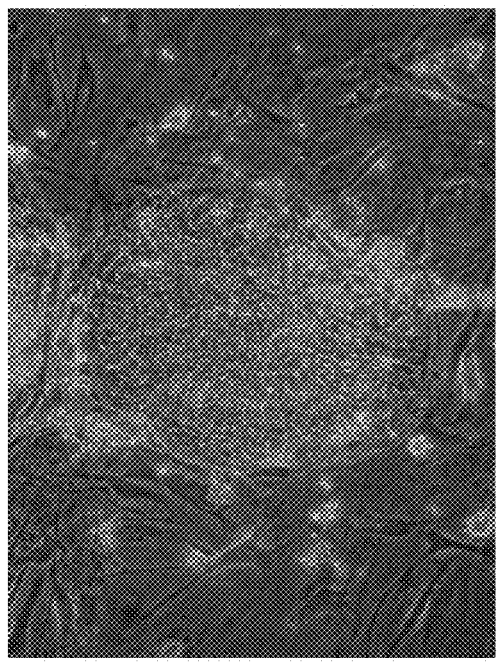

FIG. 4 is a photograph depicting the morphology of the J1.2-3 iPS cells when cultured on mouse embryonic fibroblasts (MEF) after an extended culturing period in a suspension culture. J1.2-3 cells were cultured for 37 passages in suspension in the CM100F medium, following which they were re-cultured with MEFs, and form typical iPS colony morphology 24 hours post their culture with MEFs.

Figure 5A:
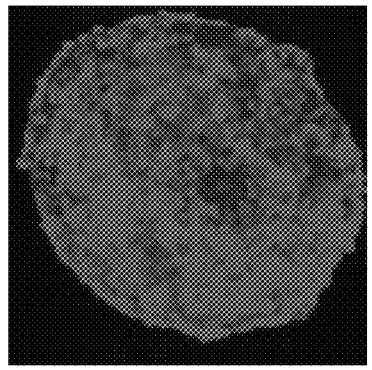
Figure 5B:
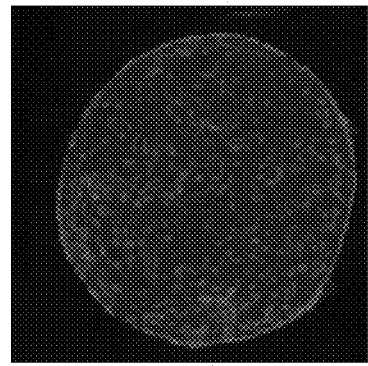
Figure 5C:
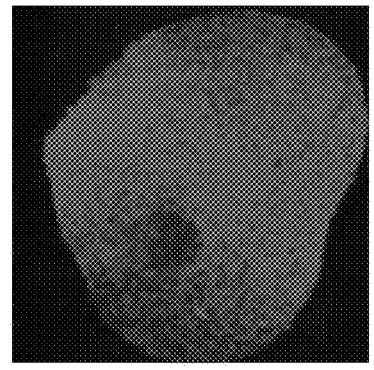

FIGS. 5A-5C are photographs depicting immuno-fluorescence staining of iPS cells with markers of pluripotency. J1.2-3 cells were cultured in suspension using medium CM100F for more than 20 passages and were then stained with markers of undifferentiated stem cells. FIG. 5A—TRA-1-81; FIG. 5B—TRA-1-60; FIG. 5C—SSEA4.

Figure 6B:
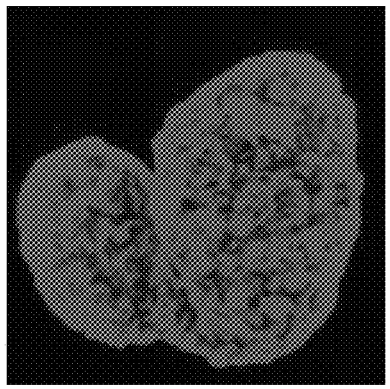
Figure 6D:
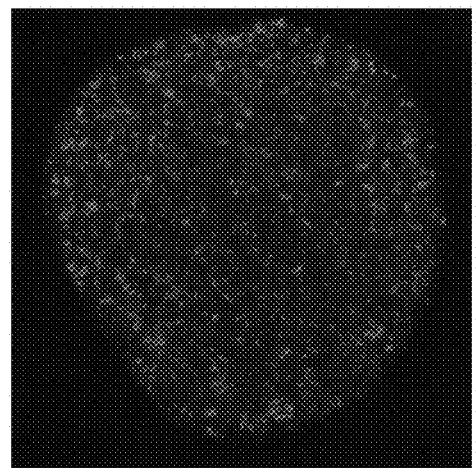
Figure 6A:
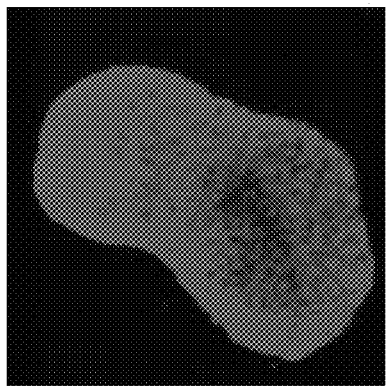
Figure 6C:
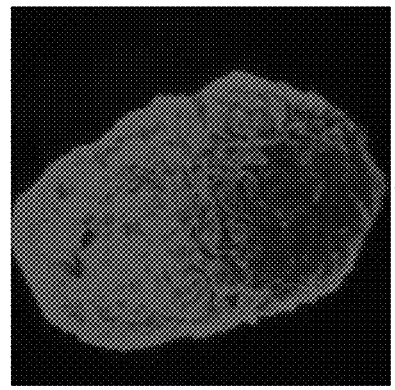

FIGS. 6A-6D are photographs depicting immunostaining of iPS cells with markers of pluripotency. J1.2-3 cells were cultured in suspension using the CM100F medium for at least 30 passages and then were transferred into spinner flasks and were cultured for additional 30 days, following which the cells were stained with markers of undifferentiated stem cells. FIG. 6A—Oct4; FIG. 6B—TRA-1-81; FIG. 6C—TRA-1-60; and FIG. 6D—SSEA4.

DESCRIPTION OF SPECIFIC EMBODIMENTS OF THE INVENTION

The present invention, in some embodiments thereof, relates to novel culture media, cell cultures comprising same and methods utilizing same for maintaining pluripotent stem cells in a proliferative, pluripotent and undifferentiated state and, more particularly, but not exclusively, to methods of expanding hESCs and induced pluripotent stem (iPS) cells in suspension cultures or two-dimensional culture systems while maintaining the cells in a proliferative, pluripotent and undifferentiated state.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have designed following laborious experimentations defined culture media, which are serum-free and xeno-free (e.g., devoid of animal contaminants) and which can maintain pluripotent stem cells such as human iPS and ESCs in an undifferentiated state in the absence of feeder cell support while preserving their pluripotent potential to differentiae into all three embryonic germ layers.

Thus, as shown in the Examples section which follows, hESCs and iPS cells were cultured in an undifferentiated state on two-dimensional culture systems which are either feeder-layer free (e.g., on a synthetic matrix; Example 1) or xeno-free feeder layer-based (e.g., foreskin fibroblasts; FIGS. 1A-C and 2A-C, Example 2) in the presence of serum-free, xeno-free and defined culture media (e.g., mHA40/4. HA75, HA76, HA77, HA78 or HA74). While in culture, the pluripotent stem cells exhibit undifferentiated morphology, as well as morphological and molecular characteristics typical to iPS or hESCs such as normal karyotype, expression of markers of pluripotency (e.g., Oct4, SSEA4, TRA-1-81, TRA-1-60), and ability to differentiate into all three embryonic germ layers both in vitro (by formation of embryoid bodies after at least 28 passages) and in vivo (by formation of teratomas after at least 31 passages).

As used herein the phrase "pluripotent stem cells" refers to cells which are capable of differentiating into cells of all three embryonic germ layers (i.e., endoderm, ectoderm and mesoderm). According to some embodiments of the invention, the phrase "pluripotent stem cells" encompasses embryonic stem cells (ESCs) and induced pluripotent stem cells (iPS cells).

The phrase "embryonic stem cells" may comprise cells which are obtained from the embryonic tissue formed after gestation (e.g., blastocyst) before implantation (i.e., a pre-implantation blastocyst), extended blastocyst cells (EBCs) which are obtained from a post-implantation/pre-gastrulation stage blastocyst (see WO2006/040763] and embryonic germ (EG) cells which are obtained from the genital tissue of a fetus any time during gestation, preferably before 10 weeks of gestation.

According to some embodiments of the invention, the pluripotent stem cells of the invention are embryonic stem cells, such as from a human or primate (e.g., monkey) origin.

The embryonic stem cells of the invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843, 780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

It will be appreciated that commercially available stem cells can also be used with this aspect of the present invention. Human ES cells can be purchased from the NIH human embryonic stem cells registry (www[[.]]dotescr[[.]]dotnih[[.]]dotgov). Non-limiting examples of commercially available embryonic stem cell lines are BG01, BG02, BG03, BG04, CY12, CY30, CY92, CY10, TE03, TE04 and TE06.

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis. MO, USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

Embryonic germ (EG) cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090, 622.

The phrase "induced pluripotent stem (iPS) cell" (or embryonic-like stem cell) as used herein refers to a proliferative and pluripotent stem cell which is obtained by de-differentiation of a somatic cell (e.g., an adult somatic cell).

According to some embodiments of the invention, the iPS cell is characterized by a proliferative capacity which is similar to that of ESCs and thus can be maintained and expanded in culture for an almost unlimited time.

IPS cells can be endowed with pluripotency by genetic manipulation which re-program the cell to acquire embryonic stem cells characteristics. For example, the iPS cells of the invention can be generated from somatic cells by induction of expression of Oct-4, Sox2, Kfl4 and c-Myc in a somatic cell essentially as described in Takahashi and Yamanaka, 2006, Takahashi et al, 2007, Meissner et al, 2007, and Okita et al, 2007). Additionally or alternatively, the iPS cells of the invention can be generated from somatic cells by induction of expression of Oct4, Sox2, Nanog and Lin28 essentially as described in Yu et al, 2007, and Nakagawa et al, 2008. It should be noted that the genetic manipulation (re-programming) of the somatic cells can be performed using any known method such as using plasmids or viral vectors, or by derivation without any integration to the genome [Yu J. et al., Science. 2009, 324: 797-801].

The iPS cells of the invention can be obtained by inducing de-differentiation of embryonic fibroblasts [Takahashi and Yamanaka, 2006; Meissner et al, 2007], fibroblasts formed from hESCs [Park et al, 2008], Fetal fibroblasts [Yu et al, 2007; Park et al, 2008], foreskin fibroblast [Yu et al, 2007; Park et al, 2008], adult dermal and skin tissues [Hanna et al, 2007; Lowry et al, 2008], b-lymphocytes [Hanna et al 2007] and adult liver and stomach cells [Aoi et al, 2008].

IPS cell lines are also available via cell banks such as the WiCell bank. Non-limiting examples of commercially available iPS cell lines include the iPS foreskin clone 1 [WiCell Catalogue No. iPS(foreskin)-1-DL-1], the iPSIMR90 clone 1 [WiCell Catalogue No. iPS(IMR90)-1-DL-1], and the iPSIMR90 clone 4 [WiCell Catalogue No. iPS(IMR90)-4-DL-1].

According to some embodiments of the invention, the induced pluripotent stem cells are human induced pluripotent stem cells.

As used herein the phrase "culture medium" refers to a liquid substance used to support the growth of pluripotent stem cells and maintain them in an undifferentiated state. The culture medium used by the invention according to some embodiments can be a water-based medium which includes a combination of substances such as salts, nutrients, minerals, vitamins, amino acids, nucleic acids, proteins such as cytokines, growth factors and hormones, all of which are needed for cell proliferation and are capable of maintaining the pluripotent stem cells in an undifferentiated state. For example, a culture medium according to an aspect of some embodiments of the invention can be a synthetic tissue culture medium such as the Ko-DMEM (Gibco-Invitrogen Corporation products, Grand Island, NY, USA), DMEM/F12 (Biological Industries, Biet HaEmek, Israel), Mab ADCB medium (HyClone, Utah, USA) supplemented with the necessary additives as is further described hereinunder.

The phrase "feeder cell support" as used herein refers to the ability of a feeder cell (e.g., fibroblasts) to maintain pluripotent stem cells in a proliferative and undifferentiated state when the pluripotent stem cells are co-cultured on the feeder cells or when the pluripotent stem cells are cultured on a matrix (e.g., an extracellular matrix, a synthetic matrix) in the presence of a conditioned medium generated by the feeder cells. The support of the feeder cells depends on the structure of the feeder cells while in culture (e.g., the three dimensional matrix formed by culturing the feeder cells in a tissue culture plate), function of the feeder cells (e.g., the secretion of growth factors, nutrients and hormones by the feeder cells, the growth rate of the feeder cells, the expansion ability of the feeder cells before senescence) and/or the attachment of the pluripotent stem cells to the feeder cell layer(s).

The phrase "absence of feeder cell support" as used herein refers to a culture medium and/or a cell culture being devoid of feeder cells and/or a conditioned medium generated thereby.

As used herein the phrase "serum-free" refers to being devoid of a human or an animal serum.

It should be noted that the function of serum in culturing protocols is to provide the cultured cells with an environment similar to that present in vivo (i.e., within the organism from which the cells are derived, e.g., a blastocyst of an embryo). However, the use of serum, which is derived from either an animal source (e.g., bovine serum) or a human source (human serum), is limited by the significant variations in serum components between the donor individuals (from which the serum is obtained) and the risk of having xeno contaminants (in case of an animal serum is used).

According to some embodiments of the invention, the serum-free culture medium does not comprise serum or portions thereof.

According to some embodiments of the invention, the serum-free culture medium of the invention is devoid of serum albumin (e.g., albumin which is purified from human serum or animal serum).

According to some embodiments of the invention the culture medium comprises serum replacement.

As used herein the phrase "serum replacement" refers to a defined formulation, which substitutes the function of serum by providing pluripotent stem cells with components needed for growth and viability.

Various serum replacement formulations are known in the art and are commercially available.

For example, GIBCO™ KNOCKOUT™ Serum Replacement (Gibco-Invitrogen Corporation, Grand Island, NY USA, Catalogue No. 10828028) is a defined serum-free formulation optimized to grow and maintain undifferentiated ES cells in culture. It should be noted that the formulation of GIBCO™ Knockout™ Serum Replacement includes Albumax (Bovine serum albumin enriched with lipids) which is from an animal source (International Patent Publication No. WO 98/30679 to Price, P. J. et al). However, a recent publication by Crook et al., 2007 (Crook J M., et al., 2007, Cell Stem Cell, 1: 490-494) describes six clinical-grade hESC lines generated using FDA-approved clinical grade foreskin fibroblasts in cGMP-manufactured KNOCK-OUT™ Serum Replacement (Invitrogen Corporation, USA, Catalogue No. 04-0095).

According to some embodiments of the invention, the concentration of GIBCO™ Knockout KNOCKOUT™ Serum Replacement in the culture medium is in the range of from about 1% [volume/volume (v/v)] to about 50% (v/v), e.g., from about 5% (v/v) to about 40% (v/v), e.g., from about 5% (v/v) to about 30% (v/v), e.g., from about 10% (v/v) to about 30% (v/v), e.g., from about 10% (v/v) to about 25% (v/v), e.g., from about 10% (v/v) to about 20% (v/v), e.g., about 10% (v/v), e.g., about 15% (v/v), e.g., about 20% (v/v), e.g., about 30% (v/v).

Another commercially available serum replacement is the B27 supplement without vitamin A which is available from Gibco-Invitrogen, Corporation, Grand Island, NY USA, Catalogue No. 12587-010. The B27 supplement is a serum-free formulation which includes d-biotin, fatty acid free fraction V bovine serum albumin (BSA), catalase, L-carnitine HCl, corticosterone, ethanolamine HCl, D-galactose (Anhyd.), glutathione (reduced), recombinant human insulin, linoleic acid, linolenic acid, progesterone, putrescine-2-HCl, sodium selenite, superoxide dismutase, T-3/albumin complex, DL alpha-tocopherol and DL alpha tocopherol acetate. However, the use of B27 supplement is limited since it includes albumin from an animal source.

According to some embodiments of the invention, the serum replacement is xeno-free.

The term "xeno" is a prefix based on the Greek word "Xenos", i.e., a stranger. As used herein the phrase "xeno-free" refers to being devoid of any components which are derived from a xenos (i.e., not the same, a foreigner) species. Such components can be contaminants such as pathogens associated with (e.g., infecting) the xeno species, cellular components of the xeno species or a-cellular components (e.g., fluid) of the xeno species.

For example, a xeno-free serum replacement can include a combination of insulin, transferrin and selenium. Additionally or alternatively, a xeno-free serum replacement can include human or recombinantly produced albumin, transferrin and insulin.

Non-limiting examples of commercially available xeno-free serum replacement compositions include the premix of ITS (Insulin, Transferrin and Selenium) available from Invitrogen corporation (ITS, Invitrogen, Catalogue No. 5150-056); Serum replacement 3 (Sigma, Catalogue No. S2640) which includes human serum albumin, human transferring and human recombinant insulin and does not contain growth factors, steroid hormones, glucocorticoids, cell adhesion factors, detectable Ig and mitogens.

According to some embodiments of the invention, the xeno-free serum replacement formulations ITS (Invitrogen corporation) and SR3 (Sigma) are diluted in a 1 to 100 ratio in order to reach a ×1 working concentration.

According to some embodiments of the invention the culture medium is capable of maintaining pluripotent stem cell in a proliferative, pluripotent and undifferentiated state for at least about 5 passages, at least about 10 passages, at least about 15 passages, at least about 20 passages, at least about 22 passages, at least about 25 passages, at least about 30 passages, at least about 35 passages, at least about 40 passages, at least about 45 passages, at least about 50 passages and more.

According to some embodiments of the invention the culture medium is capable of expanding the pluripotent stem cells in an undifferentiated state.

As used herein the term "expanding" refers to increasing the number of pluripotent stem cells over the culturing period (by at least about 5%, 10%, 15%, 20%, 30%, 50%, 100%, 200%, 500%, 1000%, and more). It will be appreciated that the number of pluripotent stem cells which can be obtained from a single pluripotent stem cell depends on the proliferation capacity of the pluripotent stem cell. The proliferation capacity of a pluripotent stem cell can be calculated by the doubling time of the cell (i.e., the time needed for a cell to undergo a mitotic division in the culture) and the period the pluripotent stem cell culture can be maintained in the undifferentiated state (which is equivalent to the number of passages multiplied by the days between each passage).

For example, as described in Example 1 of the Examples section which follows, the hESCs or human iPS cells could be maintained in the proliferative, pluripotent and undifferentiated state in the presence of the mHA40/4, HA75, HA76, HA78 and HA74/1 culture media for at least 22 passages when cultured on a feeder-free matrix. Given that each passage occurs every 4-7 days, the hESCs or human iPS cells were maintained for 110 days (i.e., 2640 hours). Given that the hESCs or human iPS doubling time was 36 hours, a single hESC or human iPS cell cultured under these conditions could be expanded to give rise to $2^{73}$ (i.e., $9.4 \times 10^{21}$) hESCs or human iPS cells.

According to some embodiments of the invention, the culture medium of some embodiments of the invention is capable of supporting expansion of a single pluripotent stem cell (e.g., hESC or human iPS cell) or a population of pluripotent stem cells by at least 23 (i.e., $8 \times 10^6$) within about one month, e.g., at least $2^{24}$ (i.e., $16.7 \times 10^6$) within about one month.

According to some embodiments of the invention the serum-free and xeno-free culture medium comprises basic fibroblast growth factor (bFGF), transforming growth factor beta-3 (TGFβ$_3$) and ascorbic acid, wherein a concentration of the ascorbic acid in the culture medium is at least 50 μg/ml and wherein the culture medium is capable of maintaining pluripotent stem cells in an undifferentiated state in the absence of feeder cell support.

Ascorbic acid (also known as vitamin C) is a sugar acid ($C_6H_8O_6$; molecular weight 176.12 grams/mole) with antioxidant properties. The ascorbic acid used by the culture medium of some embodiments of the invention can be a natural ascorbic acid, a synthetic ascorbic acid, an ascorbic acid salt (e.g., sodium ascorbate, calcium ascorbate, potassium ascorbate), an ester form of ascorbic acid (e.g., ascorbyl palmitate, ascorbyl stearate), a functional derivative thereof (a molecule derived from ascorbic acid which exhibits the same activity/function when used in the culture medium of the invention), or an analogue thereof (e.g., a functional equivalent of ascorbic acid which exhibits an activity analogous to that observed for ascorbic acid when used in the culture medium of the invention). Non-limiting examples of ascorbic acid formulations which can be used in the culture medium of some embodiments of the invention include L-ascorbic acid and ascorbic acid 3-phosphate.

Ascorbic acid can be obtained from various manufacturers such as Sigma, St Louis, MO, USA (e.g., Catalogue numbers: A2218, A5960, A7506, A0278, A4403, A4544, A2174, A2343, 95209, 33034, 05878, 95210, 95212, 47863, 01-6730, 01-6739, 255564, A92902, W210901).

As mentioned, the concentration of ascorbic acid in the culture medium is at least about 50 μg/ml. According to some embodiments of the invention, the ascorbic acid can be used in a range of concentrations such as from about 50 μg/ml to about 50 mg/ml, e.g., from about 50 μg/ml to about 5 mg/ml, e.g., from about 50 μg/ml to about 1 mg/ml, e.g., from about 100 μg/ml to about 800 μg/ml, e.g., from about 200 μg/ml to about 800 μg/ml, e.g., from about 300 μg/ml to about 700 μg/ml, e.g., from about 400 μg/ml to about 600 μg/ml, e.g., from about 450 μg/ml to about 550 μg/ml.

According to some embodiments of the invention the concentration of ascorbic acid in the culture medium is at least about 75 μg/ml, e.g., at least about 100 μg/ml, e.g., at least about 150 μg/ml, e.g., at least about 200 μg/ml, e.g., at least about 250 μg/ml, e.g., at least about 300 μg/ml, e.g., at least about 350 μg/ml, e.g., at least about 400 μg/ml, e.g., at least about 450 μg/ml, e.g., about 500 μg/ml.

As is shown in Example 1 of the Examples section which follows, the present inventors have used various culture media which include ascorbic acid at a concentration of at least 50 μg/ml (e.g., the mHA40/4, HA75, HA76, HA77, HA78 and HA74/1 culture media) to successfully culture hESCs and iPS cells and maintain them in a proliferative, pluripotent and undifferentiated state for at least 15 passages in the absence of feeder cell support.

Basic fibroblast growth factor (also known as bFGF, FGF2 or FGF-β) is a member of the fibroblast growth factor family. The bFGF used in the culture medium of some embodiments of the invention can be a purified, a synthetic or a recominantly expressed bFGF protein [(e.g., human bFGF polypeptide GenBank Accession No. NP_001997.5 (SEQ ID NO:31); human bFGF polynucleotide GenBank Accession No. NM_002006.4 (SEQ ID NO:32). It should be noted that for the preparation of a xeno-free culture medium the bFGF is preferably purified from a human source or is recombinantly expressed as is further described hereinbelow. bFGF can be obtained from various commercial sources such as Cell Sciences®, Canton, MA, USA (e.g., Catalogue number CRF001A and CRF001B), Invitrogen Corporation products, Grand Island NY, USA (e.g., Catalogue numbers: PHG0261, PHG0263, PHG0266 and PHG0264), ProSpec-Tany TechnoGene Ltd. Rehovot, Israel (e.g., Catalogue number: CYT-218), and Sigma, St Louis, MO, USA (e.g., catalogue number: F0291).

According to some embodiments the concentration of bFGF in culture medium is in the range from about 1 ng/ml to about 10 μg/ml, e.g., from about 2 ng/ml to about 1 μg/ml, e.g., from about 1 ng/ml to about 500 ng/ml, e.g., from about 2 ng/ml to about 500 ng/ml, e.g., from about 5 ng/ml to about 250 ng/ml, e.g., from about 5 ng/ml to about 200 ng/ml, e.g., from about 5 ng/ml to about 150 ng/ml, e.g., about 10 ng/ml, e.g., about 20 ng/ml, e.g., about 30 ng/ml, e.g., about 40 ng/ml, e.g., about 50 ng/ml, e.g., about 60 ng/ml, e.g., about 70 ng/ml, e.g., about 80 ng/ml, e.g., about 90 ng/ml, e.g., about 100 ng/ml, e.g., about 110 ng/ml, e.g., about 120 ng/ml, e.g., about 130 ng/ml, e.g., about 140 ng/ml, e.g., about 150 ng/ml.

According to some embodiments of the invention the concentration of bFGF in the culture medium is at least about 1 ng/ml, at least about 2 ng/ml, at least about 3 ng, at least about 4 ng/ml, at least about 5 ng/ml, at least about 6 ng/ml, at least about 7 ng, at least about 8 ng/ml, at least about 9 ng/ml, at least about 10 ng/ml, at least about 15 ng/ml, at least about 20 ng/ml, at least about 25 ng/ml, at least about 30 ng/ml, at least about 35 ng/ml, at least about 40 ng/ml, at least about 45 ng/ml, at least about 50 ng/ml, at least about 55 ng/ml, at least about 60 ng/ml, at least about 70 ng/ml, at least about 80 ng/ml, at least about 90 ng/ml, at least about 95 ng/ml, e.g., about 100 ng/ml.

As is shown in Example 1 of the Examples section which follows, the present inventors have used various culture media which include bFGF in the range of 5-200 ng/ml (e.g., the mHA40/4, HA75 and HA78 culture media, which include 10 ng/ml bFGF; the HA76 and HA77 culture media which include 100 ng/ml bFGF; and the HA74/1 culture medium which includes 50 ng/ml bFGF) to successfully culture hESCs and iPS cells and maintain them in a proliferative, pluripotent and undifferentiated state for at least 15 passages in the absence of feeder cell support.

Transforming growth factor beta-3 (TGFβ$_3$) is involved in the control of proliferation, differentiation, and other functions in many cell types, acts in inducing transformation and as a negative autocrine growth factor. TGFβ3 can be obtained from various commercial sources such as R&D Systems Minneapolis MN, USA.

According to some embodiments of the invention, the concentration of TGFβ$_3$ in the culture medium is in the range of about 0.05 ng/ml to about 1 μg/ml, e.g., from 0.1 ng/ml to about 1 μg/ml, e.g., from about of about 0.5 ng/ml to about 100 ng/ml.

According to some embodiments of the invention, the concentration of TGFβ$_3$ in the culture medium is at least about 0.5 ng/ml, e.g., at least about 0.6 ng/ml, e.g., at least about 0.8 ng/ml, e.g., at least about 0.9 ng/ml, e.g., at least about 1 ng/ml, e.g., at least about 1.2 ng/ml, e.g., at least about 1.4 ng/ml, e.g., at least about 1.6 ng/ml, e.g., at least about 1.8 ng/ml, e.g., about 2 ng/ml.

As is shown in Example 1 of the Examples section which follows, the present inventors have used various culture media which include TGFβ$_3$ at a concentration of about 2 ng/ml (e.g., the mHA40/4, HA75, HA76, HA78 and HA74/1 culture media) to successfully culture hESCs and iPS cells and maintain them in a proliferative, pluripotent and undifferentiated state for at least 22 passages in the absence of feeder cell support.

According to some embodiments of the invention, the culture medium comprises bFGF at a concentration range of about 0.1 ng/ml to about 500 ng/ml, TGFβ3 at a concentration range of about 0.1 ng/ml to about 20 ng/ml, and ascorbic acid at a concentration range of about 50 μg/ml to about 5000 μg/ml.

According to some embodiments of the invention, the culture medium of some embodiments of the invention comprises bFGF at a concentration range of about 5 ng/ml to about 150 ng/ml, TGFβ3 at a concentration range of about 0.5 ng/ml to about 5 ng/ml, and ascorbic acid at a concentration range of about 400 μg/ml to about 600 μg/ml.

According to some embodiments of the invention, the culture medium further comprises a lipid mixture.

As used herein the phrase "lipid mixture" refers to a defined (e.g., chemically defined) lipid composition needed for culturing the pluripotent stem cells. It should be noted that the lipid mixture is usually added to a culture medium which is devoid of serum or serum replacement and thus substitutes the lipids which are usually added to formulations of serum or serum replacement.

A non-limiting example of a commercially available lipid mixture, which can be used in the culture medium of some embodiments of the invention, include the Chemically Define Lipid Concentrate available from Invitrogen (Catalogue No. 11905-031).

According to some embodiments of the invention, the concentration of the lipid mixture in the culture medium is from about 0.5% [volume/volume (v/v)] to about 3% v/v, e.g., from about 0.5% v/v to about 2% v/v, e.g., from about 0.5% v/v to about 1% v/v, e.g., about 1% v/v.

According to some embodiments of the invention, the culture medium of some embodiments of the invention comprises bFGF at a concentration range of about 0.1 ng/ml to about 500 ng/ml, TGFβ$_3$ at a concentration range of about 0.1 ng/ml to about 20 ng/ml, ascorbic acid at a concentration range of about 50 μg/ml to about 5000 μg/ml, xeno-free serum replacement and a lipid mixture.

Non-limiting examples of xeno-free and serum-free culture media which comprise TGFβ$_3$, bFGF and ascorbic acid at a concentration of at least 50 μg/ml and which can be used to maintain pluripotent stem cells in a proliferative and undifferentiated states include the HA75 and HA78 culture media.

According to some embodiments of the invention, the culture medium further comprises sodium bicarbonate. Sodium bicarbonate can be obtained from Biological Industries, Beit HaEmek, Israel.

According to some embodiments of the invention, the concentration of sodium bicarbonate in the culture medium is from about 5% to about 10%, e.g., from about 6% to about 9%, e.g., from about 7% to about 8%, e.g., about 7.5%.

The present inventors uncovered that pluripotent stem cells can be maintained in a proliferative, pluripotent and undifferentiated state for at least 15 passages when cultured in a serum-free and xeno-free culture medium which comprises bFGF and ascorbic acid but does not comprise a TGFβ isoform.

As used herein the phrase "TGFβ isoform" refers to any isoform of the transforming growth factor beta (β) including TGFβ$_1$ (e.g., Homo sapiens TGFβ$_1$, GenBank Accession No. NP_000651), TGFβ$_2$ (e.g., Homo sapiens TGFβ$_2$, GenBank Accession No. NP_003229) and TGFβ3 (e.g., Homo sapiens TGFβ$_3$, GenBank Accession No. NP_003230) which functions through the same receptor signaling system in the control of proliferation, differentiation, and other functions in many cell types. TGFβ acts in inducing transformation and also acts as a negative autocrine growth factor.

According to some embodiments of the invention, the culture medium comprises no more than 1 ng/ml of the TGFβ isoform, e.g., no more than 0.5 ng/ml, e.g., no more than 0.1 ng/ml, e.g., no more than 0.05 ng/ml, e.g., no more than 0.01 ng/ml of the TGFβ isoform.

According to some embodiments of the invention, the culture medium is completely devoid of a TGFβ isoform (i.e., TGFβ isoform-free).

According to some embodiments of the invention the culture medium comprises ascorbic acid at a concentration range of about 400-600 μg/ml and basic fibroblast growth factor (bFGF) at a concentration range of about 50-200 ng/ml.

According to some embodiments of the invention the culture medium the culture medium which comprises ascorbic acid at a concentration range of about 400-600 μg/ml and basic fibroblast growth factor (bFGF) at a concentration range of about 50-200 ng/ml is capable of maintaining pluripotent stem cells in an undifferentiated state in the absence of feeder cell support.

According to some embodiments of the invention, the concentration of ascorbic acid in the culture medium is between about 410 μg/ml to about 590 μg/ml, between about 420 μg/ml to about 580 μg/ml, between about 450 μg/ml to about 550 μg/ml, between about 460 μg/ml to about 540 μg/ml, between about 470 μg/ml to about 530 μg/ml, between about 490 μg/ml to about 520 μg/ml, e.g., between about 490 μg/ml to about 510 μg/ml, e.g., about 500 μg/ml.

According to some embodiments of the invention, the concentration of bFGF in the culture medium is between about 50 ng/ml to about 200 ng/ml, between about 60 ng/ml to about 190 ng/ml, between about 70 ng/ml to about 180 ng/ml, between about 80 ng/ml to about 170 ng/ml, between about 90 ng/ml to about 160 ng/ml, between about 90 ng/ml to about 150 ng/ml, between about 90 ng/ml to about 130 ng/ml, between about 90 ng/ml to about 120 ng/ml, e.g., about 100 ng/ml.

According to some embodiments of the invention, the concentration of bFGF in the culture medium is about 50, about 55, about 60, about 65, about 70, about 80, about 85, about 90, about 95, about 100, about 105, about 110, about 115, about 120, about 125, about 130, about 135, about 140, about 145, about 150, about 160, about 165, about 170, about 175, about 180, about 185, about 190, about 195, about 200 ng/ml.

According some embodiments of the invention the culture medium which comprises ascorbic acid at a concentration range of about 400-600 µg/ml and basic fibroblast growth factor (bFGF) at a concentration range of about 50-200 ng/ml, further comprises xeno-free serum replacement.

According to some embodiments of the invention, the culture medium which comprises ascorbic acid at a concentration range of about 400-600 µg/ml and basic fibroblast growth factor (bFGF) at a concentration range of about 50-200 ng/ml, further comprises a lipid mixture.

According to some embodiments of the invention, the culture medium comprises bFGF at a concentration of about 50-200 ng/ml and ascorbic acid at a concentration of about 400-600 µg/ml is devoid of sodium-bicarbonate.

According to some embodiments of the invention, the culture medium comprises bFGF at a concentration of about 50-200 ng/ml and ascorbic acid at a concentration of about 400-600 µg/ml, xeno-free serum replacement at a concentration of about 1% and lipid mixture at a concentration of about 1%.

A non-limiting example of a xeno-free, serum-free, and TGFβ isoform-free culture medium which comprises ascorbic acid at a concentration range of about 400-600 µg/ml, bFGF at a concentration range of about 50-200 ng/ml, xeno-free serum replacement and a lipid mixture and which is capable of maintaining pluripotent stem cells such as hESCs and human iPS cells in a proliferative and undifferentiated state for at least 21 passages in the absence of feeder cell support is the HA77 culture medium (Example 1 of the Examples section which follows) or a culture medium similar to the HA77 medium but which is devoid of sodium bi-carbonate such as a culture medium which consists of DMEM/F12 (94%) (Biological Industries, Israel, Sigma Israel), L-glutamine 2 mM (Invitrogen corporation, Sigma, Israel), ascorbic acid 500 µg/ml (Sigma, Israel), bFGF—100 ng (Invitrogen corporation), SR3—1% (Sigma, Israel), and defined lipid mixture 1% (Invitrogen corporation, Sigma, Israel). The present inventors have uncovered novel serum-free and highly defined culture media, which can maintain pluripotent stem cells in a proliferative, pluripotent and undifferentiated state in two-dimensional and three-dimensional (i.e., a suspension culture) systems in the absence of feeder cell support.

As used herein the phrase "suspension culture" refers to a culture in which the pluripotent stem cells are suspended in a medium rather than adhering to a surface.

According to some embodiments of the invention the serum-free culture medium which can maintain pluripotent stem cells in a proliferative, pluripotent and undifferentiated state in two-dimensional and three-dimensional culture systems in the absence of feeder cell support comprises basic fibroblast growth factor (bFGF) at a concentration range of about 50-200 ng/ml.

According to some embodiments of the invention the culture medium comprises between about 55-190 ng/ml, e.g., between about 60-190 ng/ml, e.g., between about 70-180 ng/ml, e.g., between about 80-160 ng/ml, e.g., between about 90-150 ng/ml, e.g., between about 90-140 ng/ml, e.g., between about 90-130 ng/ml, e.g., between about 90-120 ng/ml, e.g., between about 90-110 ng/ml, e.g., between about 95-105 ng/ml, e.g., about 100 ng/ml.

According to some embodiments of the invention the culture medium which comprises bFGF between about 50-200 ng/ml further comprises serum replacement.

A non-limiting example of a culture medium which comprises bFGF at a concentration between about 50-200 ng/ml is the YF100 medium which comprises a basic medium (e.g., DMEM/F12, 85%), serum replacement (15%), bFGF (100 ng/ml), L-glutamine (2 mM), β-mercaptoethanol (0.1 mM) and non-essential amino acid stock (1%).

According to some embodiments of the invention the serum-free culture medium which can maintain pluripotent stem cells in a proliferative, pluripotent and undifferentiated state in two-dimensional and three-dimensional culture systems in the absence of feeder cell support consists of a basic medium, ascorbic acid at a concentration range of about 50 µg/ml to about 500 µg/ml, bFGF at a concentration range between about 2 ng/ml to about 20 ng/ml, L-glutamine, and serum replacement.

According to some embodiments of the invention the serum-free culture medium which can maintain pluripotent stem cells in a proliferative, pluripotent and undifferentiated state in two-dimensional and three-dimensional culture systems in the absence of feeder cell support consists of a basic medium, ascorbic acid at a concentration range of about 50 µg/ml to about 500 µg/ml, bFGF at a concentration range between about 2 ng/ml to about 20 ng/ml, L-glutamine, serum replacement and a lipid mixture.

According to some embodiments of the invention the concentration of ascorbic acid is about 50 µg/ml.

According to some embodiments of the invention the concentration of ascorbic acid is about 500 µg/ml.

According to some embodiments of the invention the concentration of bFGF is about 4 ng/ml.

The basic medium can be any known tissue culture medium such as DMEM/F12 (Biological Industries, Israel, or Sigma Israel), Ko-DMEM (Invitrogen). The concentration of the basic medium depends on the concentration of the other medium ingredients such as the serum replacement.

The serum replacement can be any xeno-free serum replacement (devoid of animal contaminants) at a concentration range from 1-20% depending on the serum replacement used. For example, if the SR3 serum replacement is used then it concentration in the medium is about 1%.

According to some embodiments of the invention the concentration of L-glutamine is about 2 mM.

According to some embodiments of the invention the concentration of the lipid mixture (Sigma, Israel; or Invitrogen, Israel) is about 1%.

Non-limiting examples of such a culture medium include the modified HA13(a) medium [DMEM/F12 (95%), L-glutamine 2 mM, ascorbic acid 500 µg/ml, bFGF—4 ng, and SR3—1%]; the modified HA13(b) medium [DMEM/F12 (95%), L-glutamine 2 mM, ascorbic acid 500 µg/ml, bFGF—4 ng, SR3—1% and a lipid mixture (1%)]; the modified HA13(c) medium [DMEM/F12 (95%), L-glutamine 2 mM, ascorbic acid 50 µg/ml, bFGF—4 ng, and SR3—1% ]; and the modified HA13(d) medium [DMEM/F12 (95%), L-glutamine 2 mM, ascorbic acid 50 µg/ml, bFGF—4 ng, SR3—1% and a lipid mixture (1%)]. These culture media were capable of maintaining pluripotent stem cells (e.g., hESCs and hips cells) in a proliferative, pluripotent and undifferentiated state for at least 20 passages when cultured in a two-dimensional (e.g., on a feeder-layer free culture system; data not shown) and for at least 20 passages when cultured on a three-dimensional culture system (e.g., suspension culture without adherence to an external substrate, cell encapsulation or to protein carrier; data not shown).

According to some embodiments of the invention the serum-free culture medium which can maintain pluripotent stem cells in a proliferative, pluripotent and undifferentiated state in two-dimensional and three-dimensional culture systems in the absence of feeder cell support comprises an IL6RIL6 chimera at a concentration range of about 50-200 picogram per milliliter (pg/ml).

As used herein the phrase "IL6RIL6 chimera" refers to a chimeric polypeptide which comprises the soluble portion of interleukin-6 receptor [IL-6-R, e.g., the human IL-6-R as set forth by GenBank Accession No. AAH89410; SEQ ID NO:33; e.g., a portion of the soluble IL6 receptors as set forth by amino acids 112-355 (SEQ ID NO:39) of GenBank Accession No. AAH89410] and the interleukin-6 (IL6; e.g., human IL-6 as set forth by GenBank Accession No. CAG29292; SEQ ID NO:35) or a biologically active fraction thereof (e.g., a receptor binding domain).

It should be noted that when constructing the IL6RIL6 chimera the two functional portions (i.e., the IL6 and its receptor) can be directly fused (e.g., attached or translationally fused, i.e., encoded by a single open reading frame) to each other or conjugated (attached or translationally fused) via a suitable linker (e.g., a polypeptide linker). According to some embodiments of the invention, the IL6RIL6 chimeric polypeptide exhibits a similar amount and pattern of glycosylation as the naturally occurring IL6 and IL6 receptor. For example, a suitable IL6RIL6 chimera is as set forth in SEQ ID NO:36 and in FIG. 11 of WO 99/02552 to Revel M., et al., which is fully incorporated herein by reference.

It will be appreciated that any of the proteinaceous factors used in the culture medium of the present invention (e.g., the IL6RIL6 chimera, bFGF, TGFβ$_3$) can be recombinantly expressed or biochemically synthesized. In addition, naturally occurring proteinaceous factors such as bFGF and TGFβ can be purified from biological samples (e.g., from human serum, cell cultures) using methods well known in the art.

Biochemical synthesis of the proteinaceous factors of the present invention (e.g., the IL6RIL6 chimera) can be performed using standard solid phase techniques. These methods include exclusive solid phase synthesis, partial solid phase synthesis methods, fragment condensation and classical solution synthesis.

Recombinant expression of the proteinaceous factors of the present invention (e.g., the IL6RIL6 chimera) can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680, Brogli et al., (1984) Science 224:838-843, Gurley et al. (1986) Mol. Cell. Biol. 6:559-565 and Weissbach & Weissbach, 1988. Methods for Plant Molecular Biology, Academic Press, NY, Section VIII, pp 421-463. Specifically, the IL6RIL6 chimera can be generated as described in PCT publication WO 99/02552 to Revel M., et al. and Chebath J., et al., 1997, which are fully incorporated herein by reference.

According to some embodiments of the invention, the concentration of the IL6RIL6 chimera in the culture medium is in the range from about 55 pg/ml to about 195 pg/ml, e.g., from about 60 pg/ml to about 190 pg/ml, e.g., from about 65 pg/ml to about 185 pg/ml, e.g., from about 70 pg/ml to about 180 pg/ml, e.g., from about 75 pg/ml to about 175 pg/ml, e.g., from about 80 pg/ml to about 170 pg/ml, e.g., from about 85 pg/ml to about 165 pg/ml, e.g., from about 90 pg/ml to about 150 pg/ml, e.g., from about 90 pg/ml to about 140 pg/ml, e.g., from about 90 pg/ml to about 130 pg/ml, e.g., from about 90 pg/ml to about 120 pg/ml, e.g., from about 90 pg/ml to about 110 pg/ml, e.g., from about 95 pg/ml to about 105 pg/ml, e.g., from about 98 pg/ml to about 102 pg/ml, e.g., about 100 pg/ml.

According to some embodiments of the invention, the IL6RIL6 chimera-containing culture medium further comprises bFGF.

According to some embodiments of the invention, concentration of bFGF in the IL6RIL6 chimera-containing culture medium is in the range of from about 1 ng/ml to about 10 μg/ml, e.g., from about 2 ng/ml to about 1 μg/ml, e.g., from about 2 ng/ml to about 500 ng/ml, e.g., from about 5 ng/ml to about 150 ng/ml, e.g., from about 5 ng/ml to about 100 ng/ml, e.g., from about 5 ng/ml to about 80 ng/ml, e.g., from about 5 ng/ml to about 50 ng/ml, e.g., from about 5 ng/ml to about 30 ng/ml, e.g., about 5 ng/ml, e.g., about 10 ng/ml, e.g., about 15 ng/ml, e.g., about 20 ng/ml.

According to some embodiments of the invention, the IL6RIL6 chimera-containing culture medium further comprises serum replacement.

According to some embodiments of the invention, the concentration of KNOCKOUT™ Serum Replacement in the IL6RIL6 chimera-containing culture medium is in the range from about 1% (v/v) to about 50% (v/v), e.g., from about 5% (v/v) to about 40% (v/v), e.g., from about 5% (v/v) to about 30% (v/v), e.g., from about 10% (v/v) to about 30% (v/v), e.g., from about 10% (v/v) to about 25% (v/v), e.g., from about 10% (v/v) to about 20% (v/v), e.g., about 15% (v/v).

According to some embodiments of the invention, the culture medium comprises IL6RIL6 chimera at a concentration range of about 50-200 pg/ml, bFGF at a concentration range of about 5-50 ng/ml and serum replacement at a concentration of about 5-40%.

For example, as is shown in Example 4 of the Examples section which follows, the CM100Fp culture medium was shown capable of maintaining pluripotent stem cells such as hESCs and human iPS cells in a proliferative, pluripotent and undifferentiated state for at least 50 passages in a suspension culture devoid of substrate adherence.

According to some embodiments of the invention, the serum-free culture medium which can maintain pluripotent stem cells in a proliferative, pluripotent and undifferentiated state in two-dimensional and three-dimensional culture systems in the absence of feeder-cells support comprises LIF at a concentration of at least 2000 units/ml.

Leukemia inhibitory factor (LIF) is a pleiotropic cytokine which is involved in the induction of hematopoietic differentiation, induction of neuronal cell differentiation, regulator of mesenchymal to epithelial conversion during kidney development, and may also have a role in immune tolerance at the maternal-fetal interface. The LIF used in the culture medium of some embodiments of the invention can be a purified, synthetic or recombinantly expressed LIF protein [e.g., human LIF polypeptide GenBank Accession No. NP_002300.1 (SEQ ID NO:37); human LIF polynucleotide GenBank Accession No. NM_002309.3 (SEQ ID NO:38). It should be noted that for the preparation of a xeno-free culture medium LIF is preferably purified from a human source or is recombinantly expressed. Recombinant human LIF can be obtained from various sources such as Chemicon, USA (Catalogue No. LIF10100) and AbD Serotec (MorphoSys US Inc, Raleigh, NC 27604, USA). Murine LIF ESGRO® (LIF) can be obtained from Millipore, USA (Catalogue No. ESG1107).

According to some embodiments of the invention, the concentration of LIF in the culture medium is from about 2000 units/ml to about 10,000 units/ml, e.g., from about 2000 units/ml to about 8,000 units/ml, e.g., from about 2000 units/ml to about 6,000 units/ml, e.g., from about 2000 units/ml to about 5,000 units/ml, e.g., from about 2000 units/ml to about 4,000 units/ml.

According to some embodiments of the invention, the concentration of LIF in the culture medium is at least about 2000 units/ml, e.g., at least about 2100 units/ml, e.g., at least about 2200 units/ml, e.g., at least about 2300 units/ml, e.g., at least about 2400 units/ml, e.g., at least about 2500 units/ml, e.g., at least about 2600 units/ml, e.g., at least about 2700 units/ml, e.g., at least about 2800 units/ml, e.g., at least about 2900 units/ml, e.g., at least about 2950 units/ml, e.g., about 3000 units/ml.

According to some embodiments of the invention, the LIF-containing culture medium further comprises bFGF.

The concentration of bFGF in the LIF-containing medium is in the range of about 0.1 ng/ml to about 10 µg/ml, e.g., from about 2 ng/ml to about 1 µg/ml, e.g., from about 2 ng/ml to about 500 ng/ml, e.g., from about 5 ng/ml to about 150 ng/ml, e.g., from about 5 ng/ml to about 100 ng/ml, e.g., from about 5 ng/ml to about 80 ng/ml, e.g., from about 5 ng/ml to about 50 ng/ml, e.g., from about 5 ng/ml to about 30 ng/ml, e.g., about 5 ng/ml, e.g., about 10 ng/ml, e.g., about 15 ng/ml, e.g., about 20 ng/ml.

According to some embodiments of the invention, the LIF-containing culture medium further comprises serum replacement.

According to some embodiments of the invention, the culture medium comprises LIF at a concentration of about 2000-10,000 units/ml, bFGF at a concentration range from about 0.1 ng/ml to about 10 µg/ml and KNOCKOUT™ Serum Replacement at a concentration range from about 1% (v/v) to about 50% (v/v).

According to some embodiments of the invention, the culture medium comprises LIF at a concentration of about 2000-5,000 units/ml, bFGF at a concentration of about 5-50 ng/ml and serum replacement at a concentration of about 5-30%.

For example, as shown in Example 4 of the Examples section which follows, the yFL3 culture medium was shown capable of maintaining pluripotent stem cells such as human ESCs and human iPS cells in a proliferative, pluripotent and undifferentiated state for at least 10 passages when cultured in a suspension culture.

According to some embodiments of the invention, the ingredients included in the culture medium of some embodiments of the invention are substantially pure, with a tissue culture and/or a clinical grade.

According to an aspect of some embodiments of the invention there is provided a cell culture which comprises the pluripotent stem cell of some embodiments of the invention and the culture medium of some embodiments of the invention.

According to an aspect of some embodiments of the invention cell culture is feeder cells free (e.g., being devoid of feeder cells or feeder cell conditioned medium).

According to some embodiments of the invention the pluripotent stem cells which are included in the cell culture of some embodiments of the invention exhibit a stable karyotype (chromosomal stability) during the culturing period, e.g., for at least 2 passages, e.g., at least 4 passages, e.g., at least 8 passages, e.g., at least 15 passages, e.g., at least 20 passages, e.g., at least 25 passages, e.g., at least 30 passages, e.g., at least 35 passages, e.g., at least 40 passages, e.g., at least 45 passages, e.g., at least 50 passages.

According to some embodiments of the invention, the cell culture of the invention exhibit a doubling time of at least 20 hours, e.g., a doubling time which is between 20 to 40 hours (e.g., about 36 hours), thus representing a non-tumorigenic, genetically stable pluripotent stem cells (e.g., hESCs and iPS cells).

According to some embodiments of the invention, the cell culture of the invention is characterized by at least 40%, at least 50%, at least 60%, e.g., at least 70%, e.g., at least 80%, e.g., at least 85%, e.g., at least 90%, e.g., at least 95% of undifferentiated pluripotent stem cells.

According to an aspect of some embodiments of the invention, there is provided a method of expanding and maintaining pluripotent stem cells in a pluripotent and undifferentiated state.

According to some embodiments of the invention, the method of expanding and maintaining pluripotent stem cells in an undifferentiated state is effected by culturing the pluripotent stem cells in any of the novel culture media of the invention (described herein).

According to some embodiments of the invention, the method of expanding and maintaining pluripotent stem cells in an undifferentiated state is effected by culturing the pluripotent stem cells in a culture medium being serum-free, feeder-free, matrix-free and protein carrier-free and comprising basic fibroblast growth factor (bFGF) at a concentration range of about 50-200 ng/ml.

According to some embodiments of the invention culturing is effected on a two-dimensional culture system such as a matrix or a feeder cell layer.

For example, culturing on a two-dimensional culture system can be performed by plating the pluripotent stem cells onto a matrix or a feeder cell layer in a cell density which promotes cell survival and proliferation but limits differentiation. Typically, a plating density of between about 15,000 cells/cm$^2$ and about 3,000,000 cells/cm$^2$ is used.

It will be appreciated that although single-cell suspensions of pluripotent stem cells are usually seeded, small clusters may also be used. To this end, enzymatic digestion (such as with type IV collagenase) utilized for cluster disruption (see "General Materials and Experimental Methods" in the Examples section which follows) is terminated before stem cells become completely dispersed and the cells are triturated with a pipette such that clumps (i.e., 10-200 cells) are formed. However, measures are taken to avoid large clusters which may cause cell differentiation.

As used herein, the term "matrix" refers to any substance to which the pluripotent stem cells can adhere and which therefore can substitute the cell attachment function of feeder cells. Such a matrix typically contains extracellular components to which the pluripotent stem cells can attach and thus it provides a suitable culture substrate.

According to some embodiments of the invention the matrix comprises an extracellular matrix.

The extracellular matrix can be composed of components derived from basement membrane or extracellular matrix components that form part of adhesion molecule receptor-ligand couplings. MATRIGEL® (Becton Dickinson, USA) is one example of a commercially available matrix which is suitable for use with the present invention. MATRIGEL® is a soluble preparation from Engelbreth-Holm-Swarm tumor cells that gels at room temperature to form a reconstituted basement membrane; MATRIGEL® is also available as a growth factor reduced preparation. Other extracellular matrix components and component mixtures which are suitable for use with the present invention include foreskin matrix, laminin matrix, fibronectin matrix, proteoglycan matrix, entactin matrix, heparan sulfate matrix, collagen matrix and the like, alone or in various combinations thereof.

According to some embodiments of the invention the matrix is xeno-free.

In cases where complete animal-free culturing conditions are desired, the matrix is preferably derived from a human source or synthesized using recombinant techniques such as described hereinabove. Such matrices include, for example, human-derived fibronectin, recombinant fibronectin, human-derived laminin, foreskin fibroblast matrix or a synthetic fibronectin matrix. Human derived fibronectin can be from plasma fibronectin or cellular fibronectin, both of which can be obtained from Sigma, St. Louis, MO, USA. Human derived laminin and foreskin fibroblast matrix can be obtained from Sigma, St. Louis, MO, USA. A synthetic fibronectin matrix can be obtained from Sigma. St. Louis, MO, USA.

According to some embodiments of the invention, culturing is effected on a feeder cell layer.

According to some embodiments of the invention, the method of expanding and maintaining pluripotent stem cells in an undifferentiated state is effected by culturing the pluripotent stem cells on a feeder cell layer in a serum-free and xeno-free culture medium which comprises basic fibroblast growth factor (bFGF), transforming growth factor beta-3 (TGFβ3) and ascorbic acid, wherein a concentration of the ascorbic acid in the culture medium is at least 50 µg/ml.

According to some embodiments of the invention, the method of expanding and maintaining pluripotent stem cells in an undifferentiated state is effected by culturing the pluripotent stem cells on a feeder cell layer in a serum-free and xeno-free culture medium which comprises ascorbic acid at a concentration range of about 400-600 µg/ml, basic fibroblast growth factor (bFGF) at a concentration range of about 50-200 ng/ml, xeno-free serum replacement and a lipid mixture.

According to some embodiments of the invention, the feeder cell layer is xeno-free.

According to some embodiments of the invention, the feeder cell layer is a foreskin fibroblasts feeder cell layer.

According to some embodiments of the invention, culturing according to some embodiments of the invention is effected in a suspension culture.

According to some embodiments of the invention, the suspension culture is devoid of substrate adherence, e.g., without adherence to an external substrate such as components of extracellular matrix, a glass microcarrier or beads.

According to some embodiments of the invention, culturing of the pluripotent stem cells in a suspension culture is effected in a protein carrier-free culture medium.

As used herein the phrase "protein carrier" refers to a protein which acts in the transfer of proteins or nutrients (e.g., minerals such as zinc) to the cells in the culture. Such protein carriers can be, for example, albumin (e.g., bovine serum albumin), Albumax (lipid enriched albumin) or plasmanate (human plasma isolated proteins). Since these carriers are derived from either human or animal sources their use in hESCs of human iPS cell cultures is limited by batch-specific variations and/or exposure to pathogens.

Thus, a culture medium which is devoid of a protein carrier (e.g., albumin) is highly advantageous since it enables a truly defined medium that can be manufacture from recombinant or synthetic materials.

According to some embodiments of the invention, culturing of the pluripotent stem cells in a suspension culture is effected in a serum-free and feeder cell-free culture medium.

It should be noted that some protocols of culturing pluripotent stem cells such as hESCs and iPS cells include microencapsulation of the cells inside a semipermeable hydrogel membrane, which allows the exchange of nutrients, gases, and metabolic products with the bulk medium surrounding the capsule (for details see e.g., U.S. Patent Application No. 20090029462 to Beardsley et al.).

According to some embodiments of the invention, the pluripotent stem cells cultured in the suspension culture are devoid of cell encapsulation.

According to an aspect of some embodiments of the invention, there is provided a method of expanding induced pluripotent stem (iPS) cells and maintaining the iPS cells in an undifferentiated state. The method is effected by culturing the iPS cells in a suspension culture under culturing conditions devoid of substrate adherence and devoid of cell encapsulation and which allow expansion of the iPS cells in the undifferentiated state.

According to some embodiments of the invention, culturing of the pluripotent stem cells in a suspension culture is effected in the presence of the IL6RIL6 chimera-containing culture medium in which the concentration of the IL6RIL6 chimera is in the range of about 50-200 picograms per milliliter (pg/ml).

According to some embodiments of the invention, culturing of the pluripotent stem cells in a suspension culture is effected in the presence of the leukemia inhibitory factor (LIF)-containing culture medium in which the concentration of LIF is at least about 2000 units/ml.

According to some embodiments of the invention, culturing of the pluripotent stem cells in a suspension culture is effected in the presence of a medium which comprises basic fibroblast growth factor (bFGF) at a concentration range of about 50 ng/ml to about 200 ng/ml, e.g., between about 60 ng/ml to about 190 ng/ml, e.g., between about 70 ng/ml to about 180 ng/ml, e.g., between about 80 ng/ml to about 170 ng/ml, e.g., between about 90 ng/ml to about 160 ng/ml, e.g., between about 90 ng/ml to about 150 ng/ml, e.g., between about 90 ng/ml to about 130 ng/ml, e.g., between about 90 ng/ml to about 120 ng/ml, e.g., about 100 ng/ml.

For example, a non-limiting example of a medium which was found suitable for culturing hESCs and human iPS cells in a suspension culture devoid of substrate adherence and cell encapsulation is the yF100 medium which comprises serum replacement and 100 ng/ml bFGF.

According to some embodiments of the invention, culturing of the pluripotent stem cells in a suspension culture is effected in the presence of a medium which comprises the IL6RIL6 chimera at a concentration range of about 50-200 nanogram per milliliter (ng/ml) and bFGF at a concentration in the range of 1-50 ng/ml.

For example, a non-limiting example of a medium which was found suitable for culturing hESCs and human iPS cells in a suspension culture devoid of substrate adherence and cell encapsulation is the CM100F medium which comprises serum replacement, the IL6RIL6 chimera at a concentration of 100 ng/ml and bFGF at a concentration of 10 ng/ml.

For example, using the CM100Fp, CM100F, yF100 or yFL3 culture media the present inventors expanded pluripotent stem cells in a suspension culture in a proliferative, pluripotent and undifferentiated state for at least 50 passages (see e.g., FIGS. 3A-C, 4, 5A-C and 6A-D and is described in Examples 4 and 5 of the Examples section which follows).

Culturing in a suspension culture according to the method of some embodiments of the invention is effected by plating the pluripotent stem cells in a culture vessel at a cell density which promotes cell survival and proliferation but limits differentiation. Typically, a plating density of between about $5 \times 10^4$-$2 \times 10^6$ cells per ml is used. It will be appreciated that although single-cell suspensions of stem cells are usually seeded, small clusters such as 10-200 cells may also be used.

In order to provide the pluripotent stem cells with sufficient and constant supply of nutrients and growth factors while in the suspension culture, the culture medium can be replaced on a daily basis, or, at a pre-determined schedule such as every 2-3 days. For example, replacement of the culture medium can be performed by subjecting the pluripotent stem cells suspension culture to centrifugation for about 3 minutes at 80 g, and resuspension of the formed pluripotent stem cells pellet in a fresh medium. Additionally or alternatively, a culture system in which the culture medium is subject to constant filtration or dialysis so as to provide a constant supply of nutrients or growth factors to the pluripotent stem cells may be employed.

Since large clusters of pluripotent stem cells may cause cell differentiation, measures are taken to avoid large pluripotent stem cells aggregates. According to some embodiments of the invention, the formed pluripotent stem cells clumps are dissociated every 5-7 days and the single cells or small clumps of cells are either split into additional culture vessels (i.e., passaged) or remained in the same culture vessel yet with additional culture medium. For dissociation of large pluripotent stem cells clumps, a pellet of pluripotent stem cells (which may be achieved by centrifugation as described hereinabove) or an isolated pluripotent stem cells clump can be subject to enzymatic digestion and/or mechanical dissociation.

Enzymatic digestion of pluripotent stem cells clump(s) can be performed by subjecting the clump(s) to an enzyme such as type IV Collagenase (Worthington biochemical corporation. Lakewood, NJ, USA) and/or Dispase (Invitrogen Corporation products, Grand Island NY, USA). The time of incubation with the enzyme depends on the size of cell clumps present in the suspension culture. Typically, when pluripotent stem cells cell clumps are dissociated every 5-7 days while in the suspension culture, incubation of 20-60 minutes with 1.5 mg/ml type IV Collagenase results in small cell clumps which can be further cultured in the undifferentiated state. Alternatively, pluripotent stem cells clumps can be subjected to incubation of about 25 minutes with 1.5 mg/ml type IV Collagenase followed by five minutes incubation with 1 mg/ml Dispase. It should be noted that passaging of human ESCs with trypsin may result in chromosomal instability and abnormalities (see for example, Mitalipova M M., et al., Nature Biotechnology, 23: 19-20, 2005 and Cowan C A et al., N. Engl. J. of Med. 350: 1353-1356, 2004). According to some embodiments of the invention, passaging hESC or iPS cell with trypsin should be avoided.

Mechanical dissociation of large pluripotent stem cells clumps can be performed using a device designed to break the clumps to a predetermined size. Such a device can be obtained from CellArtis Goteborg, Sweden. Additionally or alternatively, mechanical dissociation can be manually performed using a needle such as a 27 g needle (BD Microlance, Drogheda, Ireland) while viewing the clumps under an inverted microscope.

According to some embodiments of the invention, following enzymatic or mechanical dissociation of the large cell clumps, the dissociated pluripotent stem cells clumps are further broken to small clumps using 200 µl Gilson pipette tips (e.g., by pipetting up and down the cells).

The culture vessel used for culturing the pluripotent stem cells in suspension according to the method of some embodiments of the invention can be any tissue culture vessel (e.g., with a purity grade suitable for culturing pluripotent stem cells) having an internal surface designed such that pluripotent stem cells cultured therein are unable to adhere or attach to such a surface (e.g., non-tissue culture treated cells, to prevent attachment or adherence to the surface). Preferably, in order to obtain a scalable culture, culturing according to some embodiments of the invention is effected using a controlled culturing system (preferably a computer-controlled culturing system) in which culture parameters such as temperature, agitation, pH, and $pO_2$ is automatically performed using a suitable device. Once the culture parameters are recorded, the system is set for automatic adjustment of culture parameters as needed for pluripotent stem cells expansion.

As described in the Examples section which follows, the pluripotent stem cells were cultured under dynamic conditions (i.e., under conditions in which the pluripotent stem cells are subject to constant movement while in the suspension culture; see e.g., FIGS. 6A-D; Example 5) or under non-dynamic conditions (i.e., a static culture; see e.g., FIGS. 3A-C, 4 and 5A-C; Example 4) while preserving their, proliferative, pluripotent capacity and karyotype stability for at least 30 passages.

For non-dynamic culturing of pluripotent stem cells, the pluripotent stem cells can be cultured in uncoated 58 mm Petri dishes (Greiner, Frickenhausn, Germany).

For dynamic culturing of pluripotent stem cells, the pluripotent stem cells can be cultured in spinner flasks [e.g., of 200 ml to 1000 ml, for example 250 ml which can be obtained from CellSpin of Integra Biosciences, Fernwald, Germany; of 100 ml which can be obtained from Bellco, Vineland, NJ; or in 125 ml Erlenmeyer (Corning Incorporated, Corning NY, USA)] which can be connected to a control unit and thus present a controlled culturing system. The culture vessel (e.g., a spinner flask, an Erlenmeyer) is shaken continuously. According to some embodiments of the invention the culture vessels are shaken at 90 rounds per minute (rpm) using a shaker (S3.02.10L, ELMI ltd, Riga, Latvia). According to some embodiments of the invention the culture medium is changed daily.

According to some embodiments of the invention, when cultured according to the teachings of the present invention, the growth of the pluripotent stem cells is monitored to determine their differentiation state. The differentiation state can be determined using various approaches including, for example, morphological evaluation (e.g., as shown in FIGS. 1A-C, 3A-C) and/or detection of the expression pattern of typical markers of the undifferentiated state using immunological techniques such as flow cytometry for membrane-bound markers, immunohistochemistry or immunofluorescence for extracellular and intracellular markers and enzymatic immunoassay, for secreted molecular markers. For example, immunofluorescence employed on hESCs or human iPS cells cultured according to the method of some embodiments of the invention revealed the expression of Oct4, stage-specific embryonic antigen (SSEA) 4, the tumor-rejecting antigen (TRA)-1-60 and TRA-1-81 (FIGS. 2A-C, 5A-C and 6A-D). Additionally, the level of transcripts of specific undifferentiation markers (e.g., Oct 4, Nanog, Sox2, Rex1, Cx43, FGF4) or differentiation markers (e.g., albumin, glucagons, α-cardiac actin, β-globulin, Flk1, AC133 and neurofilament) can be detected using RNA-based techniques such as RT-PCR analysis and/or cDNA microarray analysis.

Determination of ES cell differentiation can also be effected via measurements of alkaline phosphatase activity. Undifferentiated human ES cells have alkaline phosphatase activity which can be detected by fixing the cells with 4% paraformaldehyde and developing with the Vector Red substrate kit according to manufacturer's instructions (Vector Laboratories, Burlingame, California, USA).

The present inventors have uncovered that the novel xeno-free and serum free culture media of the invention can be used to derive new pluripotent stem cell lines.

Thus, as is further shown in the Examples section which follows, using the HA40/4 medium culture medium the present inventors were capable of deriving a new hESC line referred to as "WC1" from whole blastocysts cultured on human foreskin fibroblasts feeder layer (Example 3 of the Examples section which follows).

The term "deriving" as used herein refers to generating an embryonic stem cell line or an induced pluripotent stem cell line from at least one embryonic stem or induced pluripotent cell.

According to some embodiments of the invention, the pluripotent stem cell line is an embryonic stem cell line, and the method of deriving the embryonic stem cell line is effected by: (a) obtaining an embryonic stem cell from a pre-implantation stage blastocyst, post-implantation stage blastocyst and/or a genital tissue of a fetus; and (b) culturing the embryonic stem cell in the culture medium of some embodiments of the invention, thereby deriving the embryonic stem cell line.

As used herein the phrase "embryonic stem cell line" refers to embryonic stem cells which are derived from a single or a group of embryonic stem cells of a single organism (e.g., a single human blastocyst), and which are characterized by the ability to proliferate in culture while maintaining the undifferentiated state and the pluripotent capacity.

Obtaining an embryonic stem cell from a pre-implantation stage blastocyst, post-implantation stage blastocyst and/or a genital tissue of a fetus can be performed using methods known in the art, as described hereinabove and in Example 3 of the Examples section which follows. Briefly, the zona pellucida is removed from a 5-7 day-old blastocyst using Tyrode's acidic solution (Sigma, St Louis MO, USA), the trophoblast layer is specifically removed either by immunosurgery or mechanically using 27 g needles and the exposed ICM is either directly cultured in a suitable culture system (e.g., feeder layers, feeder-free matrix or a suspension culture) in the presence of any of the culture media described hereinabove for 4-10 days (in case a preimplantation blastocyst is used) or subject to in vitro implantation by culturing the ICM for 6-8 days (to obtain cells of a 13 day-old blastocyst in case a post-implantation/pre-gastrulation blastocyst is used) on feeder layers or a feeder-free culturing system which allow implantation of the blastocyst to the surface, following which the implanted cells are isolated and can be further cultured on feeder layers, feeder-free matrix or a suspension culture in the presence of any of the culture media described hereinabove as described hereinunder. When using the genital tissue of a fetus, the genital ridges are dissociated and cut into small chunks which are thereafter disaggregated into cells by mechanical dissociation. The single cell EG cells are then cultured in any of the culture media described hereinabove for 4-10 days.

According to some embodiments of the invention, the pluripotent stem cell line is an induced pluripotent stem cell (iPS cell) line, and the method of deriving the iPS cell line is effected by: (a) inducing a somatic cell to a pluripotent stem cell; and (b) culturing the pluripotent stem cell in the culture medium of some embodiments of the invention, thereby deriving the induced pluripotent stem cell line.

As used herein the phrase "induced pluripotent stem cell line" refers to pluripotent stem cells derived from a single induced pluripotent stem cell, which are characterized by the ability to proliferate in culture while maintaining the undifferentiated state and the pluripotent capacity.

Methods of inducing pluripotent stem cells are well known in the art and examples are given in Takahashi and Yamanaka, 2006; Takahashi et al, 2007; Meissner et al, 2007; Okita et al, 2007; Yu et al, 2007; Nakagawa et al, 2008, Yu J. et al., Science. 2009, 324: 797-801; Park et al, 2008; Hanna et al, 2007; Lowry et al, 2008; Aoi et al, 2008; all of which are fully incorporated by reference herein.

Once obtained the ESCs of iPS cells are further cultured in any of the culture media described hereinabove which allow expansion of the pluripotent stem cells in the undifferentiated state, essentially as described hereinabove.

It will be appreciated that an established pluripotent stem cell line (e.g., embryonic stem cell line or induced pluripotent stem cell line) can be subject to freeze/thaw cycles without hampering the proliferative capacity of the cells in the undifferentiated state while preserving their pluripotent capacity. For example, as is shown in the Examples section which follows, using 15% serum replacement and 10% DMSO, hESCs or human iPS cells were successfully frozen and thawed.

As described in Examples 1, 2, 4 and 5 of the Examples section which follows, hESCs and human iPS cells which were expanded and maintained in any of the culture media described hereinabove are pluripotent (i.e., capable of differentiating into all cell types of the three embryonic germ layers, the ectoderm, the endoderm and the mesoderm) as evidenced in vitro (by the formation of EBs) and in vivo (by the formation of teratomas) after a prolonged culture period (e.g., of at least 20 or 30 passages) in the two-dimensional (e.g., feeder-free matrices or foreskin feeders) or three-dimensional (e.g., static or dynamic suspension cultures) culture systems. Thus, hESCs or human iPS cells cultured according to the teachings of the present invention can be used as a source for generating differentiated, lineage-specific cells. Such cells can be obtained directly from the ESCs by subjecting the ESCs to various differentiation signals (e.g., cytokines, hormones, growth factors) or indirectly, via the formation of embryoid bodies and the subsequent differentiation of cells of the EBs to lineage-specific cells.

Thus, according to an aspect of the some embodiments of the invention there is provided a method of generating embryoid bodies from pluripotent stem cells. The method is effected by (a) culturing the pluripotent stem cells according to the method of some embodiment of the invention to thereby obtain expanded, undifferentiated pluripotent stem cells; and (b) subjecting the expanded, undifferentiated pluripotent stem cells to culturing conditions suitable for differentiating the stem cells to embryoid bodies, thereby generating the embryoid bodies from the pluripotent stem cells.

As used herein the phrase "embryoid bodies" refers to morphological structures comprised of a population of ESCs, extended blastocyst cells (EBCs), embryonic germ cells (EGCs) and/or induced pluripotent stem cells which have undergone differentiation. EBs formation initiates following the removal of differentiation blocking factors from the pluripotent stem cell cultures. In the first step of EBs formation, the pluripotent stem cells proliferate into small masses of cells which then proceed with differentiation. In the first phase of differentiation, following 1-4 days in culture for either human ESCs or human iPS cells, a layer of endodermal cells is formed on the outer layer of the small mass, resulting in "simple EBs". In the second phase, following 3-20 days post-differentiation, "complex EBs" are formed. Complex EBs are characterized by extensive differentiation of ectodermal and mesodermal cells and derivative tissues.

Thus, the method according to some embodiments of the invention involves the culturing of the pluripotent stem cells in any of the culture media described hereinabove in order to obtain expanded, undifferentiated pluripotent stem cells and then subjecting the expanded, undifferentiated pluripotent stem cells (e.g., ESCs or iPS cells) to culturing conditions suitable for differentiating the pluripotent stem cells to embryoid bodies. Such culturing conditions are substantially devoid of differentiation inhibitory factors which are employed when pluripotent stem cells are to be expanded in an undifferentiated state, such as $TGF\beta_3$, ascorbic acid at a concentration of at least 50 µg/ml, bFGF and/or the IL6RIL6 chimera.

For EBs formation, the pluripotent stem cells (ESCs or iPS cells) are removed from their feeder cell layers, feeder-free-culturing systems or suspension cultures and are transferred to a suspension culture in the presence of a culture medium containing serum or serum replacement and being devoid of differentiation-inhibitory factors (see e.g., Examples 1, 2, 4 and 5 of the Examples section which follows). For example, a culture medium suitable for EBs formation may include a basic culture medium (e.g., Ko-DMEM or DMEM/F12) supplemented with 20% FBSd (HyClone, Utah, USA), 1 mM L-glutamine, 0.1 mM β-mercaptoethanol, and 1% non-essential amino acid stock.

Monitoring the formation of EBs is within the capabilities of those skilled in the art and can be effected by morphological evaluations (e.g., histological staining) and determination of expression of differentiation-specific markers [e.g., using immunological techniques or RNA-based analysis (e.g., RT-PCR, cDNA microarray)].

It will be appreciated that in order to obtain lineage-specific cells from the EBs, cells of the EBs can be further subjected to culturing conditions suitable for lineage-specific cells.

Preferably, the method of this aspect of the present invention further includes step (c) of subjecting cells of the embryoid bodies to culturing conditions suitable for differentiating and/or expanding lineage specific cells; thereby generating the lineage-specific cells from the embryonic stem cells.

As used herein the phrase "culturing conditions suitable for differentiating and/or expanding lineage specific cells" refers to a combination of culture system, e.g., feeder cell layers, feeder-free matrix or a suspension culture and a culture medium which are suitable for the differentiation and/or expansion of specific cell lineages derived from cells of the EBs. Non-limiting examples of such culturing conditions are further described hereinunder.

According to some embodiments of the invention, the method of this aspect of the invention further includes isolating lineage specific cells following step (b).

As used herein, the phrase "isolating lineage specific cells" refers to the enrichment of a mixed population of cells in a culture with cells predominantly displaying at least one characteristic associated with a specific lineage phenotype. It will be appreciated that all cell lineages are derived from the three embryonic germ layers. Thus, for example, hepatocytes and pancreatic cells are derived from the embryonic endoderm, osseous, cartilaginous, elastic, fibrous connective tissues, myocytes, myocardial cells, bone marrow cells, vascular cells (namely endothelial and smooth muscle cells), and hematopoietic cells are differentiated from embryonic mesoderm and neural, retina and epidermal cells are derived from the embryonic ectoderm.

According to some preferred embodiments of the invention, isolating lineage specific cells is effected by sorting of cells of the EBs via fluorescence activated cell sorter (FACS).

Methods of isolating EB-derived-differentiated cells via FACS analysis are known in the art. According to one method, EBs are disaggregated using a solution of Trypsin and EDTA (0.025% and 0.01%, respectively), washed with 5% fetal bovine serum (FBS) in phosphate buffered saline (PBS) and incubated for 30 min on ice with fluorescently-labeled antibodies directed against cell surface antigens characteristics to a specific cell lineage. For example, endothelial cells are isolated by attaching an antibody directed against the platelet endothelial cell adhesion molecule-1 (PECAM1) such as the fluorescently-labeled PECAM1 antibodies (30884X) available from PharMingen (PharMingen, Becton Dickinson Bio Sciences, San Jose, CA, USA) as described in Levenberg, S. et al., (Endothelial cells derived from human embryonic stem cells. Proc. Natl. Acad. Sci. USA. 2002. 99: 4391-4396). Hematopoietic cells are isolated using fluorescently-labeled antibodies such as CD34-FITC, CD45-PE, CD31-PE, CD38-PE, CD90-FITC, CD117-PE, CD15-FITC, class I-FITC, all of which IgG1 are available from PharMingen, CD133/1-PE (IgG1) (available from Miltenyi Biotec, Auburn, CA), and glycophorin A-PE (IgG1), available from Immunotech (Miami, FL). Live cells (i.e., without fixation) are analyzed on a FACScan (Becton Dickinson Bio Sciences) by using propidium iodide to exclude dead cells with either the PC-LYSIS or the CELL-QUEST software. It will be appreciated that isolated cells can be further enriched using magnetically-labeled second antibodies and magnetic separation columns (MACS, Miltenyi) as described by Kaufman, D. S. et al., (Hematopoietic colony-forming cells derived from human embryonic stem cells. Proc. Natl. Acad. Sci. USA. 2001, 98: 10716-10721).

According to some embodiments of the invention, isolating lineage specific cells is effected by a mechanical separation of cells, tissues and/or tissue-like structures contained within the EBs.

For example, beating cardiomyocytes can be isolated from EBs as disclosed in U.S. Pat. Appl. No. 20030022367 to Xu et al. Four-day-old EBs of the present invention are transferred to gelatin-coated plates or chamber slides and are allowed to attach and differentiate. Spontaneously contracting cells, which are observed from day 8 of differentiation, are mechanically separated and collected into a 15-mL tube containing low-calcium medium or PBS. Cells are dissociated using Collagenase B digestion for 60-120 minutes at 37° C., depending on the Collagenase activity. Dissociated cells are then resuspended in a differentiation KB medium (85 mM KCI, 30 mM $K_2HPO_4$, 5 mM $MgSO_4$, 1 mM EGTA, 5 mM creatine, 20 mM glucose, 2 mM Na$_2$ATP, 5 mM pyruvate, and 20 mM taurine, buffered to pH 7.2, Maltsev et al., Circ. Res. 75:233, 1994) and incubated at 37° C. for 15-30 min. Following dissociation cells are seeded into chamber slides and cultured in the differentiation medium to generate single cardiomyocytes capable of beating.

According to some embodiments of the invention, isolating lineage specific cells is effected by subjecting the EBs to differentiation factors to thereby induce differentiation of the EBs into lineage specific differentiated cells.

Following is a non-limiting description of a number of procedures and approaches for inducing differentiation of EBs to lineage specific cells.

To differentiate the EBs of some embodiments of the invention into neural precursors, four-day-old EBs are cultured for 5-12 days in tissue culture dishes including DMEM/F-12 medium with 5 mg/ml insulin, 50 mg/ml transferrin, 30 nM selenium chloride, and 5 mg/ml fibronectin (ITSFn medium, Okabe, S. et al., 1996, Mech. Dev. 59: 89-102). The resultant neural precursors can be further transplanted to generate neural cells in vivo (Brüstle, O. et al., 1997. In vitro-generated neural precursors participate in mammalian brain development. Proc. Natl. Acad. Sci. USA. 94: 14809-14814). It will be appreciated that prior to their transplantation, the neural precursors are trypsinized and triturated to single-cell suspensions in the presence of 0.1% DNase.

EBs of some embodiments of the invention can differentiate to oligodendrocytes and myelinate cells by culturing the cells in modified SATO medium, i.e., DMEM with bovine serum albumin (BSA), pyruvate, progesterone, putrescine, thyroxine, triiodothryonine, insulin, transferrin, sodium selenite, amino acids, neurotrophin 3, ciliary neurotrophic factor and Hepes (Bottenstein, J. E. & Sato, G. H., 1979, Proc. Natl. Acad. Sci. USA 76, 514-517; Raff, M. C., Miller, R. H., & Noble, M., 1983, Nature 303: 390-396]. Briefly, EBs are dissociated using 0.25% Trypsin/EDTA (5 min at 37° C.) and triturated to single cell suspensions. Suspended cells are plated in flasks containing SATO medium supplemented with 5% equine serum and 5% fetal calf serum (FCS). Following 4 days in culture, the flasks are gently shaken to suspend loosely adhering cells (primarily oligodendrocytes), while astrocytes are remained adhering to the flasks and further producing conditioned medium. Primary oligodendrocytes are transferred to new flasks containing SATO medium for additional two days. Following a total of 6 days in culture, oligospheres are either partially dissociated and resuspended in SATO medium for cell transplantation, or completely dissociated and a plated in an oligosphere-conditioned medium which is derived from the previous shaking step [Liu, S. et al., (2000). Embryonic stem cells differentiate into oligodendrocytes and myelinate in culture and after spinal cord transplantation. Proc. Natl. Acad. Sci. USA. 97: 6126-6131].

For mast cell differentiation, two-week-old EBs of some embodiments of the invention are transferred to tissue culture dishes including DMEM medium supplemented with 10% FCS, 2 mM L-glutamine, 100 units/ml penicillin, 100 mg/ml streptomycin, 20% (v/v) WEHI-3 cell-conditioned medium and 50 ng/ml recombinant rat stem cell factor (rrSCF, Tsai, M. et al., 2000. In vivo immunological function of mast cells derived from embryonic stem cells: An approach for the rapid analysis of even embryonic lethal mutations in adult mice in vivo. Proc Natl Acad Sci USA. 97: 9186-9190). Cultures are expanded weekly by transferring the cells to new flasks and replacing half of the culture medium.

To generate hemato-lymphoid cells from the EBs of some embodiments of the invention. 2-3 days-old EBs are transferred to gas-permeable culture dishes in the presence of 7.5% CO$_2$ and 5% O$_2$ using an incubator with adjustable oxygen content. Following 15 days of differentiation, cells are harvested and dissociated by gentle digestion with Collagenase (0.1 unit/mg) and Dispase (0.8 unit/mg), both are available from F. Hoffman-La Roche Ltd, Basel, Switzerland. CD45-positive cells are isolated using anti-CD45 monoclonal antibody (mAb) M1/9.3.4.HL.2 and paramagnetic microbeads (Miltenyi) conjugated to goat anti-rat immunoglobulin as described in Potocnik, A. J. et al., (Immunology Hemato-lymphoid in vivo reconstitution potential of subpopulations derived from in vitro differentiated embryonic stem cells. Proc. Natl. Acad. Sci. USA. 1997, 94: 10295-10300). The isolated CD45-positive cells can be further enriched using a single passage over a MACS column (Miltenyi).

It will be appreciated that the culturing conditions suitable for the differentiation and expansion of the isolated lineage specific cells include various tissue culture media, growth factors, antibiotic, amino acids and the like and it is within the capability of one skilled in the art to determine which conditions should be applied in order to expand and differentiate particular cell types and/or cell lineages.

Additionally or alternatively, lineage specific cells can be obtained by directly inducing the expanded, undifferentiated pluripotent stem cells such as ESCs or iPS cells to culturing conditions suitable for the differentiation of specific cell lineage.

According to an aspect of some embodiments of the invention there is provided a method of generating lineage-specific cells from pluripotent stem cells. The method is effected by (a) culturing the pluripotent stem cells according to the method of some embodiments of the invention, to thereby obtain expanded, undifferentiated stem cells; and (b) subjecting the expanded, undifferentiated stem cells to culturing conditions suitable for differentiating and/or expanding lineage specific cells, thereby generating the lineage-specific cells from the pluripotent stem cells.

Following are non-limiting examples of culturing conditions which are suitable for differentiating and/or expanding lineage specific cells from pluripotent stem cells (e.g., ESCs and iPS cells).

Mesenchymal stromal cells which are CD73-positive and SSEA-4-negative can be generated from hESCs by mechanically increasing the fraction of fibroblast-like differentiated cells formed in cultures of hESCs, essentially as described in Trivedi P and Hematti P. Exp Hematol. 2008, 36(3):350-9. Briefly, to induce differentiation of hESC the intervals between medium changes are increased to 3-5 days, and the cells at the periphery of the ESC colonies become spindle-shaped fibroblast-looking cells. After 9-10 days under these conditions when about 40-50% of the cells in the culture acquire the fibroblast-looking appearance, the undifferentiated portions of ESC colonies are physically removed and the remaining differentiated cells are passaged to new culture plates under the same conditions.

To induce differentiation of hESCs into dopaminergic (DA) neurons, the cells can be co-cultured with the mouse stromal cell lines PA6 or MS5, or can be cultured with a combination of stromal cell-derived factor 1 (SDF-1/CXCL12), pleiotrophin (PTN), insulin-like growth factor 2 (IGF2) and ephrin B1 (EFNB1) essentially as described in Vazin T, et al., PLoS One. 2009 Aug. 12; 4(8):e6606; and in Elkabetz Y., et al., Genes Dev. 2008 Jan. 15; 22: 152-165.

To generate mesencephalic dopamine (mesDA) neurons, hESCs can be genetically modified to express the transcription factor Lmx1a (e.g., using a lentiviral vector with the PGK promoter and Lmx1a) essentially as described in Friling S., et al., Proc Natl Acad Sci USA. 2009, 106: 7613-7618.

To generate lung epithelium (type II pneumocytes) from hESCs, the ESCs can be cultured in the presence of a commercially available cell culture medium (Small Airway Growth Medium; Cambrex, College Park, MD), or alternatively, in the presence of a conditioned medium collected from a pneumocyte cell line (e.g., the A549 human lung adenocarcinoma cell line) as described in Rippon H J., et al., Proc Am Thorac Soc. 2008:5:717-722.

To induce differentiation of hESCs or human iPS cells into neural cells, the pluripotent stem cells can be cultured for about 5 days in the presence of a serum replacement medium supplemented with TGF-b inhibitor (SB431542, Tocris; e.g., 10 nM) and Noggin (R&D; e.g., 500 ng/ml), following which the cells are cultured with increasing amounts (e.g., 25%, 50%, 75%, changed every two days) of N2 medium (Li X J., et al., Nat Biotechnol. 2005, 23:215-21) in the presence of 500 ng/mL Noggin, essentially as described in Chambers S M., et al., Nat Biotechnol. 2009, 27: 275-280.

In addition to the lineage-specific primary cultures, EBs of the invention can be used to generate lineage-specific cell lines which are capable of unlimited expansion in culture.

Cell lines of the present invention can be produced by immortalizing the EB-derived cells by methods known in the art, including, for example, expressing a telomerase gene in the cells (Wei, W. et al., 2003. Mol Cell Biol. 23:2859-2870) or co-culturing the cells with NIH 3T3 hph-HOX11 retroviral producer cells (Hawley, R. G. et al., 1994. Oncogene 9: 1-12).

It will be appreciated that since the lineage-specific cells or cell lines obtained according to the teachings of the invention are developed by differentiation processes similar to those naturally occurring in the human embryo they can be further used for human cell-based therapy and tissue regeneration.

Thus, the invention envisages the use of the expanded and/or differentiated lineage-specific cells or cell lines of some embodiments of the invention for treating a disorder requiring cell replacement therapy.

For example, oligodendrocyte precursors can be used to treat myelin disorders (Repair of myelin disease: Strategies and progress in animal models. Molecular Medicine Today. 1997. pp. 554-561), chondrocytes or mesenchymal cells can be used in treatment of bone and cartilage defects (U.S. Pat. No. 4,642,120) and cells of the epithelial lineage can be used in skin regeneration of a wound or burn (U.S. Pat. No. 5,716,411).

For certain disorders, such as genetic disorders in which a specific gene product is missing [e.g., lack of the CFTR gene-product in cystic fibrosis patients (Davies J C, 2002. New therapeutic approaches for cystic fibrosis lung disease. J. R. Soc. Med. 95 Suppl 41:58-67)], ESC-derived cells or iPS cells-derived cells are preferably manipulated to over-express the mutated gene prior to their administration to the individual. It will be appreciated that for other disorders, the ESC-derived cells or iPS-derived cells should be manipulated to exclude certain genes.

Over-expression or exclusion of genes can be effected using knock-in and/or knock-out constructs [see for example, Fukushige, S. and Ikeda, J. E.: Trapping of mammalian promoters by Cre-lox site-specific recombination. DNA Res 3 (1996) 73-50; Bedell, M. A., Jerkins, N. A. and Copeland, N. G.: Mouse models of human disease. Part I: Techniques and resources for genetic analysis in mice. Genes and Development 11 (1997) 1-11; Bermingham, J. J., Scherer, S. S., O'Connell, S., Arroyo. E., Kalla, K. A., Powell, F. L. and Rosenfeld. M. G.: Tst-1/Oct-6/SCIP regulates a unique step in peripheral myelination and is required for normal respiration. Genes Dev 10 (1996) 1751-62].

In addition to cell replacement therapy, the lineage specific cells of some embodiments of the invention can also be utilized to prepare a cDNA library. mRNA is prepared by standard techniques from the lineage specific cells and is further reverse transcribed to form cDNA. The cDNA preparation can be subtracted with nucleotides from embryonic fibroblasts and other cells of undesired specificity, to produce a subtracted cDNA library by techniques known in the art.

The lineage specific cells of some embodiments of the invention can be used to screen for factors (such as small molecule drugs, peptides, polynucleotides, and the like) or conditions (such as culture conditions or manipulation) that affect the differentiation of lineage precursor to terminally differentiated cells. For example, growth affecting substances, toxins or potential differentiation factors can be tested by their addition to the culture medium.

As used herein the term "about" refers to ±10%.

The terms "comprises", "comprising", "includes", "including". "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

All the information contained therein is incorporated herein by reference.

General Materials and Experimental Methods

Cell Lines iPS cell culture—Induced pluripotent stem (iPS) cell lines J1.2-3 and iF4 [Park et al, 2008] derived from foreskin fibroblast and adult fibroblasts respectively, were cultured with inactivated mouse embryonic fibroblasts (MEF) as was previously described [Park et al, 2008]. The following culture media combinations were tested for their ability to support the growth of iPS cells in attached [two-dimensional (2D)] cultures:

hESC culture—The human ESC lines I4, I3, I6 and H9.2 were used in the study.

Culturing conditions on two-dimensions: hESCs lines or human iPS cell lines were cultured with MEFs or on synthetic matrices in the presence of the tested culture media. Cells were passaged every four to six days using 1 mg/ml type IV collagenase (Gibco Invitrogen Corporation. Grand Island NY, USA) and plated at a density of $1 \times 10^4$-$3 \times 10^5$ cells per $cm^2$.

Media Used for 2D Cultures—

(i) yF10 basic culture medium consisting of 85% DMEM/F12 (Biological Industries, Beit Haemek, Israel), 15% KNOCKOUT™ serum replacement (SR; Invitrogen), 2 mM L-glutamine, 0.1 mM β-mercaptoethanol, 1% non-essential amino acid stock, and 10 ng/ml basic fibroblast growth factor (bFGF), all from Invitrogen Corporation products, Grand Island NY, USA, unless otherwise indicated. This basic culture medium was used as a control and for the routine growth of iPS cells or hESCs with inactivated MEF or foreskin fibroblasts as feeder layers in 2D cultures.

(ii) mHA40/4 DMEM/F12 (94%) (Biological Industries, Israel), ITS 1% [Invitrogen corporation; the ITS premix is a ×100 stock solution consists of 1.25 mg Insulin, 1.25 mg Transferrin and 1.25 mg Selenius acid], 2 ng/ml $TGFβ_3$ (from R&D Systems Minneapolis MN, USA), L-glutamine 2 mM (Invitrogen corporation), ascorbic acid 500 μg/ml (Sigma, Israel), bFGF—10 ng (Invitrogen corporation), Human serum albumin—0.5% (Sigma, Catalogue No. A1653). Na-Bicarbonate (7.5%) (Biological Industries, Israel), defined lipid mixture 1% (Invitrogen corporation).

(iii) HA75 DMEM/F12 (94%) (Biological Industries, Israel), L-glutamine 2 mM (Invitrogen corporation), ascorbic acid 500 μg/ml (Sigma), bFGF—10 ng (Invitrogen Corporation), $TGFβ_3$ 2 ng/ml (R&D Systems Minneapolis MN, USA). SR3 (serum replacement)—1% (Sigma, Israel), defined lipid mixture 1% (Invitrogen corporation).

(iv) HA76 DMEM/F12 (94%) (Biological Industries. Beit HaEmek, Israel). ITS 1% (Invitrogen corporation), L-glutamine 2 mM (Invitrogen corporation), ascorbic acid 500 μg/ml (Sigma, Israel), bFGF—100 ng (Invitrogen corporation), $TGFβ_3$ 2 ng/ml (R&D Systems Minneapolis MN, USA), Human serum albumin serum—1% (Sigma, Catalogue No. A1653). Na-Bicarbonate (7.5%) (Biological Industries, Israel), defined lipid mixture 1% (Invitrogen corporation).

(v) HA77 DMEM/F12 (94%) (Biological Industries. Israel, Sigma Israel), L-glutamine 2 mM (Invitrogen corporation, Sigma, Israel), ascorbic acid 500 µg/ml (Sigma, Israel), bFGF—100 ng (Invitrogen corporation), Na-Bicarbonate (7.5%) (Biological Industries, Israel). SR3—1% (Sigma, Israel), defined lipid mixture 1% (Invitrogen corporation, Sigma, Israel). It should be noted that the HA77 DMEM/F12 (94%) can also be used without Na-Bicarbonate at all and yet support the culture of pluripotent stem cells (e.g., hESCs and iPSCs) in a proliferative, pluripotent and undifferentiated state for at least 10 passages.

(vi) HA78 DMEM/F12 (94%) (Biological Industries, Israel), L-glutamine 2 mM (Invitrogen corporation), ascorbic acid 500 µg/ml (Sigma, Israel), bFGF—10 ng/ml (Invitrogen corporation), TGFβ$_3$ 2 ng/ml (R&D Systems Minneapolis MN, USA), SR3™—1% (Sigma, Israel), Na-Bicarbonate (7.5%) (Biological Industries, Israel), defined lipid mixture 1% (Invitrogen corporation).

(v) HA74/1 DMEM/F12 (94%) (Biological Industries, Israel), ITS 1% (Invitrogen corporation), L-glutamine 2 mM (Invitrogen corporation), ascorbic acid 500 µg/ml (Sigma, Israel), bFGF—50 ng/ml (Invitrogen corporation), TGFβ$_3$ 2 ng/ml (R&D Systems Minneapolis MN, USA), Human serum albumin—0.5% (Sigma, Israel, Catalogue No. A1653), Na-Bicarbonate (7.5%) (Biological Industries, Israel), defined lipid mixture 1% (Invitrogen Corporation).

It should be noted that when recombinant human Albumin (SIGMA, Catalogue No. A7223) was used instead of human serum Albumin (SIGMA, Catalogue No. A1653) in the mHA40/4, HA76, HA74/1 culture media, these culture media were found to support the growth of hESCs and iPS cells in a pluripotent and undifferentiated state for an extended period of culture. Thus, these results demonstrate that recombinant human albumin can be used instead of human serum albumin in the culture media of some embodiments of the invention and thereby provide defined, xeno-free conditions.

Culturing conditions in three-dimension culture systems (suspension culture):

Media used for suspension cultures—

(i) CM100Fp medium consisting of the basic culture medium (yF10 basic culture medium) supplemented with 100 pg/ml IL6RIL6 chimera. The 85-Kda IL6RIL6 was produced and purified as described and was donated by InterPharm, Merck-Serono group (Nes-Ziona, Israel and Geneva, Switzerland).

(ii) CM100F medium consisting of the basic culture medium (yF10 basic culture medium) supplemented with 100 ng/ml IL6RIL6 chimera. The 85-Kda IL6RIL6 was produced and purified as described and was donated by InterPharm, Merck-Serono group (Nes-Ziona, Israel and Geneva, Switzerland).

(iii) yF100 basic medium (yF10 basic culture medium) in which instead of 10 ng/ml bFGF 100 ng/ml bFGF was used. This medium was found to support hESCs suspension culture with the same efficiency as CM100F.

(iv) yFL3 medium consists of the yF10 basic culture medium with 4 ng/ml bFGF instead of 10 ng/ml bFGF, and supplemented with 3000 units/ml leukemia inhibitory factor (LIF). It should be noted that iPS cells were cultured with the yFL3 medium which comprised 4 or 10 ng/ml bFGF with the same efficiency.

(v) modified HA13(a) medium consists of DMEM/F12 (95%), L-glutamine 2 mM, ascorbic acid 500 µg/ml, bFGF—4 ng, and SR3—1% ]. Was found to support hESCs and iPSCs in a 2-dimensional and 3-dimensional culture systems.

(vi) modified HA13(b) medium consists of DMEM/F12 (95%), L-glutamine 2 mM, ascorbic acid 500 µg/ml, bFGF—4 ng, SR3—1% and a lipid mixture (1%)]. Was found to support hESCs and iPSCs in a 2-dimensional and 3-dimensional culture systems.

(vii) modified HA13(c) medium consists of DMEM/F12 (95%), L-glutamine 2 mM, ascorbic acid 50 µg/ml, bFGF—4 ng, and SR3—1%. Was found to support hESCs and iPSCs in a 2-dimensional and 3-dimensional culture systems.

(viii) modified HA13(d) medium consists of DMEM/F12 (95%), L-glutamine 2 mM, ascorbic acid 50 µg/ml, bFGF—4 ng, SR3—1% and a lipid mixture (1%)]. Was found to support hESCs and iPSCs in a 2-dimensional and 3-dimensional culture systems.

Culture in static suspension (3-dimensional) cultures—To initiate suspension cultures, the iPS cells or the hESCs were removed from their culture dish using 1.5 mg/ml type IV collagenase (Worthington biochemical corporation, Lakewood, NJ, USA), further broken into small clumps using 200 µl Gilson pipette tips, and cultured in suspension in 58 mm Petri dishes (Greiner, Frickenhausen, Germany) at a cell density of $1\times10^6$-$5\times10^6$ cells/dish (5-8 ml of medium in 58-mm dishes). The Petri dishes were kept static in an incubator at 37° C. in 5% CO$_2$. When required, differentiating clumps were removed from the culture during the first three passages while the cells adapted to the new culture conditions. The medium in the suspension culture was changed daily, and the cells were passaged every 5-7 days either by manual cutting of clumps using 27 g needles (only at passages 1-3) or by gentle pipetting using 200 ml Gilson pipette tips. Alternatively, the cells were passaged using trypsin EDTA (0.25%, Biological Industries, Beit Haemek, Israel) combined with a one-hour treatment with 10 M ROCK inhibitor (EMD Biosciences, Inc. La Jolla, CA, USA) before the incubation with trypsin. For calculating cells' doubling time the I3, I4 and H9.2 hESCs and the J1.2-3 and iF4 iPS cells were counted and grown in suspension for 8 days with CM100F or CM100Fp culture media. Cells were counted every other day. Average doubling time of four biological repeats was calculated.

Culture in spinner flasks (3-dimensional)—iPS cells or hESCs clumps were cultured in static Petri dishes for at least one passage, and were then transferred to 250 ml spinner flasks (Cell Spin 250 or 100, Integra BioSciences) in the tested culture media, shaken continuously at 90 rounds per minutes (rpm) using a magnetic plate, and placed in a 37° C. in 5% CO$_2$ incubator. Medium was changed every other day. Every 5-7 days the clumps were split with a ratio of 1:2.

Immunofluorescence of cells cultured on 2-D or 3-D culture systems—For fluorescent immunostaining undifferentiated hESCs or iPS grown in 2-D or 3-D culture systems in the presence of the tested culture media or re-cultured on MEFs were fixed with 4% paraformaldehyde and exposed to the primary antibodies overnight at 4° C. Cys 3 conjugated antibodies (Chemicon International, Temecula CA, USA) were used as secondary antibodies (1:200). The primary antibodies (1:50) include SSEA 1, 3 and 4 (Hybridoma Bank, Iowa, USA), TRA1-60 and TRA-1-81 (Chemicon International, Temecula CA, USA) and Oct4 (Santa Cruz Biotechnology. Santa Cruz, CA, USA).

Immunohistochemistry of iPS cells or hESCs cultured on 2-D or 3-D culture systems—After deparaffinization the tissue sections were stained using Dako LSAB+ staining kit for presence of markers of ectoderm (β-3-tubulin 1:500, Chemicon International, Temecula CA USA), mesoderm (CD31 1:20), and endoderm (α-fetoprotein 1:20) (both from DakoCytomation, Glostrup, Denmark). As controls, both IgG isotype and secondary antibody staining were performed. The secondary antibody was conjugated to peroxidase.

Karyotype analysis of cells cultured on 2-D or 3-D culture systems—Karyotype analysis (G-banding) was performed on at least 10 cells from each sample, two samples per test, as previously described [Amit et al, 2003]. Karyotypes were analyzed and reported according to the "International System for Human Cytogenetic Nomenclature" (ISCN).

Embryoid bodies (EBs) formation of cells cultured on 2-D or 3-D culture systems—For the formation of EBs, hESCs or iPS were passaged as described and transferred to 58 mm Petri dishes (Greiner, Frickenhausen, Germany). EBs were grown in medium consisting of 80% DMEM/F12 (Biological Industries, Beit Haemek, Israel), supplemented with 10% fetal bovine serum (FBS) (HyClone, Utah, USA), 10% KNOCKOUT™ serum replacement (SR; Invitrogen), 2 mM L-glutamine, 0.1 mM β-mercaptoethanol, and 1% non-essential amino acid stock (Invitrogen Corporation, Grand Island NY, USA). 10-14 day-old EBs were harvested for RNA isolation and histological examination. For histological analysis EBs were fixed in 10% neutral-buffered formalin, dehydrated in graduated alcohol (70%-100%) and embedded in paraffin. □ 1-5 µm sections were deparaffinized and stained with hematoxylin/eosin (H&E).

RT-PCR of cells cultured on 2-D or 3-D culture systems—Total RNA was isolated from hESCs or iPS grown for 10, 15 and 20 passages on the xeno-free two-dimensional or three-dimensional culture systems in the tested media and from 10-14 day-old EBs (formed from cells grown on 2-D, 3-D in the presence of the tested culture media or cells cultured on MEFs) using Tri-Reagent (Sigma, St. Louis MO, USA), according to the manufacturer's instructions. cDNA was synthesized from 1 µg total RNA using MMLV reverse transcriptase RNase H minus (Promega, Madison WI. USA). PCR reaction included denaturation for 5 minutes at 94° C. followed by repeated cycles of 94° C. for 30 seconds, annealing temperature as indicated in Table 1, hereinbelow, for 30 seconds and extension at 72° C. for 30 seconds. PCR primers and reaction conditions are described in Table 1, hereinbelow. PCR products were size-fractionated using 2% agarose gel electrophoresis. DNA markers were used to confirm the size of the resultant fragments. For quantitative PCR (Q-PCR), densitometry of tested genes was normalized to GAPDH. Three repeats were conducted for each tested line.

TABLE 1

RT-PCR primers and conditions
Table 1: RT-PCR primers and PCR conditions are provided along with the GenBank Accession numbers of the amplified transcripts.

| Gene product (Accession number) | Forward (F) and reverse (R) primers (SEQ ID NO:) provided in a 5'→3' direction | Reaction Condition | Size (bp) |
|---|---|---|---|
| Oct-4 (S81255) | F: 5'-GAGAACAATGAGAACCTTCAGGA (SEQ ID NO: 1.)<br>R: 5'-TTCTGCGCCGGTTACAGAACCA (SEQ ID NO: 2) | 30 cycles at 60° C. in 1.5 mM MgCl$_2$ | 219 |
| Albumin (AF542069) | F: 5'-TGCTTGAATCAGCTGATGACAGGG (SEQ ID NO: 3)<br>R: 5'-AAGGCAAGTCAGCAGCCATGTCAT (SEQ ID NO: 4) | 35 cycles at 60° C. in 1.5 mM MgCl$_2$ | 302 |
| α-fetoprotein (BC027881) | F: 5'-GCTGGATTCTTCTGCAGGATGGGGAA (SEQ ID NO: 5)<br>R: 5'-TCCCCTGAAGAAAATTGGTTAAAAT (SEQ ID NO: 6) | 30 cycles at 60° C. in 1.5 mM MgCl$_2$ | 216 |
| NF-68KD (NFH (AY156690; X15307; X15309) | F: 5'-GAGTGAAATGGCACGATACCTA (SEQ ID NO: 7)<br>R: 5'-TTTCCTCTCCTTCTTCACCTTC (SEQ ID NO: 8) | 30 cycles at 60° C. in 2 mM MgCl$_2$ | 473 |
| α-cardiac actin (NM_005159) | F: 5'-GGAGTTATGGTGGGTATGGGTC (SEQ ID NO: 9)<br>R: 5'-AGTGGTGACAAAGGAGTAGCCA (SEQ ID NO: 10) | 35 cycles at 65° C. in 2 mM MgCl$_2$ | 486 |
| β-Actin (NM_001101) | F: 5'-ATCTGGCACCACACCTTCTACAATGAGCTGCG (SEQ ID NO: 11)<br>R: 5'-CGTCATACTCCTGCTTGCTGATCCACATCTGC (SEQ ID NO: 12) | 35 cycles at 62° C. in 1.5 mM MgCl$_2$ | 838 |

TABLE 1-continued

RT-PCR primers and conditions
Table 1: RT-PCR primers and PCR conditions are provided along with the GenBank Accession numbers of the amplified transcripts.

| Gene product (Accession number) | Forward (F) and reverse (R) primers (SEQ ID NO:) provided in a 5'→3' direction | Reaction Condition | Size (bp) |
|---|---|---|---|
| Sox2 (Z31560) | F: 5'CCCCCGGCGGCAATAGCA (SEQ ID NO: 13)<br>R: 5'TCGGCGCCGGGGAGATACAT (SEQ ID NO: 14) | 35 cycles at 60° C. in 1.5 mM $MgCl_2$ | 448 |
| Rex1 (AF450454) | F: 5'GCGTACGCAAATTAAAGTCCAGA (SEQ ID NO: 15)<br>R: 5'CAGCATCCTAAACAGCTCGCAGAAT (SEQ ID NO: 16) | 35 cycles at 56° C. in 1.5 mM $MgCl_2$ | 306 |
| CX43 (NM_000165) | F: 5'TACCATGCGACCAGTGGTGCGCT (SEQ ID NO: 17)<br>R: 5'GAATTCTGGTTATCATCGGGGAA (SEQ ID NO: 18) | 35 cycles at 61° C. in 1.5 mM $MgCl_2$ | 295 |
| FGF4 (NM_002007) | F: 5'CTACAACGCCTACGAGTCCTACA (SEQ ID NO: 19)<br>R: 5'GTTGCACCAGAAAAGTCAGAGTTG (SEQ ID NO: 20) | 35 cycles at 52° C. in 1.5 mM $MgCl_2$ | 370 |
| Glucagon (X03991) | F: 5'CTCAGTGATCCTGATCAGATGAACG (SEQ ID NO: 21)<br>R: 5'AGTCCCTGGCGGCAAGATTATCAAG (SEQ ID NO: 22) | 35 cycles at 65° C. in 1.5 mM $MgCl_2$ | 370 |
| β-globulin (V00499) | F: 5'ACCTGACTCCTGAGGAGAAGTCTGC (SEQ ID NO: 23)<br>R: 5'TAGCCACACCAGCCACCACTTTCTG (SEQ ID NO: 24) | 35 cycles at 65° C. in 1.5 mM $MgCl_2$ | 410 |
| Flk1 (NM_002253) | F: 5'ATGCACGGCATCTGGGAATC (SEQ ID NO: 25)<br>R: 5'GCTACTGTCCTGCAAGTTGCTGTC (SEQ ID NO: 26) | 35 cycles at 65° C. in 1.5 mM $MgCl_2$ | 537 |
| AC133 (NM_006017) | F: 5'CAGTCTGACCAGCGTGAAAA (SEQ ID NO: 27)<br>R: 5'GGCCATCCAAATCTGTCCTA (SEQ ID NO: 28) | 35 cycles at 65° C. in 1.5 mM $MgCl_2$ | 200 |
| Nanog (NG_004095) | F: 5'ACTAACATGAGTGTGGATCC (SEQ ID NO: 29)<br>R: 5'TCATCTTCACACGTCTTCAG (SEQ ID NO :30) | 35 cycles at 61° C. in 1.5 mM $MgCl_2$ | 800 |

Teratoma formation from cells cultured on 2-D—hESCs (H9.2 and I3) and iPS (iF4 and J1.2-3) cells from 4-6 wells of a 6-well plate (each well has 10 cm total surface area and includes $1.5-2.5 \times 10^6$ cells) were harvested and injected into the hindlimb muscles of four week-old male of severe combined immunodeficiency (SCID)-beige mice. Ten weeks after the injection the resultant teratomas were harvested and prepared for histological analysis using the same method mentioned for EBs.

Teratoma formation from cells cultured in suspension (3-D culture systems)—hESCs (H9.2 and 13) and iPS (iF4 and J1.2-3) cells from four to six 58 mm dishes (from suspension culture, each dish includes $1.5-2.5 \times 10^6$ cells) were harvested and injected into the hindlimb muscles of four week-old male of severe combined immunodeficiency (SCID)-beige mice. Ten weeks after the injection the resultant teratomas were harvested and prepared for histological analysis using the same method mentioned for EBs.

Example 1

Induced Pluripotent Stem Cells and Embryonic Stem Cells can be Maintained in an Undifferentiated and Pluripotent State when Cultured on Xeno-Free, Feeder-Layer-Free 2-D Culture Systems The experiments described hereinbelow were performed using iPS cells or hESCs which were cultured according to the methods, culturing conditions and culture media described in the "General Materials and Experimental Methods" section above.

Experimental Results iPS cells and human ESCs cultured on 2D culture systems using xeno-free, serum-free medium and supportive-layers free system exhibit undifferentiated morphology and characteristics typical to iPS or hESCs—Several possible medium combinations (HA74/1, HA75, HA76, HA77, HA78, HA40\4) were tested for the ability to support feeder-layer free and xeno-free (devoid of any animal contaminant) cultures of iPS cells or hESCs. All tested media (i.e., HA74/1, HA75, HA76, HA77, HA78, HA40\4) were found suitable for supporting iPS or hESC cultures for at least 15 passages. Using the tested media under feeder-layer free conditions using a Matrigel™ synthetic matrix iPS cells or hESCs were cultured continuously for at least 15 passages while maintaining their iPS of hESCs features including undifferentiated proliferation, karyotype stability and pluripotency (data not shown). No morphological differences could be observed between colonies grown in the tested culture systems and those grown on MEF in the presence of the yF10 medium, correspondingly, morphological features remained unchanged on a single-cell level, rendering cells small and round, exhibiting high nucleus-to-cytoplasm ratio, with a notable presence of one to three nucleoli and typical spacing between the cells (data not shown). Similar to cells grown on MEFs in the presence of a control medium (yF10 basic culture medium)), iPS cells or hESCs which were cultured on a Matrigel™ (BD Bioscience) synthetic matrix in the presence of all of the tested media (HA74/1, HA75, HA76, HA77, HA78, HA40\4) were passaged routinely every five to seven days, at the same ratio of 1 to 2, 2 to 3, or 1 to 3, indicating a similar population doubling time as iPS or hESCs grown on MEFs with the control medium. The iPS cells or the hESCs were passaged at a same seeding efficiency of about 1 million cells per 10 cm$^2$, with the same viability rate of over 90%. Using 15% serum replacement (SR) and 10% DMSO, the iPS cells or the hESCs were successfully frozen and thawed.

iPS cells or hESCs cultured on 2D culture systems in animal free medium and supportive layer free system express markers of pluripotency—Several surface markers typical of primate undifferentiated ESCs and iPS cells were examined using immunofluorescent staining [as described in Thomson et al, 1995, 1996, 1998]. Cells cultured with the tested media for at least 15 passages were found to be strongly positive to surface markers SSEA4, TRA-1-60, TRA-1-81 and Oct 4 (data not shown). As in other primate ESCs, staining with SSEA3 was weak and staining for SSEA1 was negative (data not shown).

iPS cells or hESCs cultured on 2D culture systems in animal free medium and supportive layer free systems form EBs in vitro and teratomas in vivo—The developmental potential of the cells after prolonged culture in the tested conditions was examined in vitro by the formation of embryoid bodies (EBs). iPS or hESCs cells cultured in feeder layer-free culture systems in the presence of the tested culture media (HA74/1, HA75, HA76, HA77, HA78, HA40\4) formed EBs similar to those created by ESCs grown on MEFs (data not shown). For example, the ability of iPS cells to form EBs was shown after 28 passages in the HA40/4 medium and 20 passages in the HA77 medium. Within these EBs, the iPS cells or the hESCs differentiated into cell types representative of the three embryonic germ layers [Itskovitz-eldor et al, 2000]. Following their injection to SCID Beige mice, the iPS cells or the hESCs cultured under the tested conditions formed teratomas containing cell types representative of the three embryonic germ layers (data not shown), thus demonstrating their full pluripotency. For example, the ability of iPS cells to form teratomas was shown after 31 passages in the mHA40/4 medium; after 24 passages in the HA74/1 medium; and after 16 passages in the HA77 medium.

Example 2

Induced Pluripotent Stem Cells and Embryonic Stem Cells can be Maintained in an Undifferentiated and Pluripotent State When Cultured on Xeno-Free Feeder-Layers in the Presence of Xeno-Free and Serum-Free Medium The experiments described hereinbelow were performed using iPS cells or hESCs which were cultured according to the methods, culturing conditions and culture media described in the "General Materials and Experimental Methods" section above.

Experimental Results iPS cells or hESCs cultured on 2D culture systems using xeno-free, serum-free medium and xeno-free feeder cell layers exhibit undifferentiated morphology and characteristics typical to iPS or hESCs—Several possible medium combinations (HA74/1, HA75, HA76, HA77, HA78, HA40\4) were tested for the ability to support xeno-free (devoid of any animal contaminant) cultures of iPS or hESCs using foreskin fibroblast as feeders cell layers. All tested media were found suitable for supporting iPS or hESC cultures. Using the tested media under xeno-free conditions with foreskin fibroblasts as supportive layer, iPS cells or hESCs were cultured continuously for at least 22 passages while maintaining their iPS or hESCs features including undifferentiated proliferation (FIGS. 1A-C and data not shown), karyotype stability and pluripotency. No morphological differences could be observed between colonies grown in the tested culture systems and those grown on MEF in the presence of the control yF10 medium, correspondingly, morphological features remained unchanged on a single-cell level, rendering cells small and round, exhibiting high nucleus-to-cytoplasm ratio, with a notable presence of one to three nucleoli and typical spacing between the cells (data not shown). Similar to cells grown on MEFs, iPS cells or hESCs cultured on foreskin fibroblast feeder cells in the presence of all the tested culture media (HA74/1, HA75, HA76, HA77, HA78, HA40\4) were passaged routinely every five to seven days, at the same ratio of 1 to 2, 2 to 3 or 1 to 3, indicating a similar population doubling time as iPS or hESCs grown on MEFs in the presence of a control yF10 medium. The iPS cells or the hESCs were passaged at a same seeding efficiency of about 1 million cells per 10 cm$^2$, with the same viability rate of over 90%. Using 15% serum replacement (SR) and 10% DMSO, the iPS cells or the hESCs were successfully frozen and thawed.

iPS cells or hESCs cultured on 2D culture systems in animal free medium and xeno-free supportive layer express markers of pluripotency—Several surface markers typical of primate undifferentiated ESCs and iPS cells were examined using immunofluorescent staining [as described in Thomson et al, 1995, 1996, 1998]. Cells cultured with the tested media for at least 15 passages were found to be strongly positive to surface markers SSEA4, TRA-1-60, TRA-1-81 and Oct 4 (FIGS. 2A-C). As in other primate ESCs, staining with SSEA3 was weak and staining for SSEA1 was negative (data not shown).

iPS cells or hESCs cultured on 2D culture systems in animal free medium and xeno-free feeder layers form EBs in vitro and teratomas in vivo—The developmental potential of the cells after prolonged culture in the tested conditions was examined in vitro by the formation of embryoid bodies (EBs). iPS cells or hESCs cultured in xeno-free feeder cell layers (foreskin fibroblasts) in the presence of the tested culture media (HA74/1, HA75, HA76, HA77, HA78, HA40\4) formed EBs similar to those created by ESCs grown on MEFs in the presence of the yF10 control medium (data not shown). Within these EBs, the iPS cells or hESCs differentiated into cell types representative of the three embryonic germ layers [Itskovitz-Eldor et al, 2000]. Following their injection to SCID Beige mice, the iPS cells or hESCs cultured under the tested conditions form teratomas containing cell types representative of the three embryonic germ layers (data not shown), thus demonstrating their full pluripotency.

Example 3

Derivation of an Embryonic Stem Cell Line on the Xeno-Free Culture Medium of the Invention After digestion of the zona pellucida by Tyrode's acidic solution (Sigma, St Louis, MO, USA), whole blastocysts were placed on mitotically inactivated human foreskin fibroblasts (HFF) in the presence of the HA40/4 medium, except that the medium did not contain sodium bicarbonate. Initially, the cells were passage mechanically by using insulin syringes (BD plastipak, Cat. No. 300013) and after 4 passages the cells were passaged every four to six days using 1 mg/ml type IV collagenase (Gibco Invitrogen corporation products, San Diego, CA, USA). The resulting human ESC line was designated "WC1".

Example 4

Induced Pluripotent Stem Cells and Embryonic Stem Cells can be Maintained in an Undifferentiated and Pluripotent State in Static Suspension Cultures Culture of iPS cells in suspension holds significant advantages over conventional cultures, particularly when aiming to obtain large amounts of cells for cell and tissue transplantation.

The experiments described hereinbelow were performed using iPS cells or hESCs which were cultured according to the methods, culturing conditions and culture media described in the "General Materials and Experimental Methods" section above.
Experimental Results iPS cells can be maintained in an undifferentiated state in suspension cultures—The iPS cells (the J1.2-3 and iF4 cell lines) which were grown with MEF or in feeder layer-free conditions [Amit et al, 2004], were placed in suspension cultures. After 24 hours in suspension culture with the tested culture medium CM100F, CM100Fp, yFL3 (which comprises 4 ng/ml or 10 ng/ml bFGF and supplemented with 3000 units/ml LIF), or yF100, the iPS cells created spheroid clumps or disc-like structures which were maintained for at least 20 passages (FIGS. 3A-C and data not shown). Histological examination of the iPS that were cultured in suspension for at least 10 passages revealed a homogenous population of small cells with large nuclei. The spheroids grew and were split mechanically every 5-7 days while maintaining their morphology, allowing expansion of the suspension cultures. Alternatively, by using trypsin-EDTA and ROCK inhibitor treatment, suspended cells could be dissociated into single cells and still formed spheroids of the same morphology and features, thus allowing efficient cell expansion. Some cultures were carried out for over 50 passages (a year of continuous culture). The two different iPS cell lines, J1.2-3 and iF4, which were cultured in suspension as described herein with the tested culture media, showed similar behavior and spheroid morphology and histology.

The yF100 medium (the yF10 basic culture medium which includes 100 ng/ml bFGF instead of 10 ng/ml), the CM100Fp and the yFL3 (the yF10 basic culture medium including 4 ng/ml bFGF instead of 10 ng/ml and supplemented with 3000 units/ml LIF) were found to support the growth of human ESCs in suspension culture in a proliferative, undifferentiated and pluripotent state.

iPS cells which were cultured in suspension and were re-cultured on 2-D culture systems maintain typical iPS cell colony morphology—After at least 10 passages in suspension, when returned to 2D culture with MEFs or fibronectin surface, all of the spheroid clumps adhered to the MEFs or fibronectin surface and after 24-48 hours demonstrated typical iPS cells colony morphology, exhibiting high nucleus-to-cytoplasm ratio with a notable presence of one to three nucleoli and with typical spacing between the cells (FIG. 4).

iPS cells maintain their undifferentiated stem cell phenotype while being cultured in suspension cultures (3D cultures)—Several surface markers typical of primate undifferentiated ESCs and iPS cells were examined using immunofluorescent staining [as described in Thomson et al, 1998; Bhattacharya, et al. 2004; Kristensen et al, 2005]. Human iPS cells which were cultured in suspension with the tested culture media for at least 30 passages were found to be strongly positive for SSEA4, TRA-1-60 and TRA-1-81 and Oct 4 (FIGS. 5A-C). As with other primate ESCs [Thomson et al., 1995 and 1996] and with ESCs cultured with MEFs, staining with SSEA3 was weak and negative for SSEA1 data not shown). Staining for stem cell markers remained high when cells cultured in suspension were returned to 2D cultures with MEFs (data not shown). RT-PCR analyses showed that, similarly to cells cultured with MEFs, iPS cells cultured in suspension for at least 10 passages expressed genetic markers of pluripotency [King et al, 2006] including Oct 4, Nanog, Sox2, Rex1, and FGF4 (data not shown). No significant difference in gene expression of Oct 4, Nanog, Sox2, Rex1, and FGF4 was detected between iPS cells cultured in suspension as compared with iPS cells cultured on MEF, nor with iPS cells that were re-cultured with MEFs after continuous culture in suspension, similar to hESCs under the same conditions.

iPS cells which are cultured in suspension maintain normal karyotype—Karyotype analysis by Giemsa banding was carried out on cells after 30 passages in suspension, and the cells were found to exhibit normal 46,XY karyotype (data not shown). Thus, the karyotype of the suspension cell culture remained stable.

iPS cells or hESCs which are cultured in suspension maintain their pluripotency in vitro—Following prolonged expansion in suspension cultures with the tested culture media, iPS cells or hESCs preserved their pluripotent differentiation ability as was shown by the in vitro formation of EBs. When hESCs or iPS cells which were cultured in suspension for over 20 passages were transferred to serum-containing medium without the addition of the growth factors, formation of cystic EBs was observed after 7-10 days, similarly to cavitated EBs formed from hESCs following 10 days in culture [Itskovitz et al, 2000], and cystic EBs after 14-20 days. Within the EBs formed from the iPS cells or hESCs, there were cell types representative of the three embryonic germ layers typical of iPS cells differentiation (data not shown).

For example, the ability of iPS cells to form EBs was shown after 22 passages in the presence of the CM100p medium in a suspension culture; the ability to form EBs was shown after 23 passages in the presence of the yF100 medium in a suspension culture; the ability to form EBs was shown after 8 passages in the presence of the yFL3 medium in a suspension culture.

iPS cells which are cultured in suspension maintain their pluripotency in vivo—Pluripotency of the suspension iPS cells was further demonstrated in vivo by teratoma formation. Cells cultured in suspension for at least 20 passages were injected into SCID Beige mice, and 10 weeks later tumors were formed (data not shown). Within these teratomas, tissues representative of the three germ layers were observed.

For example, the ability of iPS cells to form teratomas was shown after 20 passages in the CM100 in a suspension culture; and the ability to form teratomas was shown after 10 passages in the yFL3 in a suspension culture.

Example 5

Induced Pluripotent Stem Cells and Embryonic Stem Cells can be Maintained in an Undifferentiated and Pluripotent State in Dynamic Suspension Cultures The experiments described hereinbelow were performed using iPS cells or hESCs which were cultured according to the methods, culturing conditions and culture media described in the "General Materials and Experimental Methods" section above.
Experimental Results iPS cells which are cultured in shaking suspension cultures maintain their undifferentiated state—iPS cells from line J1.2-3 or hESCs were cultured in suspension in spinner flasks for at least one month using the tested culture media. An examination after one month showed that the morphological characteristics of the spheroid clumps formed by the cells remained similar to those observed when iPS cells are cultured statically in Petri dishes (data not shown). In addition, the iPS cells strongly expressed markers of undifferentiated hESCs such as Oct-4, TRA-1-81, TRA-1-60 and SSEA4 (FIGS. 6A-D). When re-cultured on MEFs, the iPS cells in the clumps re-attached, forming again typical colonies of iPS cells (data not shown). The karyotype of the cells cultured for one month in the spinner flask was found to be normal (data not shown).

iPS cells which are cultured in dynamic suspension cultures maintain normal karyotype—IPS cells or hESCs which were cultured for 30 passages in static suspension cultures (in the presence of the tested culture media) and then for 3 passages in dynamic (spinner) suspension (in the presence of the tested culture media) were found to exhibit normal 46,XY karyotype. Thus, the karyotype of the suspension iPS cell culture remained stable.

iPS cells of hESCs which are cultured in dynamic suspension maintain their pluripotency in vitro—The developmental potential of the iPS cells or hESCs that were cultured in dynamic suspension cultures was examined in vitro by the formation of EBs, hESCs or iPS were cultured in static suspension for over 20 passages, then on dynamic suspension for at least additional 10 passages, and then were transferred to serum-containing medium without the addition of the growth factors, and the formation of cystic EBs was observed after 7-10 days, similarly to cavitated EBS formed from hESCs following 10 days in culture [Itskovitz et al, 2000], and cystic EBs after 14-20 days. Within the EBs formed from hESCs or iPS cells there were cell types representative of the three embryonic germ layers typical of iPS cells differentiation (data not shown).

iPS cells or hESCs which are cultured in dynamic suspension maintain their pluripotency in vivo—Pluripotency of iPS cells or hESCs cultured in dynamic suspension demonstrated in vivo by teratoma formation. Cells were cultured in static suspension for at least 20 passages and then in dynamic suspension for additional 10 passages and then were injected into SCID Beige mice. Following 10 weeks of injection into the mice tumors were formed. Within these teratomas, tissues representative of the three germ layers were observed (data not shown).

This study presents a novel approach for culturing undifferentiated iPS cells or human ESCs using either defined 2D culture system or suspension cultures. The present inventors demonstrate that under these conditions two iPS cell lines, one derived from adult fibroblasts and one derived from foreskin fibroblast could be grown and expanded through many passages while maintaining their features including pluripotency and stable karyotypes. When iPS cells are transferred to suspension in the presence of a differentiating medium (e.g., DMEM/F12 supplemented with 10% fetal bovine serum (FBS), 10% KNOCKOUT™ serum replacement, 2 mM L-glutamine, 0.1 mM β-mercaptoethanol, and 1% non-essential amino acid stock), they spontaneously form embryoid bodies (EBs). On the other hand, using the tested culture systems (e.g., in the presence of the CM100F, CM100Fp, yF100 or yFL3 culture media) iPS cells spontaneously form spheroids consisting undifferentiated cells.

This is the first description of a method for continuous expansion of undifferentiated iPS in 3D suspension and shaking cultures, which could be adequately applied for large-scale cell production.

The inventors present for the first time a suspension culture system for expansion of undifferentiated iPS, based on serum free medium and defined growth factors. This suspension culture system utilizes either Petri dishes, shaking Erlenmeyer, or spinner flasks. Two iPS cell lines from adult skin and newborn foreskin fibroblast were cultured according to the novel method of the invention as small spheroids which maintain all typical ESC/iPS cells features following prolonged culture of over 25 passages (86 doublings), including stable karyotype and pluripotency. These results demonstrate that culturing iPS cells in a defined medium without feeder layer using 3D culture is possible.

In addition, when applied onto a dynamic system for one month, the number of cell clumps of both hESCs and human iPS cells increased in folds while maintaining the cells unique characteristics. These results render the proposed suspension system suitable for both the routine culture of iPS cells or hESCs in 3D and for mass production of iPS cells and hESCs for therapeutic ends.

The teachings of the invention present scalable, reproducible and controlled culture systems. These results present a significant progress towards the desired end goal of obtaining a facilitator method for large-scale culture of undifferentiated iPS cells and hESCs needed for both clinical and industrial uses.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

Additional References are Cited in Text

Amit, M., Shariki, K., Margulets, V., & Itskovitz-Eldor, J. (2004). Feeder and serum-free culture system for human embryonic stem cells. Biol. Reprod. 70, 837-845.

Amit M, Margulets V, Segev H, Shariki K, Laevsky I, Coleman R, Itskovitz-Eldor J. 2003. Biol Reprod. 68(6): 2150-6. Human feeder layers for human embryonic stem cells.

Aoi T, Yae K, Nakagawa M, Ichisaka T, Okita K, Takahashi K, Chiba T, Yamanaka S. Generation of Pluripotent Stem Cells from Adult Mouse Liver and Stomach Cells. Science. 2008.

Bhattacharya, B. et al. (2004). Gene expression in human embryonic stem cell lines: unique molecular signature. Blood 103,2956-2964.

Hanna J, Wernig M, Markoulaki S, Sun C W, Meissner A, Cassady J P, Beard C, Brambrink T, Wu L C, Townes T M, Jaenisch R. Treatment of sickle cell anemia mouse model with iPS cells generated from autologous skin. Science. 2007, 318(5858):1920-1923.

Itskovitz-Eldor, J., Schuldiner, M., Karsenti, D., Eden, A., Yanuka, O., Amit, M., Soreq, H., Benvenisty, N. (2000). Differentiation of human embryonic stem cells into embryoid bodies comprising the three embryonic germ layers. Mol. Med. 6, 88-95.

King, T. D., Gandy, J. C. & Bijur, G. N. (2006). The protein phosphatase-1/inhibitor-2 complex differentially regulates GSK3 dephosphorylation and increases sarcoplasmic/endoplasmic reticulum calcium ATPase 2 levels. Exp. Cell Res. 312, 3693-3700.

Kristensen, D. M., Kalisz, M., & Nielsen, J. H. (2005). Cytokine signaling in embryonic stem cells. APMIS. 113, 756-772.

Lowry W E, Richter L, Yachechko R, Pyle A D, Tchieu J, Sridharan R, Clark A T, Plath K. Generation of human induced pluripotent stem cells from dermal fibroblasts. Proc Natl Acad Sci USA, 2008, 105(8):2883-2888.

Ludwig T E., et al., 2006 (Nature Biotechnology, 24: 185-7)

Meissner A, Wernig M, Jaenisch R. Direct reprogramming of genetically unmodified fibroblasts into pluripotent stem cells. Nat Biotechnol. 2007, 25(10):1177-1181.

Okita K., et al, 2007. Generation of germline-competent induced pluripotent stem cells. Nature 448: 313-318.

Nakagawa M, Koyanagi M, Tanabe K, Takahashi K, Ichisaka T, Aoi T, Okita K, Mochiduki Y, Takizawa N, Yamanaka S. Generation of induced pluripotent stem cells without Myc from mouse and human fibroblasts. Nat Biotechnol. 2008, 26(1):101-106.

Park I H, Zhao R, West J A, Yabuuchi A, Huo H, Ince T A, Lerou P H, Lensch M W, Daley G Q. Reprogramming of human somatic cells to pluripotency with defined factors. Nature. 2008, 451(7175):141-146.

Takahashi K, Yamanaka S. Induction of pluripotent stem cells from mouse embryonic and adult fibroblast cultures by defined factors. Cell. 2006, 126(4):663-676.

Takahashi K, Tanabe K, Ohnuki M, Narita M, Ichisaka T, Tomoda K, Yamanaka S. Induction of pluripotent stem cells from adult human fibroblasts by defined factors. Cell. 2007, 131(5):861-872.

Thomson, J. A., Itskovitz-Eldor, J., Shapiro. S. S., Waknitz, M. A., Swiergiel, J. J., Marshall, V. S., Jones, J. M. (1998). Embryonic stem cell lines derived from human blastocysts. Science 282, 1145-1147.

Thomson, J. A., Kalishman, J., Golos, T. G., Durning, M., Harris, C. P., Becker, R. A., Hearn, J. P. (1995). Isolation of a primate embryonic stem cell line. Proc. Natl. Acad. Sci. USA. 92, 7844-7848.

Thomson, J. A., Kalishman, J., Golos, T. G., Durning, M., Harris, C. P., Hearn, J. P. (1996). Pluripotent cell lines derived from common marmoset (Callithrix jacchus) blastocysts. Biol. Reprod. 55, 254-259.

Yu, Y., Vodyanik M A., Smuga-Otto K., et al., 2007. Science, 318, 1917-1920.

Yu J, et al., 2009; Science. 2009, 324: 797-801.

---

What is claimed is:

1. A culture medium comprising a cytokine consisting of an IL6RIL6 chimera at a concentration range of about 50-200 picogram per milliliter (pg/ml), wherein said IL6RIL6 chimera includes the amino acid sequence set forth by SEQ ID NO: 39, wherein the culture medium is serum-free and capable of maintaining pluripotent stem cells in an undifferentiated state in the absence of feeder cell support for at least 5 passages.

2. The culture medium of claim 1, wherein said culture medium further comprises serum replacement.

3. The culture medium of claim 1, wherein said concentration of said IL6RIL6 chimera is between about 90 pg/ml to about 120 pg/ml.

4. The culture medium of claim 1, wherein said concentration of said IL6RIL6 chimera is about 100 pg/ml.

5. The culture medium of claim 1, wherein said culture medium further comprises basic fibroblast growth factor (bFGF).

6. A cell culture comprising pluripotent stem cells and the culture medium of claim 1.

7. The cell culture of claim 6, wherein the cell culture is feeder cells free.

8. The cell culture of claim 6, wherein said pluripotent stem cells are embryonic stem cells.

9. The cell culture of claim 6, wherein said pluripotent stem cells are induced pluripotent stem (iPS) cells.

10. The cell culture of claim 6, wherein said pluripotent stem cells are human pluripotent stem cells.

11. The cell culture of claim 6, being a suspension culture.

12. The culture medium of claim 1, wherein the culture medium is capable of maintaining a population of cells consisting of induced pluripotent stem cells having a normal karyotype for at least 15 passages.

13. A method of deriving an embryonic stem cell line, comprising (a) obtaining an embryonic stem cell from a pre-implantation stage blastocyst, post-implantation stage blastocyst and/or a genital tissue of a fetus; and (b) culturing said embryonic stem cell in the culture medium of claim 1;

thereby deriving the embryonic stem cell line.

14. A method of deriving an induced pluripotent stem cell line, comprising (a) inducing a somatic cell to a pluripotent stem cell; and (b) culturing said pluripotent stem cell in the culture medium of claim 1;

thereby deriving the induced pluripotent stem cell line.

15. A method of generating lineage-specific cells from pluripotent stem cells, the method comprising:

(a) culturing the pluripotent stem cells in the culture medium of claim 1, to thereby obtain expanded, undifferentiated stem cells;

(b) subjecting said expanded, undifferentiated stem cells to culturing conditions suitable for differentiating and/or expanding lineage specific cells;

thereby generating the lineage-specific cells from the pluripotent stem cells.

16. A method of generating embryoid bodies from pluripotent stem cells, the method comprising:

(a) culturing the pluripotent stem cells in the culture medium of claim 1, to thereby obtain expanded, undifferentiated pluripotent stem cells; and (b) subjecting said expanded, undifferentiated pluripotent stem cells to culturing conditions suitable for differentiating said stem cells to embryoid bodies;

thereby generating the embryoid bodies from the pluripotent stem cells.

17. A method of generating lineage-specific cells from pluripotent stem cells, the method comprising:

(a) culturing the pluripotent stem cells in the culture medium of claim 1, to thereby obtain expanded, undifferentiated pluripotent stem cells;

(b) subjecting said expanded, undifferentiated pluripotent stem cells to culturing conditions suitable for differentiating said expanded, undifferentiated stem cells to embryoid bodies; and (c) subjecting cells of said embryoid bodies to culturing conditions suitable for differentiating and/or expanding lineage specific cells;

thereby generating the lineage-specific cells from the pluripotent stem cells.

18. A method of expanding and maintaining pluripotent stem cells in an undifferentiated state, the method comprising culturing the pluripotent stem cells in the culture medium of claim 1, thereby expanding and maintaining the pluripotent stem cells in the undifferentiated state.

19. The method of claim 18, wherein said culturing is effected on a matrix.

20. The method of claim 18, wherein said culturing is effected in a suspension culture.

21. The method of claim 18, wherein said culture medium is protein carrier-free.

\* \* \* \* \*

SEQUENCE LISTING

```
<160> NUMBER OF SEQ ID NOS: 39

<210> SEQ ID NO 1
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 1
gagaacaatg agaaccttca gga                                           23

<210> SEQ ID NO 2
<211> LENGTH: 23
<212> TYPE: DNA
```

<213> ORGANISM: Artificial sequence
<220> FEATURE:
<223> OTHER INFORMATION: Single strand DNA oligonucleotide

<400> SEQUENCE: 2
ttctggcgcc ggttacagaa cca                                    23

<210> SEQ ID NO 3
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 3
tgcttgaatg tgctgatgac aggg                                   24

<210> SEQ ID NO 4
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 4
aaggcaagtc agcagccatc tcat                                   24

<210> SEQ ID NO 5
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 5
gctggattgt ctgcaggatg gggaa                                  25

<210> SEQ ID NO 6
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 6
tcccctgaag aaaattggtt aaaat                                  25

<210> SEQ ID NO 7
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 7
gagtgaaatg gcacgatacc ta                                     22

<210> SEQ ID NO 8
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 8
tttcctctcc ttcttcacct tc                                     22

```
<210> SEQ ID NO 9
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 9
ggagttatgg tgggtatggg tc                                         22

<210> SEQ ID NO 10
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 10
agtggtgaca aaggagtagc ca                                         22

<210> SEQ ID NO 11
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 11
atctggcacc acaccttcta caatgagctg cg                              32

<210> SEQ ID NO 12
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 12
cgtcatactc ctgcttgctg atccacatct gc                              32

<210> SEQ ID NO 13
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 13
cccccggcgg caatagca                                              18

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 14
tcggcgccgg ggagatacat                                            20

<210> SEQ ID NO 15
<211> LENGTH: 23
<212> TYPE: DNA
<213> ORGANISM: Artificial sequence
<220> FEATURE:
```

<223> OTHER INFORMATION: Single strand DNA oligonucleotide

<400> SEQUENCE: 15
gcgtacgcaa attaaagtcc aga            23

<210> SEQ ID NO 16
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 16
cagcatccta aacagctcgc agaat            25

<210> SEQ ID NO 17
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 17
taccatgcga ccagtggtgc gct            23

<210> SEQ ID NO 18
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 18
gaattctggt tatcatcggg gaa            23

<210> SEQ ID NO 19
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 19
ctacaacgcc tacgagtcct aca            23

<210> SEQ ID NO 20
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 20
gttgcaccag aaaagtcaga gttg            24

<210> SEQ ID NO 21
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 21
ctcagtgatc ctgatcagat gaacg            25

```
<210> SEQ ID NO 22
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 22
agtccctggc ggcaagatta tcaag                                    25

<210> SEQ ID NO 23
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 23
acctgactcc tgaggagaag tctgc                                    25

<210> SEQ ID NO 24
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 24
tagccacacc agccaccact ttctg                                    25

<210> SEQ ID NO 25
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 25
atgcacggca tctgggaatc                                          20

<210> SEQ ID NO 26
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 26
gctactgtcc tgcaagttgc tgtc                                     24

<210> SEQ ID NO 27
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 27
cagtctgacc agcgtgaaaa                                          20

<210> SEQ ID NO 28
<211> LENGTH: 20
<212> TYPE: DNA
<213> ORGANISM: Artificial sequence
<220> FEATURE:
<223> OTHER INFORMATION: Single strand DNA oligonucleotide
```

<400> SEQUENCE: 28
ggccatccaa atctgtccta                                                    20

<210> SEQ ID NO 29
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 29
actaacatga gtgtggatcc                                                    20

<210> SEQ ID NO 30
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 30
tcatcttcac acgtcttcag                                                    20

<210> SEQ ID NO 31
<211> LENGTH: 288
<212> TYPE: PRT
<213> ORGANISM: Homo sapiens

<400> SEQUENCE: 31

```
Met Val Gly Val Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
                20                  25                  30

Pro Gly Ala Ala Ala Trp Glu Ala Ala Leu Pro Arg Arg Arg Pro Arg
            35                  40                  45

Arg His Pro Ser Val Asn Pro Ser Arg Ala Ala Gly Ser Pro Arg
    50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
                100                 105                 110

Gly Thr Ala Ala Pro Arg Ala Ala Pro Ala Ala Arg Gly Ser Arg Pro
            115                 120                 125

Gly Pro Ala Gly Thr Met Ala Ala Gly Ser Ile Thr Thr Leu Pro Ala
130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
            195                 200                 205

Gly Val Cys Ala Asn Arg Tyr Leu Ala Met Lys Glu Asp Gly Arg Leu
210                 215                 220

Leu Ala Ser Lys Cys Val Thr Asp Glu Cys Phe Phe Phe Glu Arg Leu
```

```
                225                 230                 235                 240
            Glu Ser Asn Asn Tyr Asn Thr Tyr Arg Ser Arg Lys Tyr Thr Ser Trp
                            245                 250                 255

Tyr Val Ala Leu Lys Arg Thr Gly Gln Tyr Lys Leu Gly Ser Lys Thr
                            260                 265                 270

Gly Pro Gly Gln Lys Ala Ile Leu Phe Leu Pro Met Ser Ala Lys Ser
                        275                 280                 285

<210> SEQ ID NO 32
<211> LENGTH: 6774
<212> TYPE: DNA
<213> ORGANISM: Homo sapiens

<400> SEQUENCE: 32
cggccccaga aaacccgagc gagtaggggg cggcgcgcag gagggaggag aactgggggc      60
gcgggaggct ggtgggtgtg gggggtggag atgtagaaga tgtgacgccg cggcccggcg     120
ggtgccagat tagcggacgc ggtgcccgcg gttgcaacgg gatcccgggc gctgcagctt     180
gggaggcggc tctccccagg cggcgtccgc ggagacaccc atccgtgaac cccaggtccc     240
gggccgccgg ctcgccgcgc accaggggcc ggcggacaga gagcggccg agcggctcga      300 ggctggggga ccgcgggcgc ggccgcgcgc tgccgggcgg gaggctgggg ggccggggcc     360
ggggccgtgc cccggagcgg gtcggaggcc ggggccgggg ccggggacg gcggctcccc     420 gcgcggctcc agcggctcgg ggatcccggc cgggcccgc agggaccatg gcagccggga     480
gcatcaccac gctgcccgcc ttgcccgagg atggcggcag cggcgccttc ccgcccggcc     540
acttcaagga ccccaagcgg ctgtactgca aaaacggggg cttcttcctg cgcatccacc     600 ccgacgccg agttgacggg gtccgggaga gagcgaccc tcacatcaag ctacaacttc      660
aagcagaaga gagaggagtt gtgtctatca aggagtgtg tgctaaccgt tacctggcta     720
tgaaggaaga tggaagatta ctggcttcta aatgtgttac ggatgagtgt ttcttttttg     780
aacgattgga atctaataac tacaatactt accggtcaag gaaatacacc agttggtatg     840
tggcactgaa acgaactggg cagtataaac ttggatccaa acaggacct gggcagaaag      900 ctatactttt tcttccaatg tctgctaaga gctgatttta atggccacat ctaatctcat     960
ttcacatgaa agaagaagta tattttagaa atttgttaat gagagtaaaa gaaaataaat    1020
gtgtatagct cagtttggat aattggtcaa acaattttt atccagtagt aaaatatgta     1080
accattgtcc cagtaaagaa aaataacaaa agttgtaaaa tgtatattct ccctttata     1140 ttgcatctgc tgttacccag tgaagcttac ctagagcaat gatctttttc acgcatttgc    1200
tttattcgaa aagaggcttt taaaatgtgc atgtttagaa acaaaatttc ttcatggaaa    1260
tcatatacat tagaaaatca cagtcagatg tttaatcaat ccaaaatgtc cactatttct    1320
tatgtcattc gttagtctac atgtttctaa acatataaat gtgaatttaa tcaattcctt    1380
tcatagtttt ataattctct ggcagttcct tatgatagag tttataaaac agtcctgtgt    1440
aaactgctgg aagttcttcc acagtcaggt caattttgtc aaaccttct ctgtacccat     1500 acagcagcag cctagcaact ctgctggtga tgggagttgt attttcagtc ttcgccaggt    1560
cattgagatc catccactca catcttaagc attcttcctg gcaaaattt atggtgaatg     1620 aatatggctt taggcggcag atgatataca tatctgactt cccaaaagct ccaggatttg    1680
tgtgctgttg ccgaatactc aggacggacc tgaattctga tttttatacca gtctcttcaa   1740 aaacttctcg aaccgctgtg tctcctacgt aaaaaaagag atgtacaaat caataataat    1800
```

```
tacactttta gaaactgtat catcaaagat tttcagttaa agtagcatta tgtaaaggct      1860
caaaacatta ccctaacaaa gtaaagtttt caatacaaat tctttgcctt gtggatatca      1920
agaaatccca aaatattttc ttaccactgt aaattcaaga agcttttgaa atgctgaata      1980
tttctttggc tgctacttgg aggcttatct acctgtacat ttttggggtc agctcttttt      2040
aacttcttgc tgctcttttt cccaaaaggt aaaatatag attgaaaagt taaaacattt       2100
tgcatggctg cagttccttt gtttcttgag ataagattcc aaagaactta gattcatttc      2160
ttcaacaccg aaatgctgga ggtgtttgat cagttttcaa gaaacttgga atataaataa      2220 tttttataatt caacaaaggt tttcacattt tataaggttg attttcaat taaatgcaaa      2280 tttgtgtggc aggatttta ttgccattaa catatttttg tggctgcttt ttctacacat       2340
ccagatggtc cctctaactg gcttttctct aattttgtga tgttctgtca ttgtctccca      2400
aagtatttag gagaagccct taaaaagct gccttcctct accactttgc tggaaagctt       2460
cacaattgtc acagacaaag attttttgttc caatactcgt tttgcctcta tttttcttgt    2520
ttgtcaaata gtaaatgata tttgcccttg cagtaattct actggtgaaa aacatgcaaa     2580
gaagaggaag tcacagaaac atgtctcaat tcccatgtgc tgtgactgta gactgtctta     2640
ccatagactg tcttacccat cccctggata tgctcttgtt ttttccctct aatagctatg    2700
gaaagatgca tagaaagagt ataatgtttt aaaacataag gcattcgtct gccattttc     2760 aattacatgc tgacttccct tacaattgag atttgcccat aggttaaaca tggttagaaa    2820
caactgaaag cataaaagaa aaatctaggc cgggtgcagt ggctcatgcc tatattccct   2880
gcactttggg aggccaaagc aggaggatcg cttgagccca ggagttcaag accaacctgg   2940 tgaaacccg tctctacaaa aaacacaaa aatagccag gcatggtggc gtgtacatgt       3000
ggtctcagat acttgggagg ctgaggtggg agggttgatc acttgaggct gagaggtcaa   3060
ggttgcagtg agccataatc gtgccactgc agtccagcct aggcaacaga gtgagacttt    3120
gtctcaaaaa aagagaaatt tccttaata agaaaagtaa tttttactct gatgtgcaat    3180
acatttgtta ttaaatttat tatttaagat ggtagcacta gtcttaaatt gtataaaata    3240 tccccctaaca tgtttaaatg tccatttta ttcattatgc tttgaaaaat aattatgggg    3300
aaatacatgt ttgttattaa atttattatt aaagatagta gcactagtct taaatttgat    3360
ataacatctc ctaacttgtt taaatgtcca tttttattct ttatgtttga aaataaatta    3420
tggggatcct atttagctct tagtaccact aatcaaaagt tcggcatgta gctcatgatc    3480
tatgctgttt ctatgtcgtg gaagcaccgg atggggtag tgagcaaatc tgccctgctc    3540
agcagtcacc atagcagctg actgaaaatc agcactgcct gagtagtttt gatcagttta   3600
acttgaatca ctaactgact gaaaattgaa tgggcaaata agtgcttttg tctccagagt    3660
atgcgggaga cccttccacc tcaagatgga tatttcttcc ccaaggattt caagatgaat    3720
tgaaattttt aatcaagata gtgtgcttta ttctgttgta ttttttatta ttttaatata    3780
ctgtaagcca aactgaaata acatttgctg ttttataggt ttgaagaaca taggaaaaac    3840
taagaggttt tgtttttatt tttgctgatg aagagatatg tttaaatatg ttgtattgtt    3900
ttgtttagtt acaggacaat aatgaaatgg agtttatatt tgttatttct attttgttat    3960
atttaataat agaattagat tgaaataaaa tataatggga aataatctgc agaatgtggg    4020
ttttcctggt gtttccctct gactctagtg cactgatgat ctctgataag gctcagctgc    4080
tttatagttc tctggctaat gcagcagata ctcttcctgc cagtggtaat acgatttttt    4140
aagaaggcag tttgtcaatt ttaatcttgt ggataccttt atactcttag ggtattattt    4200
```

```
tatacaaaag ccttgaggat tgcattctat tttctatatg accctcttga tatttaaaaa   4260
acactatgga taacaattct tcatttacct agtattatga aagaatgaag gagttcaaac   4320
aaatgtgttt cccagttaac tagggtttac tgtttgagcc aatataaatg tttaactgtt   4380
tgtgatggca gtattcctaa agtacattgc atgttttcct aaatacagag tttaaataat   4440
ttcagtaatt cttagatgat tcagcttcat cattaagaat atcttttgtt ttatgttgag   4500
ttagaaatgc cttcatatag acatagtctt tcagacctct actgtcagtt ttcatttcta   4560
gctgctttca gggttttatg aattttcagg caaagcttta atttatacta agcttaggaa   4620
gtatggctaa tgccaacggc agttttttc ttcttaattc cacatgactg aggcatatat   4680
gatctctggg taggtgagtt gttgtgacaa ccacaagcac tttttttttt tttaaagaaa   4740
aaaaggtagt gaatttttaa tcatctggac tttaagaagg attctggagt atacttaggc   4800
ctgaaattat atatatttgg cttggaaatg tgttttcttt caattacatc tacaagtaag   4860
tacagctgaa attcagagga cccataagag ttcacatgaa aaaaatcaat ttatttgaaa   4920
aggcaagatg caggagagag gaagccttgc aaacctgcag actgcttttt gcccaatata   4980
gattgggtaa ggctgcaaaa cataagctta attagctcac atgctctgct ctcacgtggc   5040
accagtggat agtgtgagag aattaggctg tagaacaaat ggccttctct ttcagcattc   5100
acaccactac aaaatcatct tttatatcaa cagaagaata agcataaact aagcaaaagg   5160
tcaataagta cctgaaacca agattggcta gagatatatc ttaatgcaat ccatttctg   5220 atggattgtt acgagttggc tatataatgt atgtatggta ttttgatttg tgtaaaagtt   5280
ttaaaaatca agctttaagt acatggacat ttttaaataa aatatttaaa gacaatttag   5340
aaaattgcct taatatcatt gttggctaaa tagaatagg gacatgcata ttaaggaaaa    5400
ggtcatggag aaataatatt ggtatcaaac aaatacattg atttgtcatg atacacattg   5460
aatttgatcc aatagtttaa ggaataggta ggaaaatttg gtttctattt ttcgatttcc   5520
tgtaaatcag tgacataaat aattcttagc ttatttata tttccttgtc ttaaatactg    5580
agctcagtaa gttgtgttag gggattattt ctcagttgag actttcttat atgacatttt   5640
actatgtttt gacttcctga ctattaaaaa taaatagtag atacaatttt cataaagtga   5700
agaattatat aatcactgct ttataactga ctttattata tttatttcaa agttcattta   5760
aaggctacta ttcatcctct gtgatggaat ggtcaggaat ttgttttctc atagtttaat   5820
tccaacaaca atattagtcg tatccaaaat aacctttaat gctaaacttt actgatgtat   5880
atccaaagct tctcattttc agacagatta atccagaagc agtcataaac agaagaatag   5940
gtggtatgtt cctaatgata ttatttctac taatggaata aactgtaata ttagaaatta   6000
tgctgctaat tatatcagct ctgaggtaat ttctgaaatg ttcagactca gtcggaacaa   6060
attggaaaat ttaaattttt attcttagct ataaagcaag aaagtaaaca cattaatttc   6120
ctcaacattt ttaagccaat taaaaatata aagatacac accatatct tcttcaggct    6180 ctgacaggcc tcctggaaac ttccacatat ttttcaactg cagtataaag tcagaaaata   6240
aagttaacat aactttcact aacacacaca tatgtagatt tcacaaaatc cacctataat   6300
tggtcaaagt ggttgagaat atatttttta gtaattgcat gcaaaatttt tctagcttcc   6360
atcctttctc cctcgtttct tcttttttg ggggagctgg taactgatga aatcttttcc    6420 cacctttct cttcaggaaa tataagtggt tttgttggt taacgtgata cattctgtat     6480
gaatgaaaca ttggagggaa acatctactg aatttctgta atttaaaata ttttgctgct   6540
```

-continued

```
agttaactat gaacagatag aagaatctta cagatgctgc tataaataag tagaaaatat    6600
aaatttcatc actaaaatat gctattttaa aatctatttc ctatattgta tttctaatca    6660
gatgtattac tcttattatt tctattgtat gtgttaatga ttttatgtaa aaatgtaatt    6720
gcttttcatg agtagtatga ataaaattga ttagtttgtg ttttcttgtc tccc          6774
```

<210> SEQ ID NO 33
<211> LENGTH: 365
<212> TYPE: PRT
<213> ORGANISM: Homo sapiens

<400> SEQUENCE: 33

```
Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335
```

```
Asn Lys Asp Asp Asp Asn Ile Leu Phe Arg Asp Ser Ala Asn Ala Thr
            340                 345                 350

Ser Leu Pro Gly Ser Arg Arg Gly Ser Cys Gly Leu
            355                 360                 365

<210> SEQ ID NO 34
<211> LENGTH: 44
<212> TYPE: PRT
<213> ORGANISM: Homo sapiens

<400> SEQUENCE: 34

Val Pro Pro Glu Glu Pro Gln Leu Ser Cys Phe Arg Lys Ser Pro Leu
1               5                   10                  15

Ser Asn Val Val Cys Glu Trp Gly Pro Arg Ser Thr Pro Ser Leu Thr
            20                  25                  30

Thr Lys Ala Val Leu Leu Val Arg Lys Phe Gln Asn
        35                  40

<210> SEQ ID NO 35
<211> LENGTH: 212
<212> TYPE: PRT
<213> ORGANISM: Homo sapiens

<400> SEQUENCE: 35

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 36
<211> LENGTH: 543
<212> TYPE: PRT
<213> ORGANISM: Artificial sequence
<220> FEATURE:
```

<223> OTHER INFORMATION: IL6R/IL6 chimeric protein

<400> SEQUENCE: 36

```
Met Leu Ala Val Gly Cys Ala Leu Leu Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
            35                  40                  45

Gly Val Glu Pro Glu Asp Asn Ala Thr Val His Trp Val Leu Arg Lys
        50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
                100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Leu Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
            195                 200                 205

Gln Gly Cys Gly Ile Leu Gln Pro Asp Pro Pro Ala Asn Ile Thr Val
        210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
            275                 280                 285

Val Val Gln Leu Arg Ala Gln Glu Glu Phe Gly Gln Gly Glu Trp Ser
        290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Glu Phe Met Pro Val Pro Pro Gly Glu Asp Ser Lys
            355                 360                 365

Asp Val Ala Ala Pro His Arg Gln Pro Leu Thr Ser Ser Glu Arg Ile
        370                 375                 380

Asp Lys Gln Ile Arg Tyr Ile Leu Asp Gly Ile Ser Ala Leu Arg Lys
385                 390                 395                 400
```

```
Glu Thr Cys Asn Lys Ser Asn Met Cys Glu Ser Ser Lys Glu Ala Leu
                405                 410                 415

Ala Glu Asn Asn Leu Asn Leu Pro Lys Met Ala Glu Lys Asp Gly Cys
            420                 425                 430

Phe Gln Ser Gly Phe Asn Glu Glu Thr Cys Leu Val Lys Ile Ile Thr
            435                 440                 445

Gly Leu Leu Glu Phe Glu Val Tyr Leu Glu Tyr Leu Gln Asn Arg Phe
        450                 455                 460

Glu Ser Ser Glu Glu Gln Ala Arg Ala Val Gln Met Ser Thr Lys Val
465                 470                 475                 480

Leu Ile Gln Phe Leu Gln Lys Lys Ala Lys Asn Leu Asp Ala Ile Thr
                485                 490                 495

Thr Pro Asp Pro Thr Thr Asn Ala Ser Leu Leu Thr Lys Leu Gln Ala
            500                 505                 510

Gln Asn Gln Trp Leu Gln Asp Met Thr Thr His Leu Ile Leu Arg Ser
            515                 520                 525

Phe Lys Glu Phe Leu Gln Ser Ser Leu Arg Ala Leu Arg Gln Met
        530                 535                 540

<210> SEQ ID NO 37
<211> LENGTH: 202
<212> TYPE: PRT
<213> ORGANISM: Homo sapiens

<400> SEQUENCE: 37

Met Lys Val Leu Ala Ala Gly Val Val Pro Leu Leu Leu Val Leu His
1               5                   10                  15

Trp Lys His Gly Ala Gly Ser Pro Leu Pro Ile Thr Pro Val Asn Ala
            20                  25                  30

Thr Cys Ala Ile Arg His Pro Cys His Asn Asn Leu Met Asn Gln Ile
        35                  40                  45

Arg Ser Gln Leu Ala Gln Leu Asn Gly Ser Ala Asn Ala Leu Phe Ile
    50                  55                  60

Leu Tyr Tyr Thr Ala Gln Gly Glu Pro Phe Pro Asn Asn Leu Asp Lys
65              70                  75                  80

Leu Cys Gly Pro Asn Val Thr Asp Phe Pro Pro Phe His Ala Asn Gly
                85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
        115                 120                 125

Ser Ala Leu Ser Leu His Ser Lys Leu Asn Ala Thr Ala Asp Ile Leu
    130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Asp Thr Ser Gly Lys Asp
                165                 170                 175

Val Phe Gln Lys Lys Lys Leu Gly Cys Gln Leu Leu Gly Lys Tyr Lys
            180                 185                 190

Gln Ile Ile Ala Val Leu Ala Gln Ala Phe
        195                 200

<210> SEQ ID NO 38
<211> LENGTH: 3935
<212> TYPE: DNA
<213> ORGANISM: Homo sapiens
```

<400> SEQUENCE: 38

```
tacaacacag gctccagtat ataaatcagg caaattcccc atttgagcat gaacctctga      60
aaactgccgg catctgaggt ttcctccaag gccctctgaa gtgcagccca taatgaaggt     120
cttggcggca ggagttgtgc ccctgctgtt ggttctgcac tggaaacatg gggcggggag     180
cccccctccc atcacccctg tcaacgccac ctgtgccata cgccacccat gtcacaacaa     240
cctcatgaac cagatcagga gccaactggc acagctcaat ggcagtgcca atgccctctt     300
tattctctat tacacagccc aggggagcc gttccccaac aacctggaca agctatgtgg     360
ccccaacgtg acggacttcc cgcccttcca cgccaacggc acggagaagg ccaagctggt     420
ggagctgtac cgcatagtcg tgtaccttgg cacctccctg gcaacatca cccgggacca     480
gaagatcctc aacccagtg ccctcagcct ccacagcaag ctcaacgcca ccgccgacat     540
cctgcgaggc ctccttagca acgtgctgtg ccgcctgtgc agcaagtacc acgtgggcca     600
tgtggacgtg acctacggcc ctgacacctc gggtaaggat gtcttccaga agaagaagct     660
gggctgtcaa ctcctgggga agtataagca gatcatcgcc gtgttggccc aggccttcta     720
gcaggaggtc ttgaagtgtg ctgtgaaccg agggatctca ggagttgggt ccagatgtgg     780
gggcctgtcc aagggtggct ggggcccagg gcatcgctaa acccaaatgg gggctgctgg     840
cagaccccga gggtgcctgg ccagtccact ccactctggg ctgggctgtg atgaagctga     900
gcagagtgga aacttccata gggagggagc tagaagaagg tgccccttcc tctgggagat     960
tgtggactgg ggagcgtggg ctggacttct gcctctactt gtccctttgg ccccttgctc    1020
actttgtgca gtgaacaaac tacacaagtc atctacaaga gccctgacca cagggtgaga    1080
cagcagggcc caggggagtg gaccagcccc cagcaaatta tcaccatctg tgcctttgct    1140
gccccttagg ttgggactta ggtgggccag aggggctagg atcccaaagg actccttgtc    1200
ccctagaagt ttgatgagtg gaagatagag aggggcctct gggatggaag gctgtcttct    1260
tttgaggatg atcagagaac ttgggcatag gaacaatctg gcagaagttt ccagaaggag    1320
gtcacttggc attcaggctc ttggggaggc agagaagcca ccttcaggcc tggaaggaa     1380
gacactggga ggaggagagg cctggaaagc tttggtaggt tcttcgttct cttccccgtg    1440
atcttccctg cagcctggga tggccagggt ctgatggctg gacctgcagc aggggtttgt    1500
ggaggtgggt agggcagggg caggttgcta agtcaggtgc agaggttctg agggacccag    1560
gctcttcctc tgggtaaagg tctgtaagaa ggggctgggg tagctcagag tagcagctca    1620
catctgaggc cctgggaggc cttgtgaggt cacacagagg tacttgaggg ggactggagg    1680
ccgtctctgg tccccagggc aagggaacag cagaacttag ggtcagggtc tcagggaacc    1740
ctgagctcca gcgtgctgt gcgtctgacc tggcatgatt tctatttatt atgatatcct    1800
atttatatta acttattggt gctttcagtg gccaagttaa ttccccttc cctggtccct    1860
actcaacaaa atatgatgat ggctcccgac acaagcgcca gggccagggc ttagcagggc    1920
ctggtctgga agtcgacaat gttacaagtg gaataagcct tacgggtgaa gctcagagaa    1980
gggtcggatc tgagagaatg gggaggcctg agtgggagtg gggggccttg ctccaccccc    2040
ccccatcccc tactgtgact tgctttaggg tgtcagggtc caggctgcag gggctgggcc    2100
aatttgtgga gaggccgggt gcctttctgt cttgattcca gggggctggt tcacactgtt    2160
cttgggcgcc ccagcattgt gttgtgaggc gcactgttcc tggcagatat tgtgccccct    2220
ggagcagtgg gcaagacagt ccttgtggcc caccctgtcc ttgtttctgt gtcccatgc    2280
```

```
tgcctctgaa atagcgccct ggaacaaccc tgcccctgca cccagcatgc tccgacacag    2340
cagggaagct cctcctgtgg cccggacacc catagacggt gcggggggcc tggctgggcc    2400 agacccccagg aagtgggggt agactggggg gatcagctgc ccattgctcc caagaggagg   2460
```

```
tgcctctgaa atagcgccct ggaacaaccc tgcccctgca cccagcatgc tccgacacag    2340
cagggaagct cctcctgtgg cccggacacc catagacggt gcggggggcc tggctgggcc    2400
agaccccagg aagtgggggt agactggggg gatcagctgc ccattgctcc caagaggagg    2460
agagggaggc tgcagatgcc tgggactcag accaggaagc tgtgggccct cctgctccac    2520
ccccatccca ctcccaccca tgtctgggct cccaggcagg aacccgatcc tcttcctttg    2580
tgctggggcc aggcgagtgg agaaacgccc tccagtctga gagcagggga gggaaggagg    2640
cagcagagtt ggggcagctg ctcagagcag tgttctggct tcttctcaaa ccctgagcgg    2700
gctgccggcc tccaagttcc tccgacaaga tgatggtact aattatggta cttttcactc    2760
actttgcacc tttccctgtc gctctctaag cactttacct ggatggcgcg tgggcagtgt    2820
gcaggcaggt cctgaggcct ggggttgggg tggagggtgc ggcccggagt tgtccatctg    2880
tccatcccaa cagcaagacg aggatgtggc tgttgagatg tgggccacac tcaccccttgt   2940 ccaggatgca gggactgcct ctccttcct gcttcatccg gcttagcttg ggctggctg     3000 cattccccca ggatgggctt cgagaaagac aaacttgtct ggaaaccaga gttgctgatt    3060
ccacccgggg ggcccggctg actcgcccat cacctcatct ccctgtggac ttgggagctc    3120
tgtgccaggc ccaccttgcg gccctggctc tgagtcgctc tccacccag cctggacttg    3180 gccccatggg acccatcctc agtgctccct ccagatcccg tccggcagct tggcgtccac    3240
cctgcacagc atcactgaat cacagagcct ttgcgtgaaa cagctctgcc aggccgggag    3300 ctgggttct cttccctttt tatctgctgg tgtggaccac acctgggcct ggccggagga    3360
agagagagtt taccaagaga gatgtctccg ggcccttatt tattatttaa acatttttt     3420 aaaaagcact gctagtttac ttgtctctcc tccccatcgt ccccatcgtc ctccttgtcc    3480
ctgacttggg gcacttccac cctgacccag ccagtccagc tctgccttgc cggctctcca    3540
gagtagacat agtgtgtggg gttggagctc tggcacccgg ggaggtagca tttccctgca    3600
gatggtacag atgttcctgc cttagagtca tctctagttc cccacctcaa tcccggcatc    3660
cagccttcag tcccgcccac gtgctagctc cgtgggccca ccgtgcggcc ttagaggttt    3720
ccctccttcc tttccactga aaagcacatg gccttgggtg acaaattcct ctttgatgaa    3780
tgtaccctgt ggggatgttt catactgaca gattatttt atttattcaa tgtcatattt     3840
aaaatattta ttttttatac caaatgaata ctttttttt taagaaaaaa aagagaaatg    3900
aataaagaat ctactcttga aaaaaaaaaa aaaaa                               3935
```

<210> SEQ ID NO 39
<211> LENGTH: 244
<212> TYPE: PRT
<213> ORGANISM: Homo sapiens

<400> SEQUENCE: 39

Val Pro Pro Glu Glu Pro Gln Leu Ser Cys Phe Arg Lys Ser Pro Leu
1               5                   10                  15

Ser Asn Val Val Cys Glu Trp Gly Pro Arg Ser Thr Pro Ser Leu Thr
            20                  25                  30

Thr Lys Ala Val Leu Leu Val Arg Lys Phe Gln Asn Ser Pro Ala Glu
        35                  40                  45

Asp Phe Gln Glu Pro Cys Gln Tyr Ser Gln Glu Ser Gln Lys Phe Ser
    50                  55                  60

Cys Gln Leu Ala Val Pro Glu Gly Asp Ser Ser Phe Tyr Ile Val Ser
65                  70                  75                  80

```
Met Cys Val Ala Ser Ser Val Gly Ser Lys Phe Ser Lys Thr Gln Thr
                85                  90                  95

Phe Gln Gly Cys Gly Ile Leu Gln Pro Asp Pro Ala Asn Ile Thr
            100                 105             110

Val Thr Ala Val Ala Arg Asn Pro Arg Trp Leu Ser Val Thr Trp Gln
        115                 120                 125

Asp Pro His Ser Trp Asn Ser Ser Phe Tyr Arg Leu Arg Phe Glu Leu
    130             135                 140

Arg Tyr Arg Ala Glu Arg Ser Lys Thr Phe Thr Thr Trp Met Val Lys
145             150                 155                     160

Asp Leu Gln His His Cys Val Ile His Asp Ala Trp Ser Gly Leu Arg
            165                 170                 175

His Val Val Gln Leu Arg Ala Gln Glu Glu Phe Gly Gln Gly Glu Trp
            180                 185                 190

Ser Glu Trp Ser Pro Glu Ala Met Gly Thr Pro Trp Thr Glu Ser Arg
            195                 200                 205

Ser Pro Pro Ala Glu Asn Glu Val Ser Thr Pro Met Gln Ala Leu Thr
        210                 215                 220

Thr Asn Lys Asp Asp Asp Asn Ile Leu Phe Arg Asp Ser Ala Asn Ala
225             230                 235                     240

Thr Ser Leu Pro
```